（12）United States Patent
Harden et al.

(10) Patent No.: US 7,510,868 B2
(45) Date of Patent: Mar. 31, 2009

(54) CHIMERIC ADENOVIRUSES FOR USE IN CANCER TREATMENT

(76) Inventors: Paul Harden, 879 Larkspur Ct., Brentwood, CA (US) 94513; Terry Hermiston, 9 Seamast Passage, Corte Madera, CA (US) 94925; Irene Kuhn, 5647 San Jose Ave., Richmond, CA (US) 94804

( * ) Notice: Subject to any disclaimer, the term of this patent is extended or adjusted under 35 U.S.C. 154(b) by 332 days.

(21) Appl. No.: 11/136,912

(22) Filed: May 24, 2005

(65) Prior Publication Data

US 2005/0265973 A1 Dec. 1, 2005

Related U.S. Application Data

(60) Provisional application No. 60/574,851, filed on May 26, 2004.

(51) Int. Cl.
*C12N 15/63* (2006.01)
*A61K 35/00* (2006.01)

(52) U.S. Cl. ............... 435/320.1; 435/91.1; 435/91.4; 435/91.42; 536/23.1

(58) Field of Classification Search ............ 435/320.1
See application file for complete search history.

(56) References Cited

U.S. PATENT DOCUMENTS

| 5,677,178 | A | 10/1997 | McCormick et al. | |
|---|---|---|---|---|
| 5,972,706 | A | 10/1999 | McCormick et al. | |
| 2003/0017138 | A1 | 1/2003 | Havenga et al. | |
| 2004/0136958 | A1* | 7/2004 | Wadell et al. | 424/93.2 |
| 2004/0151696 | A1 | 8/2004 | Johnson et al. | |

FOREIGN PATENT DOCUMENTS

| SE | 0100035-5 | * | 1/2001 |
|---|---|---|---|
| WO | 02053759 A1 | * | 7/2002 |

OTHER PUBLICATIONS

Heise et al. "Onyx-015, an E1B gene-attenuated adenovirus, causes tumor-specific cytolysis and antitumoral efficacy that can be augmented by standard chemotherapeutic agents." *Nat. Med.* vol. 3, No. 6, 639-645. (1997).
Mei et al. "Comparative analysis of the genome organization of human adenovirus 11, a member of the human adenovirus species B, and the commonly used human adenovirus 5 vector, a member of species C." *J. Gen. Virology.* vol. 84, 2061-2071. (2003).
Grill et al. "The organotypic multicellular spheroid is a relevant three-dimensional model to study adenovirus replication and penetration in human tumors in vitro." *Mol. Therapy.* vol. 6. No. 5, 609-614. (2002).
Lai et al. "Adenovirus and adeno-associated virus vectors." *DNA Cell Bio.* vol. 21. No. 12, 895-913. (2002).
Stone et al. "The complete nucleotide sequence, genome organization, and origin of human adenovirus type 11." *Virology.* vol. 309, 152-165. (2003).
Yan et al. "Developing novel oncolytic adenoviruses through bioselection." *J. Virol.* vol. 77. No. 4, 2640-2650. (2003).
Stevenson et al. "Selective targeting of human cells by a chimeric adenovirus vector containing a modified fiber protein." *J. Virol.* vol. 71. No. 6, 4782-4790. (1997).
Hermiston et al., "Armed Therapeutic Viruses: Strategies and Challenges to Arming Oncolytic Viruses With Therapeutic Genes." *Cancer Gene Therapy,* (2002) vol. 9, pp. 1022-1035.
Hermiston et al., "The Discovery and Development of Selectively Replicating Adenoviruses as Anticancer Agents." *Tumor Targeting,* (2000) vol. 4, pp. 218-224.
Puthupparampil et al., "Tumor Growth Inhibition from Tumor Targeted Delivery of Diphtheria Toxin Gene." *Molecular Therapy,* (2005) vol. 11, Supplement No. 1, p. A124.

* cited by examiner

*Primary Examiner*—Bruce R. Campell
*Assistant Examiner*—Bao Qun Li
(74) *Attorney, Agent, or Firm*—Banner, Witcoff, Ltd.

(57) ABSTRACT

The present invention relates to oncolytic adenoviruses having therapeutic applications. Recombinant chimeric adenoviruses, and methods to produce them are provided. The chimeric adenoviruses of the invention comprise nucleic acid sequences derived from adenoviral serotypes classified within the subgroups B through F and demonstrate an enhanced therapeutic index.

6 Claims, 9 Drawing Sheets

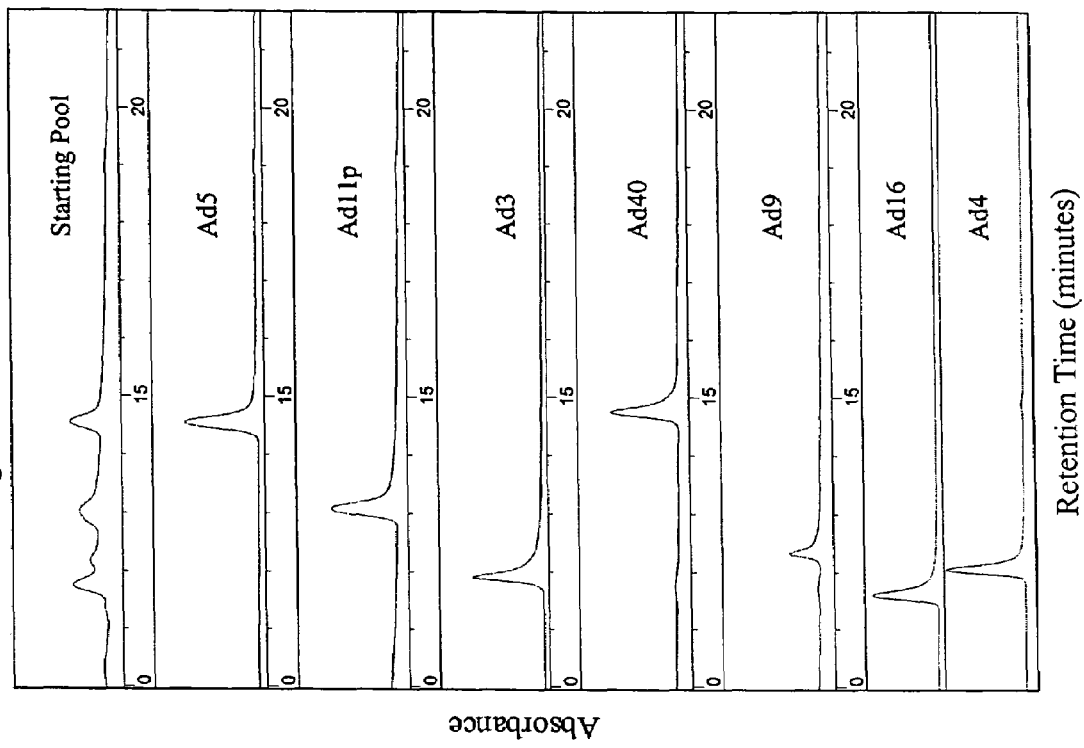

```
                            SEQUENCE LISTING

<160> NUMBER OF SEQ ID NOS: 8

<210> SEQ ID NO 1
<211> LENGTH: 32325
<212> TYPE: DNA
<213> ORGANISM: Adenovirus

<400> SEQUENCE: 1
ctatctatat aatatacctt atagatggaa tggtgccaat atgtaaatga ggtgatttta      60
aaaagtgtgg atcgtgtggt gattggctgt ggggttaacg gctaaaaggg gcggtgcgac     120
cgtgggaaaa tgacgttttg tgggggtgga gttttttttgc aagttgtcgc gggaaatgtg    180
acgcataaaa aggcttttttt ctcacggaac tacttagttt tcccacggta tttaacagga    240
aatgaggtag ttttgaccgg atgcaagtga aaattgttga ttttcgcgcg aaaactgaat    300
gaggaagtgt ttttctgaat aatgtggtat ttatggcagg gtggagtatt tgttcagggc    360
caggtagact ttgacccatt acgtggaggt ttcgattacc gtgtttttta cctgaatttc    420
cgcgtaccgt gtcaaagtct tctgttttta cgtaggtgtc agctgatcgc tagggtattt    480
atacctcagg gtttgtgtca agaggccact cttgagtgcc agcgagaaga gttttctcct    540
ctgcgccggc agtttaataa taaaaaaatg agagatttgc gatttctgcc tcaggaaata    600
atctctgctg agactggaaa tgaaatattg gagcttgtgg tgcacgccct gatgggagac    660
gatccggagc cacctgtgca gcttttttgag cctcctacgc ttcaggaact gtatgattta    720
gaggtagagg gatcggagga ttctaatgag gaagctgtaa atggcttttt taccgattct    780
atgcttttag ctgctaatga agggttagaa ttagatccgc ctttggacac ttttgatact    840
ccaggggtaa ttgtggaaag cggtacaggt gtaagaaaat tacctgattt gagttccgtg    900
gactgtgatt tgcactgcta tgaagacggg tttcctccga gtgatgagga ggaccatgaa    960
aaggagcagt ccatgcagac tgcagcgggt gagggagtga aggctgccaa tgttggtttt   1020
cagttggatt gcccggagct tcctggacat ggctgtaagt cttgtgaatt tcacaggaaa   1080
aatactggag taaggaact gttatgttcg ctttgttata tgagaacgca ctgccacttt   1140
atttacagta agtgtgttta agttaaaatt taaaggaata tgctgttttt cacatgtata   1200
ttgagtgtga gttttgtgct tcttattata ggtcctgtgt ctgatgctga tgaatcacca   1260
```

-continued

```
tctcctgatt ctactacctc acctcctgag attcaagcac ctgttcctgt ggacgtgcgc    1320
aagcccattc ctgtgaagct taagcctggg aaacgtccag cagtggaaaa acttgaggac    1380
ttgttacagg gtggggacgg accttttggac ttgagtacac ggaaacgtcc aagacaataa   1440
gtgttccata tccgtgttta cttaaggtga cgtcaatatt tgtgtgacag tgcaatgtaa    1500
taaaaatatg ttaactgttc actggttttt attgcttttt gggcggggac tcaggtatat    1560
aagtagaagc agacctgtgt ggttagctca taggagctgg ctttcatcca tggaggtttg    1620
ggccattttg gaagacctta ggaagactag gcaactgtta gagaacgctt cggacggagt    1680
ctccggtttt tggagattct ggttcgctag tgaattagct agggtagttt ttaggataaa    1740
acaggactat aaacaagaat ttgaaaagtt gttggtagat tgcccaggac tttttgaagc    1800
tcttaatttg ggccatcagg ttcactttaa agaaaaagtt ttatcagttt tagacttttc    1860
aaccccaggt agaactgctg ctgctgtggc ttttcttact tttatattag ataaatggat    1920
cccgcagact catttcagca ggggatacgt tttggatttc atagccacag cattgtggag    1980
aacatggaag gttcgcaaga tgaggacaat cttaggttac tggccagtgc agcctttggg    2040
tgtagcggga atcctgaggc atccaccggt catgccagcg ttctggagg aggaacagca    2100
agaggacaac ccgagagccg gcctggaccc tccagtggag gaggcggagt agctgacttg    2160
tctcctgaac tgcaacgggt gcttactgga tctacgtcca ctggacggga taggggcgtt   2220
aagagggaga gggcatctag tggtactgat gctagatctg agttggcttt aagtttaatg    2280
agtcgcagac gtcctgaaac catttggtgg catgaggttc agaaagaggg aagggatgaa    2340
gtttctgtat tgcaggagaa atattcactg gaacaggtga aaacatgttg gttggagcct    2400
gaggatgatt gggaggtggc cattaaaaat tatgccaaga tagctttgag gcctgataaa    2460
cagtataaga ttactagacg gattaatatc cggaatgctt gttacatatc tggaaatggg    2520
gctgaggtgg taatagatac tcaagacaag gcagttatta gatgctgcat gatggatatg    2580
tggcctgggg tagtcggtat ggaagcagta acttttgtaa atgttaagtt taggggagat    2640
ggttataatg gaatagtgtt tatggccaat accaaactta tattgcatgg ttgtagcttt    2700
tttggtttca acaatacctg tgtagatgcc tggggacagg ttagtgtacg gggatgtagt    2760
ttctatgcgt gttggattgc cacagctggc agaaccaaga gtcaattgtc tctgaagaaa    2820
tgcatatttc aaagatgtaa cctgggcatt ctgaatgaag gcgaagcaag ggtccgccac    2880
tgcgcttcta cagatactgg atgttttatt ttgattaagg gaaatgccag cgtaaagcat    2940
aacatgattt gcggtgcttc cgatgagagg cctatcaaa tgctcacttg tgctggtggg     3000
cattgtaata tgctggctac tgtgcatatt gtttcccatc aacgcaaaaa atggcctgtt    3060
tttgatcaca atgtgatgac gaagtgtacc atgcatgcag gtgggcgtag aggaatgttt    3120
atgccttacc agtgtaacat gaatcatgtg aaagtgttgt tggaaccaga tgccttttcc    3180
agaatgagcc taacaggaat ttttgacatg aacatgcaaa tctggaagat cctgaggtat    3240
gatgatacga gatcgagggt acgcgcatgc gaatgcggag gcaagcatgc caggttccag    3300
ccggtgtgtg tagatgtgac tgaagatctc agaccggatc atttggttat tgcccgcact    3360
ggagcagagt tcggatccag tggagaagaa actgactaag gtgagtattg gaaaacttt     3420
ggggtgggat tttcagatgg acagattgag taaaaatttg ttttttctgt cttgcagctg    3480
tcatgagtgg aaacgcttct tttaaggggg gagtcttcag cccttatctg acaggggcgtc   3540
tcccatcctg gcaggagtt cgtcagaatg ttatgggatc tactgtggat ggaagacccg     3600
tccaacccgc caattcttca acgctgacct atgctacttt aagttcttca cctttggacg    3660
```

```
cagctgcagc tgccgccgcc gcttctgttg ccgctaacac tgtgcttgga atgggttact   3720
atggaagcat catggctaat tccacttcct ctaataaccc ttctaccctg actcaggaca   3780
agttacttgt cctttggcc cagctggagg ctttgaccca acgtctgggt gaactttctc    3840
agcaggtggt cgagttgcga gtacaaactg agtctgctgt cggcacggca aagtctaaat   3900
aaaaaaatcc cagaatcaat gaataaataa acaagcttgt tgttgattta aaatcaagtg   3960
tttttatttc attttcgcg cacggtatgc cctagaccac cgatctctat cattgagaac    4020
tcggtggatt ttttccagga tcctatagag gtgggattga atgtttagat acatgggcat   4080
taggccgtct ttggggtgga gatagctcca ttgaagggat tcatgctccg gggtagtgtt   4140
gtaaatcacc cagtcataac aaggtcgcag tgcatggtgt tgcacaatat cttttagaag   4200
taggctgatt gccacagata agcccttggt gtaggtgttt acaaaccggt tgagctggga   4260
tgggtgcatt cggggtgaaa ttatgtgcat tttggattgg attttttaagt tggcaatatt   4320 gccgccaaga tcccgtcttg ggttcatgtt atgaaggacc accaagacgg tgtatccggt   4380
acatttagga aatttatcgt gcagcttgga tggaaaagcg tggaaaaatt tggagacacc   4440
cttgtgtcct ccaagatttt ccatgcactc atccatgata atagcaatgg ggccgtgggc   4500
agcggcgcgg gcaaacacgt tccgtgggtc tgacacatca tagttatgtt cctgagttaa   4560
atcatcataa gccatttaa tgaatttggg gcggagagta ccagattggg gtatgaatgt    4620
tccttcgggc cccggagcat agttcccctc acagatttgc atttcccaag ctttcagttc   4680
cgagggtgga atcatgtcca cctgggggc tatgaaaaac accgtttctg gggcgggggt    4740
gattaattgt gatgatagca aatttctgag caattgagat ttgccacatc cggtggggcc   4800
ataaatgatt ccgattacgg gttgcaggtg gtagtttagg gaacggcaac tgccgtcttc   4860
tcgaagcaag ggggccacct cgttcatcat ttcccttaca tgcatatttt cccgcaccaa   4920
atccattagg aggcgctctc ctcctagtga tagaagttct tgtagtgagg aaaagttttt   4980
cagcggtttc agaccgtcag ccatgggcat tttggagaga gtttgctgca aaagttctag   5040
tctgttccac agttcagtga tgtgttctat ggcatctcga tccagcagac ctcctcgttt   5100
cgcgggtttg gacggctcct ggaatagggt atgagacgat gggcgtccag cgctgccagg   5160
gttcggtcct tccagggtct cagtgttcga gtcaggttg tttccgtcac agtgaagggg    5220
tgtgcgcctg cttgggcgct tgccagggtg cgcttcagac tcatcctgct ggtcgaaaac   5280
ttctgtcgct tggcgccctg tatgtcggcc aagtagcagt ttaccatgag ttcgtagttg   5340
agcgcctcgg ctgcgtggcc tttggcgcgg agcttacctt tggaagtttt cttgcatacc   5400
gggcagtata gcatttcag cgcatacaac ttgggcgcaa ggaaaacgga ttctggggag    5460
tatgcatctg cgccgcagga ggcgcaaaca gtttcacatt ccaccagcca ggttaaatcc   5520
ggttcattgg ggtcaaaaac aagttttccg ccatattttt tgatgcgttt cttacctttg   5580
gtctccatga gttcgtgtcc tcgttgagtg acaaacaggc tgtccgtgtc cccgtagact   5640
gattttacag gcctcttctc cagtggagtg cctcggtctt cttcgtacag gaactctgac   5700
cactctgata caaaggcgcg cgtccaggcc agcacaaagg aggctatgtg ggaggggtag   5760
cgatcgttgt caaccagggg gtccaccttt tccaaagtat gcaaacacat gtcaccctct   5820
tcaacatcca ggaatgtgat tggcttgtag gtgtatttca cgtgacctgg ggtccccgct   5880
gggggggtat aaaagggggc ggttcttttgc tcttcctcac tgtcttccgg atcgctgtcc   5940
aggaacgtca gctgttgggg taggtattcc ctctcgaagg cgggcatgac ctctgcactc   6000
```

-continued

```
aggttgtcag tttctaagaa cgaggaggat ttgatattga cagtgccggt tgagatgcct    6060
ttcatgaggt tttcgtccat ctggtcagaa aacacaattt ttttattgtc aagtttggtg    6120
gcaaatgatc catacagggc gttggataaa agtttggcaa tggatcgcat ggtttggttc    6180
ttttccttgt ccgcgcgctc tttggcggcg atgttgagtt ggacatactc gcgtgccagg    6240
cacttccatt cggggaagat agttgttaat tcatctggca cgattctcac ttgccaccct    6300
cgattatgca aggtaattaa atccacactg gtggccacct cgcctcgaag gggttcattg    6360
gtccaacaga gcctacctcc tttcctagaa cagaaagggg aagtgggtc tagcataagt     6420 tcatcgggag ggtctgcatc catggtaaag attcccggaa gtaaatcctt atcaaaatag    6480
ctgatgggag tggggtcatc taaggccatt tgccattctc gagctgccag tgcgcgctca    6540
tatgggttaa ggggactgcc ccatggcatg ggatgggtga gtgcagaggc atacatgcca    6600
cagatgtcat agacgtagat gggatcctca agatgccta tgtaggttgg atagcatcgc     6660 cccctctga tacttgctcg cacatagtca tatagttcat gtgatggcgc tagcagcccc     6720
ggacccaagt tggtgcgatt gggttttcct gttctgtaga cgatctggcg aaagatggcg    6780
tgagaattgg aagagatggt gggtctttga aaaatgttga aatgggcatg aggtagacct    6840
acagagtctc tgacaaagtg ggcataagat tcttgaagct tggttaccag ttcggcggtg    6900
acaagtacgt ctagggcgca gtagtcaagt gtttcttgaa tgatgtcata acctggttgg    6960
tttttctttt cccacagttc gcggttgaga aggtattctt cgcgatcctt ccagtactct    7020
tctagcggaa acccgtcttt gtctgcacgg taagatccta gcatgtagaa ctgattaact    7080
gccttgtaag ggcagcagcc cttctctacg ggtagagagt atgcttgagc agcttttcgt    7140
agcgaagcgt gagtaagggc aaaggtgtct ctgaccatga ctttgaggaa ttggtatttg    7200
aagtcgatgt cgtcacaggc tccctgttcc cagagttgga agtctacccg tttcttgtag    7260
gcggggttgg gcaaagcgaa agtaacatca ttgaagagaa tcttgccggc cctgggcatg    7320
aaattgcgag tgatgcgaaa aggctgtggt acttccgctc ggttattgat aacctgggca    7380
gctaggacga tctcgtcgaa accgttgatg ttgtgtccta cgatgtataa ttctatgaaa    7440
cgcggcgtgc ctctgacgtg aggtagctta ctgagctcat caaaggttag gtctgtgggg    7500
tcagataagg cgtagtgttc gagagcccat tcgtgcaggt gaggattcgc tttaaggaag    7560
gaggaccaga ggtccactgc cagtgctgtt tgtaactggt cccggtactg acgaaaatgc    7620
cgtccgactg ccatttttc tggggtgacg caatagaagg tttgggggtc ctgccgccag     7680
cgatcccact tgagttttat ggcgaggtca taggcgatgt tgacgagccg ctggtctcca    7740
gagagtttca tgaccagcat gaaggggatt agctgcttgc caaaggaccc catccaggtg    7800
taggtttcca catcgtaggt gagaaagagc ctttctgtgc gaggatgaga gccaatcggg    7860
aagaactgga tctcctgcca ccagttggag gaatggctgt tgatgtgatg gaagtagaac    7920
tccctgcgac gcgccgagca ttcatgcttg tgcttgtaca gacggccgca gtagtcgcag    7980
cgttgcacgg gttgtatctc gtgaatgagt tgtacctggc ttcccttgac gagaaatttc    8040
agtgggaagc cgaggcctgg cgattgtatc tcgtgcttta ctatgttgtc tgcatcggcc    8100
tgttcatctt ctgtctcgat ggtggtcatg ctgacgagcc ctcgcgggag gcaagtccag    8160
acctcggcgc ggcaggggcg gagctcgagg acgagcgc gcaggctgga gctgccagg      8220 gtcctgagac gctgcggact caggttagta ggcagtgtca ggagattaac ttgcatgatc    8280
ttttggaggg cgtgcgggag gttcagatag tacttgatct caacgggtcc gttggtggag    8340
atgtcgatgg cttgcagggt tccgtgtccc ttgggcgcta ccaccgtgcc cttgtttttc    8400
```

```
attttggacg gcggtggctc tgttgcttct tgcatgttta aagcggtgt cgagggcgcg    8460 caccgggcgg caggggcggc tcgggacccg gcggcatggc tggcagtggt acgtcggcgc    8520
cgcgcgcggg taggttctgg tactgcgccc tgagaagact cgcatgcgcg acgacgcggc    8580
ggttgacatc ctggatctga cgcctctggg tgaaagctac cggccccgtg agcttgaacc    8640
tgaaagagag ttcaacagaa tcaatctcgg tatcgttgac ggcggcttgc ctaaggattt    8700
cttgcacgtc accagagttg tcctggtagg cgatctccgc catgaactgc tcgatctctt    8760
cctcttgaag atctccgcgg cccgctctct cgacggtggc cgcgaggtcg ttggagatgc    8820
gcccaatgag ttgagagaat gcattcatgc ccgcctcgtt ccagacgcgg ctgtagacca    8880
cggcccccac gggatctctc gcgcgcatga ccacctgggc gaggttgagc tccacgtggc    8940
gggtgaagac cgcatagttg cataggcgct ggaaaaggta gttgagtgtg gtggcgatgt    9000
gctcggtgac gaagaaatac atgatccatc gtctcagcgg catctcgctg acatcgccca    9060
gagcttccaa gcgctccatg gcctcgtaga agtccacggc aaaattaaaa aactgggagt    9120
ttcgcgcgga cacggtcaac tcctcttcca gaagacggat aagttcggcg atggtggtgc    9180
gcacctcgcg ctcgaaagcc cctgggattt cttcctcaat ctcttcttct tccactaaca    9240
tctcttcctc ttcaggtggg gctgcaggag gaggggaac gcggcgacgc cggcggcgca    9300
cgggcagacg gtcgatgaat cttcaatga cctctccgcg gcggcggcgc atggtttcag    9360
tgacggcgcg gccgttctcg cgcggtcgca gagtaaaaac accgccgcgc atctccttaa    9420
agtggtgact gggaggttct ccgtttggga gggagagggc gctgattata cattttatta    9480
attggcccgt agggactgca cgcagagatc tgatcgtgtc aagatccacg ggatctgaaa    9540
acctttcgac gaaagcgtct aaccagtcac agtcacaagg taggctgagt acggcttctt    9600
gtgggcgggg gtggttatgt gttcggtctg ggtcttctgt ttcttcttca tctcgggaag    9660
gtgagacgat gctgctggtg atgaaattaa agtaggcagt tctaagacgg cggatggtgg    9720
cgaggagcac caggtctttg ggtccggctt gctggatacg caggcgattg gccattcccc    9780
aagcattatc ctgacatcta gcaagatctt tgtagtagtc ttgcatgagc cgttctacgg    9840
gcacttcttc ctcacccgtt ctgccatgca tacgtgtgag tccaaatccg cgcattggtt    9900
gtaccagtgc caagtcagct acgactcttt cggcgaggat ggcttgctgt acttgggtaa    9960
gggtggcttg aaagtcatca aaatccacaa agcggtggta agctcctgta ttaatggtgt   10020
aagcacagtt ggccatgact gaccagttaa ctgtctggtg accagggcgc acgagctcgg   10080
tgtatttaag gcgcgaatag gcgcgggtgt caaagatgta atcgttgcag gtgcgcacca   10140
gatactggta ccctataaga aaatgcggcg gtggttggcg gtagagaggc catcgttctg   10200
tagctggagc gccagggggcg aggtcttcca acataaggcg gtgatagccg tagatgtacc   10260
tggacatcca ggtgattcct gcggcggtag tagaagcccg aggaaactcg cgtacgcggt   10320
tccaaatgtt gcgtagcggc atgaagtagt tcattgtagg cacggtttga ccagtgaggc   10380
gcgcgcagtc attgatgctc tatagacacg gagaaaatga aagcgttcag cgactcgact   10440
ccgtagcctg gaggaacgtg aacgggttgg gtcgcggtgt accccggttc gagacttgta   10500
ctcgagccgg ccggagccgc ggctaacgtg gtattggcac tcccgtctcg acccagccta   10560
caaaaatcca ggatacggaa tcgagtcgtt ttgctggttt ccgaatggca gggaagtgag   10620
tcctattttt ttttttgcc gctcagatgc atcccgtgct gcgacagatg cgccccaac    10680 aacagccccc ctcgcagcag cagcagcagc aatcacaaaa ggctgtccct gcaactactg   10740
```

```
caactgccgc cgtgagcggt gcgggacagc ccgcctatga tctggacttg gaagagggcg  10800
aaggactggc acgtctaggt gcgccttcac ccgagcggca tccgcgagtt caactgaaaa  10860
aagattctcg cgaggcgtat gtgccccaac agaacctatt tagagacaga agcggcgagg  10920
agccggagga gatgcgagct tcccgcttta acgcgggtcg tgagctgcgt cacggtttgg  10980
accgaagacg agtgttgcgg gacgaggatt tcgaagttga tgaaatgaca gggatcagtc  11040
ctgccagggc acacgtggct gcagccaacc ttgtatcggc ttacgagcag acagtaaagg  11100
aagagcgtaa cttccaaaag tcttttaata atcatgtgcg aaccctgatt gcccgcgaag  11160
aagttaccct tggtttgatg catttgtggg atttgatgaa agctatcatt cagaaccta  11220 ctagcaaacc tctgaccgcc cagctgtttc tggtggtgca acacagcaga gacaatgagg  11280 cttcagaga ggcgctgctg aacatcaccg aacccgaggg gagatggttg tatgatctta  11340
tcaacattct acagagtatc atagtgcagg agcggagcct gggcctggcc gagaaggtgg  11400
ctgccatcaa ttactcggtt ttgagcttgg gaaaatatta cgctcgcaaa atctacaaga  11460
ctccatacgt tcccatagac aaggaggtga agatagatgg gttctacatg cgcatgacgc  11520
tcaaggtctt gaccctgagc gatgatcttg gggtgtatcg caatgacaga atgcatcgcg  11580
cggttagcgc cagcaggagg cgcgagttaa gcgacaggga actgatgcac agtttgcaaa  11640
gagctctgac tggagctgga accgagggtg agaattactt cgacatggga gctgacttgc  11700
agtggcagcc tagtcgcagg gctctgagcg ccgcgacggc aggatgtgag cttccttaca  11760
tagaagaggc ggatgaaggc gaggaggaag agggcgagta cttggaagac tgatggcaca  11820
acccgtgttt tttgctagat ggaacagcaa gcaccggatc ccgcaatgcg ggcggcgctg  11880
cagagccagc cgtccggcat taactcctcg gacgattgga cccaggccat gcaacgtatc  11940
atggcgttga cgactcgcaa ccccgaagcc tttagacagc aaccccaggc caaccgtcta  12000
tcggccatca tggaagctgt agtgccttcc cgctctaatc ccactcatga gaaggtcctg  12060
gccatcgtga acgcgttggt ggagaacaaa gctattcgtc cagatgaggc cggactggta  12120
tacaacgctc tcttagaacg cgtggctcgc tacaacagta gcaatgtgca aaccaatttg  12180
gaccgtatga taacagatgt acgcgaagcc gtgtctcagc gcgaaaggtt ccagcgtgat  12240
gccaacctgg gttcgctggt ggcgttaaat gctttcttga gtactcagcc tgctaatgtg  12300
ccgcgtggtc aacaggatta tactaacttt ttaagtgctt tgagactgat ggtatcagaa  12360
gtacctcaga gcgaagtgta tcagtccggt cctgattact tctttcagac tagcagacag  12420
ggcttgcaga cggtaaatct gagccaagct tttaaaaacc tttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac cttttcattaa caaactgctg gactacttgc acagagctgc  12960
cgctatgaac tctgattatt tcaccaatgc catcttaaac ccgcactggc tgccccacc   13020 tggtttctac acgggcgaat atgacatgcc cgacccaat gacggatttc tgtgggacga  13080
cgtggacagc gatgttttt cacctctttc tgatcatcgc acgtggaaaa aggaaggcgg  13140
```

```
cgatagaatg cattcttctg catcgctgtc cggggtcatg ggtgctaccg cggctgagcc    13200
cgagtctgca agtccttttc ctagtctacc cttttctcta cacagtgtac gtagcagcga    13260
agtgggtaga ataagtcgcc cgagtttaat gggcgaagag gagtatctaa acgattcctt    13320
gctcagaccg gcaagagaaa aaaatttccc aaacaatgga atagaaagtt tggtggataa    13380
aatgagtaga tggaagactt atgctcagga tcacagagac gagcctggga tcatggggat    13440
tacaagtaga gcgagccgta gacgccagcg ccatgacaga cagaggggtc ttgtgtggga    13500
cgatgaggat tcggccgatg atagcagcgt gctggacttg ggtgggagag gaaggggcaa    13560
cccgtttgct catttgcgcc ctcgcttggg tggtatgttg taaaaaaaaa taaaaaaaaa    13620
actcaccaag gccatggcga cgagcgtacg ttcgttcttc tttattatct gtgtctagta    13680
taatgaggcg agtcgtgcta ggcggagcgg tggtgtatcc ggagggtcct cctccttcgt    13740
acgagagcgt gatgcagcag cagcaggcga cggcggtgat gcaatcccca ctggaggctc    13800
cctttgtgcc tccgcgatac ctggcaccta cggagggcag aaacagcatt cgttattcgg    13860
aactggcacc tcagtacgat accaccaggt tgtatctggt ggacaacaag tcggcggaca    13920
ttgcttctct gaactatcag aatgaccaca gcaacttctt gaccacggtg gtgcaaaaca    13980
atgactttac ccctacggaa gccagcaccc agaccattaa ctttgatgaa cgatcgcggt    14040
ggggcggtca gctaaagacc atcatgcata ctaacatgcc aaacgtgaac gagtatatgt    14100
ttagtaacaa gttcaaagcg cgtgtgatgg tgtccagaaa acctcccgac ggtgctgcag    14160
ttggggatac ttatgatcac aagcaggata ttttgaaata tgagtggttc gagtttactt    14220
tgccagaagg caacttttca gttactatga ctattgattt tgatgaacaat gccatcatag    14280 ataattactt gaaagtgggt agacagaatg gagtgcttga aagtgacatt ggtgttaagt    14340
tcgacaccag gaacttcaag ctgggatggg atcccgaaac caagttgatc atgcctggag    14400
tgtatacgta tgaagccttc catcctgaca ttgtcttact gcctggctgc ggagtggatt    14460
ttaccgagag tcgtttgagc aaccttcttg gtatcagaaa aaaacagcca tttcaagagg    14520
gttttaagat tttgtatgaa gatttagaag gtggtaatat tccggccctc ttggatgtag    14580
atgcctatga gaacagtaag aaagaacaaa aagccaaaat agaagctgct acagctgctg    14640
cagaagctaa ggcaaacata gttgccagcg actctacaag ggttgctaac gctggagagg    14700
tcagaggaga caattttgcg ccaacacctg ttccgactgc agaatcatta ttggccgatg    14760
tgtctgaagg aacggacgtg aaactcacta ttcaacctgt agaaaagat agtaagaata    14820 gaagctataa tgtgttggaa gacaaaatca acacagccta tcgcagttgg tatctttcgt    14880
acaattatgg cgatcccgaa aaaggagtgc gttcctggac attgctcacc acctcagatg    14940
tcacctgcgg agcagagcag gtctactggt cgcttccaga catgatgaag gatcctgtca    15000 cttttccgctc cactagacaa gtcagtaact acctgtggt gggtgcagag cttatgcccg    15060
tcttctcaaa gagcttctac aacgaacaag ctgtgtactc ccagcagctc cgccagtcca    15120
cctcgcttac gcacgtcttc aaccgcttc ctgagaacca gattttaatc cgtccgccgg    15180
cgcccaccat taccaccgtc agtgaaaacg ttcctgctct cacagatcac gggaccctgc    15240
cgttgcgcag cagtatccgg ggagtccaac gtgtgaccgt tactgacgcc agacgccgca    15300
cctgtcccta cgtgtacaag gcactgggca tagtcgcacc gcgcgtcctt tcaagccgca    15360 cttctaaaa aaaaaaaaaa tgtccattct tatctcgccc agtaataaca ccggttgggg    15420
tctgcgcgct ccaagcaaga tgtacggagg cgcacgcaaa cgttctaccc aacatcctgt    15480
```

```
ccgtgttcgc ggacattttc gcgctccatg gggcgccctc aagggccgca ctcgcgttcg   15540
aaccaccgtc gatgatgtaa tcgatcaggt ggttgccgac gcccgtaatt atactcctac   15600
tgcgcctaca tctactgtgg atgcagttat tgacagtgta gtggctgacg ctcgcaacta   15660
tgctcgacgt aagagccggc gaaggcgcat tgccagacgc caccgagcta ccactgccat   15720
gcgagccgca agagctctgc tacgaagagc tagacgcgtg gggcgaagag ccatgcttag   15780
ggcggccaga cgtgcagctt cgggcgccag cgccggcagg tcccgcaggc aagcagccgc   15840
tgtcgcagcg gcgactattg ccgacatggc ccaatcgcga agaggcaatg tatactgggt   15900
gcgtgacgct gccaccggtc aacgtgtacc cgtgcgcacc cgtcccccctc gcacttagaa   15960 gatactgagc agtctccgat gttgtgtccc agcggcgagg atgtccaagc gcaaatacaa   16020
ggaagaaatg ctgcaggtta tcgcacctga agtctacggc caaccgttga aggatgaaaa   16080
aaaaccccgc aaaatcaagc gggttaaaaa ggacaaaaaa gaagaggaag atggcgatga   16140
tgggctggcg gagtttgtgc gcgagtttgc cccacggcga cgcgtgcaat ggcgtgggcg   16200
caaagttcga catgtgttga gacctggaac ttcggtggtc tttacacccg gcgagcgttc   16260
aagcgctact tttaagcgtt cctatgatga ggtgtacggg gatgatgata ttcttgagca   16320
ggcggctgac cgattaggcg agtttgctta tggcaagcgt agtagaataa cttccaagga   16380
tgagacagtg tcgataccct tggatcatgg aaatcccacc cctagtctta aaccggtcac   16440
tttgcagcaa gtgttacccg taactccgcg aacaggtgtt aaacgcgaag gtgaagattt   16500
gtatcccact atgcaactga tggtacccaa acgccagaag ttggaggacg ttttggagaa   16560
agtaaaagtg gatccagata ttcaacctga ggttaaagtg agacccatta agcaggtagc   16620
gcctggtctg ggggtacaaa ctgtagacat taagattccc actgaaagta tggaagtgca   16680
aactgaaccc gcaaagccta ctgccacctc cactgaagtg caaacggatc catggatgcc   16740
catgcctatt acaactgacg ccgccggtcc cactcgaaga tcccgacgaa agtacggtcc   16800
agcaagtctg ttgatgccca attatgttgt acacccatct attattccta ctcctggtta   16860
ccgaggcact cgctactatc gcagccgaaa cagtacctcc cgccgtcgcc gcaagacacc   16920
tgcaaatcgc agtcgtcgcc gtagacgcac aagcaaaccg actcccggcg ccctggtgcg   16980
gcaagtgtac cgcaatggta gtgcggaacc tttgacactg ccgcgtgcgc gttaccatcc   17040
gagtatcatc acttaatcaa tgttgccgct gcctccttgc agatatggcc ctcacttgtc   17100
gccttcgcgt tcccatcact ggttaccgag gaagaaactc gcgccgtaga agagggatgt   17160
tgggacgcgg aatgcgacgc tacaggcgac ggcgtgctat ccgcaagcaa ttgcggggtg   17220
gttttttacc agccttaatt ccaattatcg ctgctgcaat tggcgcgata ccaggcatag   17280
cttccgtggc ggttcaggcc tcgcaacgac attgacattg aaaaaaacg tataaataaa   17340 aaaaaaaaaa tacaatggac tctgacactc ctggtcctgt gactatgttt tcttagagat   17400
ggaagacatc aattttttcat ccttggctcc gcgacacgc acgaagccgt acatgggcac   17460
ctggagcgac atcggcacga gccaactgaa cggggggcgcc ttcaattgga gcagtatctg   17520
gagcgggctt aaaaattttg gctcaaccat aaaaacatac gggaacaaag cttggaacag   17580
cagtacagga caggcgctta gaaataaact taaagaccag aacttccaac aaaaagtagt   17640
cgatgggata gcttccggca tcaatggagt ggtagatttg gctaaccagg ctgtgcagaa   17700
aaagataaac agtcgtttgg acccgccgcc agcaacccca ggtgaaatgc aagtggagga   17760
agaaattcct ccgccagaaa aacgaggcga caagcgtccg cgtcccgatt tggaagagac   17820
gctggtgacg cgcgtagatg aaccgccttc ttatgaggaa gcaacgaagc ttggaatgcc   17880
```

```
caccactaga ccgatagccc caatggccac cggggtgatg aaaccttctc agttgcatcg    17940
acccgtcacc ttggatttgc cccctccccc tgctgctact gctgtacccg cttctaagcc    18000
tgtcgctgcc ccgaaaccag tcgccgtagc caggtcacgt cccgggggcg ctcctcgtcc    18060
aaatgcgcac tggcaaaata ctctgaacag catcgtgggt ctaggcgtgc aaagtgtaaa    18120
acgccgtcgc tgcttttaat taaatatgga gtagcgctta acttgccta t ctgtgtatat    18180 gtgtcattac acgccgtcac agcagcagag gaaaaaagga agaggtcgtg cgtcgacgct    18240
gagttacttt caagatggcc accccatcga tgctgcccca atgggcatac atgcacatcg    18300
ccggacagga tgcttcggag tacctgagtc cgggtctggt gcagttcgcc cgcgccacag    18360
acacctactt caatctggga aataagttta gaaatcccac cgtagcgccg acccacgatg    18420
tgaccaccga ccgtagccag cggctcatgt tgcgcttcgt gcccgttgac cgggaggaca    18480
atacatactc ttacaaagtg cggtacaccc tggccgtggg cgacaacaga gtgctggata    18540
tggccagcac gttctttgac attaggggtg tgttggacag aggtcccagt ttcaaaccct    18600
attctggtac ggcttacaac tccctggctc ctaaaggcgc tccaaataca tctcagtgga    18660
ttgcagaagg tgtaaaaaat acaactggtg aggaacacgt aacagaagag gaaaccaata    18720
ctactactta cacttttggc aatgctcctg taaaagctga agctgaaatt acaaaagaag    18780
gactcccagt aggtttggaa gtttcagatg aagaaagtaa accgatttat gctgataaaa    18840
catatcagcc agaacctcag ctgggagatg aaacttggac tgaccttgat ggaaaaaccg    18900
aaaagtatgg aggcagggct ctcaaacccg atactaagat gaaaccatgc tacgggtcct    18960
ttgccaaacc tactaatgtg aaaggcggtc aggcaaaaca aaaaacaacg gagcagccaa    19020
atcagaaagt cgaatatgat atcgacatgg agttttttga tgcggcatcg cagaaaacaa    19080
acttaagtcc taaaattgtc atgtatgcag aaaatgtaaa tttggaaact ccagacactc    19140
atgtagtgta caaacctgga acagaagaca caagttccga agctaatttg ggacaacaat    19200
ctatgcccaa cagacccaac tacattggct tcagagataa ctttattgga cttatgtact    19260
ataacagtac tggtaacatg ggggtgctgg ctggtcaagc gtctcagtta aatgcagtgg    19320
ttgacttgca ggacagaaac acagaacttt cttaccaact cttgcttgac tctctgggcg    19380
acagaaccag atacttagc atgtggaatc aggctgtgga cagttatgat cctgatgtac    19440
gtgttattga aaatcatggt gtggaagatg aacttcccaa ctactgtttt ccactggacg    19500
gcataggtgt tccaacaacc agttacaaat caatagttcc aaatggagac aatgcgccta    19560
attggaagga acctgaagta aatggaacaa gtgagatcgg acagggtaat ttgtttgcca    19620
tggaaattaa ccttcaagcc aatctatggc gaagtttcct ttattccaat gtggctctat    19680
atctcccaga ctcgtacaaa tacaccccgt ccaatgtcac tcttccagaa aacaaaaaca    19740
cctacgacta catgaacggg cgggtggtgc cgccatctct agtagacacc tatgtgaaca    19800
ttggtgccag gtggtctctg gatgccatgg acaatgtcaa cccattcaac caccaccgta    19860
acgctggctt gcgttaccga tccatgcttc tgggtaacgg acgttatgtg cctttccaca    19920
tacaagtgcc tcaaaaattc ttcgctgtta aaaacctgct gcttctccca ggctcctaca    19980
cttatgagtg gaactttagg aaggatgtga acatggttct acagagttcc ctcggtaacg    20040
acctgcgggt agatggcgcc agcatcagtt tcacgagcat caacctctat gctacttttt    20100
tccccatggc tcacaacacc gcttccaccc ttgaagccat gctgcggaat gacaccaatg    20160
atcagtcatt caacgactac ctatctgcag ctaacatgct ctaccccatt cctgccaatg    20220
```

```
caaccaatat tcccatttcc attccttctc gcaactgggc ggctttcaga ggctggtcat   20280
ttaccagact gaaaaccaaa gaaactccct ctttggggtc tggatttgac ccctactttg   20340
tctattctgg ttctattccc tacctggatg gtaccttcta cctgaaccac acttttaaga   20400
aggtttccat catgtttgac tcttcagtga gctggcctgg aaatgacagg ttactatctc   20460
ctaacgaatt tgaaataaag cgcactgtgg atggcgaagg ctacaacgta gcccaatgca   20520
acatgaccaa agactggttc ttggtacaga tgctcgccaa ctacaacatc ggctatcagg   20580
gcttctacat tccagaagga tacaaagatc gcatgtattc attttcaga aacttccagc   20640
ccatgagcag gcaggtggtt gatgaggtca attacaaaga cttcaaggcc gtcgccatac   20700
cctaccaaca caacaactct ggctttgtgg gttacatggc tccgaccatg cgccaaggtc   20760
aaccctatcc cgctaactat ccctatccac tcattgaaac aactgccgta aatagtgtta   20820
cgcagaaaaa gttcttgtgt gacagaacca tgtggcgcat accgttctcg agcaacttca   20880
tgtctatggg ggcccttaca gacttgggac agaatatgct ctatgccaac tcagctcatg   20940
ctctggacat gacctttgag gtggatccca tggatgagcc caccctgctt tatcttctct   21000
tcgaagtttt cgacgtggtc agagtgcatc agccacaccg cggcatcatc gaggcagtct   21060
acctgcgtac accgttctcg gccggtaacg ctaccacgta agaagcttct tgcttcttgc   21120
aaatagcagc tgcaaccatg gcctgcggat cccaaaacgg ctccagcgag caagagctca   21180
gagccattgt ccaagacctg ggttgcggac ctatttttt gggaacctac gataagcgct   21240
tcccgggggtt catggccccc gataagctcg cctgtgccat tgtaaatacg gccggacgtg   21300
agacgggggg agagcactgg ttggctttcg gttggaaccc acgttctaac acctgctacc   21360
tttttgatcc ttttggattc tcggatgatc gtctcaaaca gatttaccag tttgaatatg   21420
agggtctcct gcgccgcagc gctcttgcta ccaaggaccg ctgtattacg ctggaaaaat   21480
ctacccagac cgtgcagggt ccccgttctg ccgcctgcgg acttttctgc tgcatgttcc   21540
ttcacgcctt tgtgcactgg cctgaccgtc ccatggacgg aaaccccacc atgaaattgc   21600
taactggagt gccaaacaac atgcttcatt ctcctaaagt ccagcccacc ctgtgtgaca   21660
atcaaaaagc actctaccat tttcttaata cccattcgcc ttattttcgc tcccatcgta   21720
cacacatcga aagggccact cgttcgacc gtatggatgt tcaataatga ctcatgtaaa   21780
caacgtgttc aataaacatc actttatttt tttacatgta tcaaggctct gcattactta   21840
tttatttaca agtcgaatgg gttctgacga gaatcagaat gacccgcagg cagtgatacg   21900
ttgcggaact gatacttggg ttgccacttg aattcgggaa tcaccaactt gggaaccggt   21960
atatcgggca ggatgtcact ccacagcttt ctggtcagct gcaaagctcc aagcaggtca   22020
ggagccgaaa tcttgaaatc acaattagga ccagtgcttt gagcgcgaga gttgcggtac   22080
accggattgc agcactgaaa caccatcagc gacggatgtc tcacgcttgc cagcacggtg   22140
ggatctgcaa tcatgcccac atccagatct tcagcattgg caatgctgaa cggggtcatc   22200
ttgcaggtct gcctacccat ggcgggcacc caattaggct tgtggttgca atcgcagtgc   22260
agggggatca gtatcatctt ggcctgatcc tgtctgattc ctggatacac ggctctcatg   22320
aaagcatcat attgcttgaa agcctgctgg gctttactac cctcggtata aacatcccg   22380
caggacctgc tcgaaaactg gttagctgca cagccggcat cattcacaca gcagcgggcg   22440
tcattgttag ctatttgcac cacacttctg ccccagcggt tttgggtgat tttggttcgc   22500
tcgggattcc cctttaaggc tcgttgtccg ttctcgctgg ccacatccat ctcgataatc   22560
tgctccttct gaatcataat attgccatgc aggcacttca gcttgccctc ataatcattg   22620
```

```
cagccatgag gccacaacgc acagcctgta cattcccaat tatggtgggc gatctgagaa   22680
aaagaatgta tcattccctg cagaaatctt cccatcatcg tgctcagtgt cttgtgacta   22740
gtgaaagtta actggatgcc tcggtgctcc tcgtttacgt actggtgaca gatgcgcttg   22800
tattgttcgt gttgctcagg cattagttta aagaggttc taagttcgtt atccagcctg    22860
tacttctcca tcagcagaca catcacttcc atgcctttct cccaagcaga caccaggggc   22920
aagctaatcg gattcttaac agtgcaggca gcagctcctt tagccagagg gtcatcttta   22980
gcgatcttct caatgcttct tttgccatcc ttctcaacga tgcgcacggg cgggtagctg   23040
aaacccactg ctacaagttg cgcctcttct ctttcttctt cgctgtcttg actgatgtct   23100
tgcatgggga tatgtttggt cttccttggc ttcttttgg ggggtatcgg aggaggagga    23160
ctgtcgctcc gttccggaga cagggaggat tgtgacgttt cgctcaccat taccaactga   23220
ctgtcggtag aagaacctga ccccacacgc cgacaggtgt ttctcttcgg ggcagaggt    23280 ggaggcgatt gcgaagggct gcggtccgac ctggaaggcg gatgactggc agaacccctt   23340
ccgcgttcgg gggtgtgctc cctgtggcgg tcgcttaact gatttccttc gcggctggcc   23400
attgtgttct cctaggcaga gaaacaacag acatggaaac tcagccattg ctgtcaacat   23460
cgccacgagt gccatcacat ctcgtcctca gcgacgagga aaaggagcag agcttaagca   23520
ttccaccgcc cagtcctgcc accacctcta ccctagaaga taaggaggtc gacgcatctc   23580
atgacatgca gaataaaaaa gcgaaagagt ctgagacaga catcgagcaa gacccgggct   23640
atgtgacacc ggtggaacac gaggaagagt tgaaacgctt tctagagaga gaggatgaaa   23700
actgcccaaa acaacgagca gataactatc accaagatgc tggaaatagg gatcagaaca   23760
ccgactacct cataggggctt gacggggaag acgcgctcct taaacatcta gcaagacagt   23820
cgctcatagt caaggatgca ttattggaca gaactgaagt gcccatcagt gtggaagagc   23880
tcagccgcgc ctacgagctt aacctctttt cacctcgtac tccccccaaa cgtcagccaa   23940
acggcacctg cgagccaaat cctcgcttaa acttttatcc agcttttgct gtgccagaag   24000
tactggctac ctatcacatc ttttttaaaa atcaaaaaat tccagtctcc tgccgcgcta   24060
atcgcacccg cgccgatgcc ctactcaatc tgggacctgg ttcacgctta cctgatatag   24120
cttccttgga agaggttcca aagatcttcg agggtctggg caataatgag actcgggccg   24180
caaatgctct gcaaaaggga gaaaatggca tggatgagca tcacagcgtt ctggtggaat   24240
tggaaggcga taatgccaga ctcgcagtac tcaagcgaag catcgaggtc acacacttcg   24300
catatcccgc tgtcaacctg cccctaaag tcatgacggc ggtcatggac cagttactca    24360
ttaagcgcgc aagtcccctt tcagaagaca tgcatgaccc agatgcctgt gatgagggta   24420
aaccagtggt cagtgatgag cagctaaccc gatggctggg caccgactct cccagggatt   24480
tggaagagcg tcgcaagctt atgatggccg tggtgctggt taccgtagaa ctagagtgtc   24540
tccgacgttt ctttaccgat tcagaaacct tgcgcaaact cgaagagaat ctgcactaca   24600 ctttttagaca cggctttgtg cggcaggcat gcaagatatc taacgtggaa ctcaccaacc   24660
tggtttccta catgggtatt ctgcatgaga atcgcctagg acaaagcgtg ctgcacagca   24720
ccctgaaggg ggaagcccgc cgtgattaca tccgcgattg tgtctatctg tacctgtgcc   24780
acacgtggca aaccggcatg ggtgtatggc agcaatgttt agaagaacag aacttgaaag   24840
agcttgacaa gctcttacag aaatctctta aggttctgtg acagggttc gacgagcgca    24900 ccgtcgcttc cgacctggca gacctcatct tcccagagcg tctcagggtt actttgcgaa   24960
```

| | |
|---|---|
| acggattgcc tgactttatg agccagagca tgcttaacaa ttttcgctct ttcatcctgg | 25020 |
| aacgctccgg tatcctgccc gccacctgct gcgcactgcc ctccgacttt gtgcctctca | 25080 |
| cctaccgcga gtgcccccg ccgctatgga gtcactgcta cctgttccgt ctggccaact | 25140 |
| atctctccta ccactcggat gtgatcgagg atgtgagcgg agacggcttg ctggagtgtc | 25200 |
| actgccgctg caatctgtgc acgccccacc ggtccctagc ttgcaacccc cagttgatga | 25260 |
| gcgaaaccca gataataggc acctttgaat tgcaaggccc cagcagccaa ggcgatgggt | 25320 |
| cttctcctgg gcaaagttta aaactgaccc cgggactgtg gacctccgcc tacttgcgca | 25380 |
| agtttgctcc ggaagattac cacccctatg aaatcaagtt ctatgaggac caatcacagc | 25440 |
| ctccaaaggc cgaactttcg gcctgcgtca tcacccaggg ggcaattctg gcccaattgc | 25500 |
| aagccatcca aaaatcccgc caagaatttc tactgaaaaa gggtaagggg gtctaccttg | 25560 |
| accccagac cggcgaggaa ctcaacacaa ggttccctca ggatgtccca acgacgagaa | 25620 |
| aacaagaagt tgaaggtgca gccgccgccc ccagaagata tggaggaaga ttgggacagt | 25680 |
| caggcagagg aggcggagga ggacagtctg gaggacagtc tggaggaaga cagtttggag | 25740 |
| gaggaaaacg aggaggcaga ggaggtggaa gaagtaaccg ccgacaaaca gttatcctcg | 25800 |
| gctgcggaga caagcaacag cgctaccatc tccgctccga gtcgaggaac ccggcggcgt | 25860 |
| cccagcagta gatgggacga gaccggacgc ttcccgaacc caaccagcgc ttccaagacc | 25920 |
| ggtaagaagg atcggcaggg atacaagtcc tggcggggc ataagaatgc catcatctcc | 25980 |
| tgcttgcatg agtgcggggg caacatatcc ttcacgcggc gctacttgct attccaccat | 26040 |
| ggggtgaact ttccgcgcaa tgttttgcat tactaccgtc acctccacag cccctactat | 26100 |
| agccagcaaa tcccggcagt ctcgacagat aaagacagcg gcggcgacct caacagaaa | 26160 |
| accagcagcg gcagttagaa aatacacaac aagtgcagca acaggaggat taaagattac | 26220 |
| agccaacgag ccagcgcaaa cccgagagtt aagaaatcgg atctttccaa ccctgtatgc | 26280 |
| catcttccag cagagtcggg gtcaagagca ggaactgaaa ataaaaaacc gatctctgcg | 26340 |
| ttcgctcacc agaagttgtt tgtatcacaa gagcgaagat caacttcagc gcactctcga | 26400 |
| ggacgccgag gctctcttca acaagtactg cgcgctgact cttaaagagt aggcagcgac | 26460 |
| cgcgcttatt caaaaaaggc gggaattaca tcatcctcga catgagtaaa gaaattccca | 26520 |
| cgccttacat gtggagttat caaccccaaa tgggattggc ggcaggcgcc tcccaggact | 26580 |
| actccacccg catgaattgg ctcagcgccg ggccttctat gatttctcga gttaatgata | 26640 |
| tacgcgccta ccgaaaccaa atacttttgg aacagtcagc tcttaccacc acgccccgcc | 26700 |
| aacaccttaa tcccagaaat tggcccgccg ccctagtgta ccaggaaagt cccgctccca | 26760 |
| ccactgtatt acttcctcga gacgcccagg ccgaagtcca aatgactaat gcaggtgcgc | 26820 |
| agttagctgg cggctccacc ctatgtcgtc acaggcctcg gcataatata aaacgcctga | 26880 |
| tgatcagagg ccgaggtatc cagctcaacg acgagtcggt gagctctccg cttggtctac | 26940 |
| gaccagacgg aatctttcag attgccggct gcgggagatc ttccttcacc cctcgtcagg | 27000 |
| ctgttctgac tttggaaagt tcgtcttcgc aaccccgctc gggcggaatc gggaccgttc | 27060 |
| aatttgtgga ggagtttact ccctctgtct acttcaaccc cttctccgga tctcctgggc | 27120 |
| attcccgga cgagttcata ccgaacttcg acgcgattag cgagtcagtg gacggctacg | 27180 |
| attgatgtct ggtgacgcgg ctgagctatc tcggctgcga catctagacc actgccgccg | 27240 |
| ctttcgctgc tttgcccggg aactcattga gttcatctac ttcgaactcc caaggatca | 27300 |
| ccctcaaggt ccggcccacg gagtgcggat ttctatcgaa ggcaaaatag actctcgcct | 27360 |

```
gcaacgaatt ttctcccagc ggcccgtgct gatcgagcga gaccagggaa acaccacggt    27420
ttccatctac tgcatttgta atcaccccgg attgcatgaa agcctttgct gtcttatgtg    27480
tactgagttt aataaaaact gaattaagac tctcctacgg actgccgctt cttcaacccg    27540
gattttacaa ccagaagaac gaaactttc ctgtcgtcca ggactctgtt aacttcacct     27600
ttcctactca caaactagaa gctcaacgac tacaccgctt ttccagaagc attttcccta    27660
ctaatactac tttcaaaacc ggaggtgagc tccaaggtct tcctacagaa aacccttggg    27720
tggaagcggg ccttgtagtg ctaggaattc ttgcgggtgg gcttgtgatt attctttgct    27780
acctatacac accttgcttc actttcttag tggtgttgtg gtattggttt aaaaaatggg    27840
gcccatacta gtcttgcttg ttttactttc gcttttggaa ccgggttctg ccaattacga    27900
tccatgtcta gacttcgacc cagaaaactg cacacttact tttgcacccg acacaagccg    27960
catctgtgga gttcatcgcc tctcttacga acttggcccc caacgacaaa atttacctg     28020 catggtggga atcaaccccca tagttatcac ccagcaaagt ggagatacta agggttgcat   28080
tcactgctcc tgcgattcca tcgagtgcac ctacaccctg ctgaagaccc tatgcggcct    28140
aagagacctg ctaccaatga attaaaaaat gattaataaa aaatcactta cttgaaatca    28200
gcaataaggt tctgttgaa atttttctccc agcagcacct cacttccctc ttcccaactc    28260
tggtattcta aaccccgttc agcggcatac tttctccata ctttaaaggg gatgtcaaat    28320
tttagctcct ctcctgtacc cacaatcttc atgtctttct tcccagatga ccaagagagt    28380
ccggctcagt gactccttca accctgtcta cccctatgaa gatgaaagca cctcccaaca    28440 ccccttttata aacccagggt ttatttcccc aaatggcttc acacaaagcc caaacggagt   28500
tcttacttta aaatgtttaa ccccactaac aaccacaggc ggatctctac agctaaaagt    28560
gggaggggga cttacagtgg atgacaccaa cggttttttg aaagaaaaca taagtgccac    28620
cacaccactc gttaagactg gtcactctat aggtttacca ctaggagccg gattgggaac    28680
gaatgaaaat aaactttgta tcaaattagg acaaggactt acattcaatt caaacaacat    28740
ttgcattgat gacaatatta acccttatg acaggagtc aacccccaccg aagccaactg     28800 tcaaatcatg aactccagtg aatctaatga ttgcaaatta attctaacac tagttaaaac    28860
tggagcacta gtcactgcat ttgtttatgt tataggagta tctaacaatt ttaatatgct    28920
aactacacac agaaatataa attttactgc agagctgttt ttcgattcta ctggtaattt    28980
actaactaga ctctcatccc tcaaaactcc acttaatcat aaatcaggac aaaacatggc    29040
tactggtgcc attactaatg ctaaaggttt catgcccagc acgactgcct atccttcaa     29100 tgataattct agagaaaaag aaaactacat ttacggaact tgttactaca cagctagtga    29160
tcgcactgct tttcccattg acatatctgt catgcttaac cgaagagcaa taaatgacga    29220
gacatcatat tgtattcgta taacttggtc ctggaacaca ggagatgccc cagaggtgca    29280
aacctctgct acaacccctag tcacctcccc atttaccttt tactacatca gagaagacga    29340
ctgacaaata aagtttaact tgtttatttg aaaatcaatt cacaaaatcc gagtagttat    29400
tttgcctccc ccttcccatt taacagaata caccaatctc tccccacgca cagctttaaa    29460
catttggata ccattagata tagacatggt tttagattcc acattccaaa cagtttcaga    29520
gcgagccaat ctggggtcag tgatagataa aaatccatcg ggatagtctt ttaaagcgct    29580
ttcacagtcc aactgctgcg gatgcgactc cggagtctgg atcacggtca tctggaagaa    29640
gaacgatggg aatcataatc cgaaaacggt atcggacgat tgtgtctcat caaacccaca    29700
```

```
agcagccgct gtctgcgtcg ctccgtgcga ctgctgttta tgggatcagg gtccacagtg   29760
tcctgaagca tgatttttaat agcccttaac atcaactttc tggtgcgatg cgcgcagcaa   29820
cgcattctga tttcactcaa atctttgcag taggtacaac acattattac aatattgttt   29880
aataaaccat aattaaaagc gctccagcca aaactcatat ctgatataat cgcccctgca   29940
tgaccatcat accaaagttt aatataaatt aaatgacgtt ccctcaaaaa cacactaccc   30000
acatacatga tctcttttgg catgtgcata ttaacaatct gtctgtacca tggacaacgt   30060
tggttaatca tgcaacccaa tataaccttc cggaaccaca ctgccaacac cgctccccca   30120
gccatgcatt gaagtgaacc ctgctgatta caatgacaat gaagaaccca attctctcga   30180
ccgtgaatca cttgagaatg aaaaatatct atagtggcac aacatagaca taaatgcatg   30240
catcttctca taattttttaa ctcctcagga tttagaaaca tatcccaggg aataggaagc   30300
tcttgcagaa cagtaaagct ggcagaacaa ggaagaccac gaacacaact tacactatgc   30360
atagtcatag tatcacaatc tggcaacagc gggtggtctt cagtcataga agctcgggtt   30420
tcattttcct cacaacgtgg taactgggct ctggtgtaag ggtgatgtct ggcgcatgat   30480
gtcgagcgtg cgcgcaacct tgtcataatg gagttgcttc ctgacattct cgtattttgt   30540
atagcaaaac gcggccctgg cagaacacac tcttcttcgc cttctatcct gccgcttagc   30600
gtgttccgtg tgatagttca agtacaacca cactcttaag ttggtcaaaa gaatgctggc   30660
ttcagttgta atcaaaactc catcgcatct aatcgttctg aggaaatcat ccaagcaatg   30720
caactggatt gtgtttcaag caggagagga gagggaagag acggaagaac catgttaatt   30780
tttattccaa acgatctcgc agtacttcaa attgtagatc gcgcagatgg catctctcgc   30840
ccccactgtg ttggtgaaaa agcacagcta gatcaaaaga aatgcgattt tcaaggtgct   30900
caacggtggc ttccagcaaa gcctccacgc gcacatccaa gaacaaaaga ataccaaaag   30960
aaggagcatt ttctaactcc tcaatcatca tattacattc ctgcaccatt cccagataat   31020
tttcagcttt ccagccttga attattcgtg tcagttcttg tggtaaatcc aatccacaca   31080
ttacaaacag gtcccggagg gcgccctcca ccaccattct taaacacacc ctcataatga   31140
caaaatatct tgctcctgtg tcacctgtag cgaattgaga atggcaacat caattgacat   31200
gcccttggct ctaagttctt ctttaagttc tagttgtaaa aactctctca tattatcacc   31260
aaactgctta gccagaagcc ccccgggaac aagagcaggg gacgctacag tgcagtacaa   31320
gcgcagacct ccccaattgg ctccagcaaa aacaagattg gaataagcat attgggaacc   31380
gccagtaata tcatcgaagt tgctggaaat ataatcaggc agagtttctt gtaaaaattg   31440
aataaaagaa aaatttgcca aaaaaacatt caaaacctct gggatgcaaa tgcaataggt   31500
taccgcgctg cgctccaaca ttgttagttt tgaattagtc tgcaaaaata aaaaaaaaaa   31560
caagcgtcat atcatagtag cctgacgaac agatggataa atcagtcttt ccatcacaag   31620
acaagccaca gggtctccag ctcgaccctc gtaaaacctg tcatcatgat taaacaacag   31680
caccgaaagt tcctcgcggt gaccagcatg aataattctt gatgaagcat acaatccaga   31740
catgttagca tcagttaacg agaaaaaaca gccaacatag cctttgggta taattatgct   31800
taatcgtaag tatagcaaag ccaccctcg cggatacaaa gtaaaaggca caggagaata   31860
aaaaatataa ttatttctct gctgctgttc aggcaacgtc gccccccgtc cctctaaata   31920
cacatacaaa gcctcatcag ccatggctta ccagacaaag tacagcgggc acacaaagca   31980
caagctctaa agtgactctc caacctctcc acaatatata tatacacaag ccctaaactg   32040
acgtaatggg agtaaagtgt aaaaaatccc gccaaaccca acacacaccc cgaaactgcg   32100
```

```
tcaccaggga aaagtacagt ttcacttccg caatcccaac aggcgtaact tcctctttct    32160
cacggtacgt gatatcccac taacttgcaa cgtcattttc ccacggtcgc accgcccctt    32220
ttagccgtta accccacagc caatcaccac acgatccaca cttttaaaa tcacctcatt     32280 tacatattgg caccattcca tctataaggt atattatata gatag                    32325
```

<210> SEQ ID NO 2
<211> LENGTH: 34794
<212> TYPE: DNA
<213> ORGANISM: Adenovirus

<400> SEQUENCE: 2

```
ctatctatat aatataccrtt atagatggaa tggtgccaat atgtaaatga ggtgatttta      60
aaaagtgtgg atcgtgtggt gattggctgt ggggttaacg gctaaaaggg gcggtgcgac     120
cgtgggaaaa tgacgttttg tggggggtgga gttttttttgc aagttgtcgc gggaaatgtg    180
acgcataaaa aggcttttt ctcacggaac tacttagttt tcccacggta tttaacagga      240
aatgaggtag ttttgaccgg atgcaagtga aaattgttga ttttcgcgcg aaaactgaat     300
gaggaagtgt ttttctgaat aatgtggtat ttatggcagg gtggagtatt tgttcagggc     360
caggtagact ttgacccatt acgtggaggt ttcgattacc gtgttttta cctgaatttc      420 cgcgtaccgt gtcaaagtct tctgttttta cgtaggtgtc agctgatcgc tagggtattt     480
atacctcagg gtttgtgtca agaggccact cttgagtgcc agcgagaaga gttttctcct     540
ctgcgccggc agtttaataa taaaaaatg agagatttgc gatttctgcc tcaggaaata     600
atctctgctg agactggaaa tgaaatattg gagcttgtgg tgcacgccct gatgggagac     660
gatccggagc cacctgtgca gcttttgag cctcctacgc ttcaggaact gtatgattta      720
gaggtagagg gatcggagga ttctaatgag gaagctgtaa atggcttttt taccgattct     780
atgcttttag ctgctaatga agggttagaa ttagatccgc ctttggacac ttttgatact     840
ccaggggtaa ttgtggaaag cggtacaggt gtaagaaaat tacctgattt gagttccgtg     900
gactgtgatt tgcactgcta tgaagacggg tttcctccga gtgatgagga ggaccatgaa     960
aaggagcagt ccatgcagac tgcagcgggt gagggagtga aggctgccaa tgttggtttt    1020
cagttggatt gcccggagct tcctggacat ggctgtaagt cttgtgaatt tcacaggaaa    1080
aatactggag taaaggaact gttatgttcg ctttgttata tgagaacgca ctgccacttt    1140
atttacagta agtgtgttta agttaaaatt taaggaata tgctgttttt cacatgtata    1200
ttgagtgtga gttttgtgct tcttattata ggtcctgtgt ctgatgctga tgaatcacca    1260
tctcctgatt ctactacctc acctcctgag attcaagcac ctgttcctgt ggacgtgcgc    1320
aagcccattc ctgtgaagct taagcctggg aaacgtccag cagtggaaaa acttgaggac    1380
ttgttacagg gtgggacgg acctttggac ttgagtacac ggaaacgtcc aagacaataa    1440
gtgttccata tccgtgttta cttaaggtga cgtcaatatt tgtgtgacag tgcaatgtaa    1500
taaaaatatg ttaactgttc actggttttt attgcttttt gggcggggac tcaggtatat    1560
aagtagaagc agacctgtgt ggttagctca taggagctgg ctttcatcca tggaggtttg    1620
ggccattttg gaagacctta ggaagactag gcaactgtta gagaacgctt cggacggagt    1680
ctccggtttt tggagattct ggttcgctag tgaattagct agggtagttt ttaggataaa    1740
acaggactat aaacaagaat ttgaaaagtt gttggtagat tgcccaggac tttttgaagc    1800
tcttaatttg ggccatcagg ttcactttaa agaaaaagtt ttatcagttt tagactttc     1860
```

```
aaccccaggt agaactgctg ctgctgtggc ttttcttact tttatattag ataaatggat    1920
cccgcagact catttcagca ggggatacgt tttggatttc atagccacag cattgtggag    1980
aacatggaag gttcgcaaga tgaggacaat cttaggttac tggccagtgc agcctttggg    2040
tgtagcggga atcctgaggc atccaccggt catgccagcg gttctggagg aggaacagca    2100
agaggacaac ccgagagccg gcctggaccc tccagtggag gaggcggagt agctgacttg    2160
tctcctgaac tgcaacgggt gcttactgga tctacgtcca ctggacggga taggggcgtt    2220
aagagggaga gggcatctag tggtactgat gctagatctg agttggcttt aagtttaatg    2280
agtcgcagac gtcctgaaac catttggtgg catgaggttc agaaagaggg aagggatgaa    2340
gtttctgtat tgcaggagaa atattcactg gaacaggtga aaacatgttg gttggagcct    2400
gaggatgatt gggaggtggc cattaaaaat tatgccaaga tagctttgag gcctgataaa    2460
cagtataaga ttactagacg gattaatatc cggaatgctt gttacatatc tggaaatggg    2520
gctgaggtgg taatagatac tcaagacaag gcagttatta gatgctgcat gatggatatg    2580
tggcctgggg tagtcggtat ggaagcagta acttttgtaa atgttaagtt tagggagat    2640 ggttataatg gaatagtgtt tatggccaat accaaactta tattgcatgg ttgtagcttt    2700
tttggtttca acaatacctg tgtagatgcc tggggacagg ttagtgtacg gggatgtagt    2760
ttctatgcgt gttggattgc cacagctggc agaaccaaga gtcaattgtc tctgaagaaa    2820
tgcatatttc aaagatgtaa cctgggcatt ctgaatgaag gcgaagcaag ggtccgccac    2880
tgcgcttcta cagatactgg atgttttatt ttgattaagg gaaatgccag cgtaaagcat    2940
aacatgattt gcggtgcttc cgatgagagg cctatcaaa tgctcacttg tgctggtggg    3000
cattgtaata tgctggctac tgtgcatatt gtttcccatc aacgcaaaaa atggcctgtt    3060
tttgatcaca atgtgatgac gaagtgtacc atgcatgcag gtgggcgtag aggaatgttt    3120
atgccttacc agtgtaacat gaatcatgtg aaagtgttgt tggaaccaga tgccttttcc    3180
agaatgagcc taacaggaat ttttgacatg aacatgcaaa tctggaagat cctgaggtat    3240
gatgatacga gatcgagggt acgcgcatgc gaatgcggag gcaagcatgc caggttccag    3300
ccggtgtgtg tagatgtgac tgaagatctc agaccggatc atttggttat tgcccgcact    3360
ggagcagagt tcggatccag tggagaagaa actgactaag gtgagtattg ggaaaacttt    3420
ggggtgggat tttcagatgg acagattgag taaaaatttg ttttttctgt cttgcagctg    3480
tcatgagtgg aaacgcttct tttaaggggg gagtcttcag cccttatctg acagggcgtc    3540
tcccatcctg ggcaggagtt cgtcagaatg ttatgggatc tactgtggat ggaagacccg    3600
tccaacccgc caattcttca acgctgacct atgctacttt aagttcttca cctttggacg    3660
cagctgcagc tgccgccgcc gcttctgttg ccgctaacac tgtgcttgga atgggttact    3720
atggaagcat catggctaat tccacttcct ctaataaccc ttctaccctg actcaggaca    3780
agttacttgt ccttttggcc cagctggagg ctttgaccca acgtctgggt gaactttctc    3840
agcaggtggt cgagttgcga gtacaaactg agtctgctgt cggcacggca agtctaaat    3900 aaaaaaatcc cagaatcaat gaataaataa acaagcttgt tgttgattta aaatcaagtg    3960 ttttatttc attttcgcg cacggtatgc cctagaccac cgatctctat cattgagaac    4020
tcggtggatt ttttccagga tcctatagag gtgggattga atgtttagat acatgggcat    4080
taggccgtct ttggggtgga gatagctcca ttgaagggat tcatgctccg gggtagtgtt    4140
gtaaatcacc cagtcataac aaggtcgcag tgcatggtgt tgcacaatat cttttagaag    4200
taggctgatt gccacagata agcccttggt gtaggtgttt acaaaccggt tgagctggga    4260
```

```
tgggtgcatt cggggtgaaa ttatgtgcat tttggattgg atttttaagt tggcaatatt    4320
gccgccaaga tcccgtcttg ggttcatgtt atgaaggacc accaagacgg tgtatccggt    4380
acatttagga aatttatcgt gcagcttgga tggaaaagcg tggaaaaatt tggagacacc    4440
cttgtgtcct ccaagatttt ccatgcactc atccatgata atagcaatgg gccgtgggc     4500
agcggcgcgg gcaaacacgt tccgtgggtc tgacacatca tagttatgtt cctgagttaa    4560
atcatcataa gccattttaa tgaatttggg gcggagagta ccagattggg gtatgaatgt    4620
tccttcgggc cccggagcat agttcccctc acagatttgc atttcccaag ctttcagttc    4680
cgagggtgga atcatgtcca cctggggggc tatgaaaaac accgtttctg gggcggggt     4740
gattaattgt gatgatagca aatttctgag caattgagat ttgccacatc cggtggggcc    4800
ataaatgatt ccgattacgg gttgcaggtg gtagtttagg aacggcaac tgccgtcttc     4860
tcgaagcaag ggggccacct cgttcatcat ttcccttaca tgcatatttt cccgcaccaa    4920
atccattagg aggcgctctc ctcctagtga tagaagttct tgtagtgagg aaaagttttt    4980
cagcggtttc agaccgtcag ccatgggcat tttggagaga gtttgctgca aaagttctag    5040
tctgttccac agttcagtga tgtgttctat ggcatctcga tccagcagac ctcctcgttt    5100
cgcgggtttg gacggctcct ggaatagggt atgagacgat gggcgtccag cgctgccagg    5160
gttcggtcct tccagggtct cagtgttcga gtcagggttg tttccgtcac agtgaagggg    5220
tgtgcgcctg cttgggcgct tgccagggtg cgcttcagac tcatcctgct ggtcgaaaac    5280
ttctgtcgct tggcgccctg tatgtcggcc aagtagcagt ttaccatgag ttcgtagttg    5340
agcgcctcgg ctgcgtggcc tttggcgcgg agcttacctt tggaagtttt cttgcatacc    5400
gggcagtata ggcatttcag cgcatacaac ttgggcgcaa ggaaacgga ttctggggag     5460
tatgcatctg cgccgcagga ggcgcaaaca gtttcacatt ccaccagcca ggttaaatcc    5520
ggttcattgg ggtcaaaaac aagttttccg ccatattttt tgatgcgttt cttacctttg    5580
gtctccatga gttcgtgtcc tcgttgagtg acaaacaggc tgtccgtgtc cccgtagact    5640
gattttacag gcctcttctc cagtggagtg cctcggtctt cttcgtacag gaactctgac    5700
cactctgata caaaggcgcg cgtccaggcc agcacaaagg aggctatgtg ggaggggtag    5760
cgatcgttgt caaccagggg gtccacctt tccaaagtat gcaaacacat gtcaccctct     5820
tcaacatcca ggaatgtgat tggcttgtag gtgtatttca cgtgacctgg ggtccccgct    5880
gggggggtat aaaaggggc ggttctttgc tcttcctcac tgtcttccgg atcgctgtcc     5940
aggaacgtca gctgttgggg taggtattcc ctctcgaagg cgggcatgac ctctgcactc    6000
aggttgtcag tttctaagaa cgaggaggat ttgatattga cagtgccggt tgagatgcct    6060
ttcatgaggt tttcgtccat ttggtcagaa aacacaattt ttttattgtc aagtttggtg    6120
gcaaatgatc catacagggc gttggataaa agtttggcaa tggatcgcat ggtttggttc    6180
ttttccttgt ccgcgcgctc tttggcggcg atgttgagtt ggacatactc gcgtgccagg    6240
cacttccatt cggggaagat agttgttaat tcatctggca cgattctcac ttgccaccct    6300
cgattatgca aggtaattaa atccacactg gtggccacct cgcctcgaag gggttcattg    6360
gtccaacaga gcctacctcc tttcctagaa cagaaagggg gaagtgggtc tagcataagt    6420
tcatcgggag ggtctgcatc catggtaaag attcccggaa gtaaatcctt atcaaaatag    6480
ctgatgggag tggggtcatc taaggccatt tgccattctc gagctgccag tgcgcgctca    6540
tatgggttaa ggggactgcc ccatggcatg ggatgggtga gtgcagaggc atacatgcca    6600
```

```
cagatgtcat agacgtagat gggatcctca aagatgccta tgtaggttgg atagcatcgc    6660
ccccctctga tacttgctcg cacatagtca tatagttcat gtgatggcgc tagcagcccc    6720
ggacccaagt tggtgcgatt gggttttttct gttctgtaga cgatctggcg aaagatggcg   6780
tgagaattgg aagagatggt gggtctttga aaaatgttga atgggcatg aggtagacct     6840 acagagtctc tgacaaagtg ggcataagat tcttgaagct tggttaccag ttcggcggtg    6900
acaagtacgt ctagggcgca gtagtcaagt gtttcttgaa tgatgtcata acctggttgg    6960
ttttcttttt cccacagttc gcggttgaga aggtattctt cgcgatcctt ccagtactct    7020
tctagcggaa acccgtcttt gtctgcacgg taagatccta gcatgtagaa ctgattaact    7080
gccttgtaag ggcagcagcc cttctctacg ggtagagagt atgcttgagc agcttttcgt    7140
agcgaagcgt gagtaagggc aaaggtgtct ctgaccatga ctttgagaaa ttggtatttg    7200
aagtcgatgt cgtcacaggc tccctgttcc cagagttgga agtctacccg tttcttgtag    7260
gcggggttgg gcaaagcgaa agtaacatca ttgaagagaa tcttaccggc tctgggcata    7320
aaattgcgag tgatgcgaaa aggctgtggt acttccgctc gattgttgat cacctgggca    7380
gctaggacga tctcgtcgaa accgttgatg ttgtgtccta cgatgtataa ttctatgaaa    7440
cgcggcgtgc ctctgacgtg aggtagctta ctgagctcat caaaggttag gtctgtgggg    7500
tcagataagg cgtagtgttc gagagcccat tcgtgcaggt gaggatttgc atgtaggaat    7560
gatgaccaaa gatctaccgc cagtgctgtt tgtaactggt cccgatactg acgaaaatgc    7620
cggccaattg ccattttttc tggagtgaca cagtagaagg ttctggggtc ttgttgccat    7680
cgatcccact tgagtttaat ggctagatcg tgggccatgt tgacgagacg ctcttctcct    7740
gagagtttca tgaccagcat gaaaggaact agttgtttgc caaggatcc catccaggtg     7800 taagtttcca catcgtaggt caggaagagt cttctctgtgc gaggatgaga gccgatcggg    7860
aagaactgga tttcctgcca ccagttggag gattggctgt tgatgtgatg gaagtagaag    7920
tttctgcggc gcgccagca ttcgtgtttg tgcttgtaca gacggccgca gtagtcgcag      7980
cgttgcacgg gttgtatctc gtgaatgagt tgtacctggc ttcccttgac gagaaatttc    8040
agtgggaagc cgaggcctgg cgattgtatc tcgtgctctt ctatattcgc tgtatcggcc    8100
tgttcatctt ctgtttcgat ggtggtcatg ctgacgagcc cccgcgggag gcaagtccag    8160
acctcggcgc gggaggggcg gagctgaagg acgagagcgc gcaggctgga gctgtccaga    8220
gtcctgagac gctgcggact caggttagta ggtagggaca gaagattaac ttgcatgatc    8280
ttttccaggg cgtgcgggag gttcagatgg tacttgattt ccacaggttc gtttgtagag    8340
acgtcaatgg cttgcagggt tccgtgtcct ttgggcgcca ctaccgtacc tttgtttttt    8400
cttttgatcg gtggtggctc tcttgcttct tgcatgctca gaagcggtga cggggacgcg    8460
cgccgggcgg cagcggttgt tccggacccg agggcatggc tggtagtggc acgtcggcgc    8520
cgcgcacggg caggttctgg tactgcgctc tgagaagact tgcgtgcgcc accacgcgtc    8580
gattgacgtc ttgtatctga cgtctctggg tgaaagctac cggccccgtg agcttgaacc    8640
tgaaagagag ttcaacagaa tcaatttcgg tatcgttaac ggcagcttgt ctcagtattt    8700
cttgtacgtc accagagttg tcctggtagg cgatctccgc catgaactgc tcgatttctt    8760
cctcctgaag atctccgcga cccgtctttt cgacggtggc cgcgaggtca ttggagatac    8820
ggcccatgag ttgggagaat gcattcatgc ccgcctcgtt ccagacgcgg ctgtaaacca    8880 cggcccctc ggagtctctt gcgcgcatca ccacctgagc gaggttaagc tccacgtgtc      8940
tggtgaagac cgcatagttg cataggcgct gaaaaaggta gttgagtgtg gtggcaatgt    9000
```

```
gttcggcgac gaagaaatac atgatccatc gtctcagcgg catttcgcta acatcgccca   9060
gagcttccaa gcgctccatg gcctcgtaga agtccacggc aaaattaaaa aactgggagt   9120
ttcgcgcgga cacggtcaat tcctcctcga gaagacggat gagttcggct atggtggccc   9180
gtacttcgcg ttcgaaggct cccgggatct cttcttcctc ttctatctct tcttccacta   9240
acatctcttc ttcgtcttca ggcggggggcg aggggggcac gcggcgacgt cgacggcgca   9300
cgggcaaacg gtcgatgaat cgttcaatga cctctccgcg gcggcggcgc atggtttcag   9360
tgacggcgcg gccgttctcg cgcggtcgca gagtaaaaac accgccgcgc atctccttaa   9420
agtggtgact gggaggttct ccgtttggga gggagagggc gctgattata cattttatta   9480
attggcccgt agggactgca cgcagagatc tgatcgtgtc aagatccacg ggatctgaaa   9540
acctttcgac gaaagcgtct aaccagtcac agtcacaagg taggctgagt acggcttctt   9600
gtgggcgggg gtggttatgt gttcggtctg ggtcttctgt ttcttcttca tctcgggaag   9660
gtgagacgat gctgctggtg atgaaattaa agtaggcagt tctaagacgg cggatggtgg   9720
cgaggagcac caggtctttg ggtccggctt gctggatacg caggcgattg gccattcccc   9780
aagcattatc ctgacatcta gcaagatctt tgtagtagtc ttgcatgagc cgttctacgg   9840
gcacttcttc ctcacccgtt ctgccatgca tacgtgtgag tccaaatccg cgcattggtt   9900
gtaccagtgc caagtcagct acgactcttt cggcgaggat ggcttgctgt acttgggtaa   9960
gggtggcttg aaagtcatca aaatccacaa agcggtggta agctcctgta ttaatggtgt  10020
aagcacagtt ggccatgact gaccagttaa ctgtctggtg accagggcgc acgagctcgg  10080
tgtatttaag gcgcgaatag gcgcgggtgt caaagatgta atcgttgcag gtgcgcacca  10140
gatactggta ccctataaga aaatgcggcg gtggttggcg gtagagaggc catcgttctg  10200
tagctggagc gccaggggcg aggtcttcca acataaggcg gtgatagccg tagatgtacc  10260
tggacatcca ggtgattcct gcggcggtag tagaagcccg aggaaactcg cgtacgcggt  10320
tccaaatgtt gcgtagcggc atgaagtagt tcattgtagg cacggtttga ccagtgaggc  10380
gcgcgcagtc attgatgctc tatagacacg gagaaaatga aagcgttcag cgactcgact  10440
ccgtagcctg gaggaacgtg aacgggttgg gtcgcggtgt accccggttc gagacttgta  10500
ctcgagccgg ccggagccgc ggctaacgtg gtattggcac tcccgtctcg acccagccta  10560
caaaaatcca ggatacggaa tcgagtcgtt ttgctggttt ccgaatggca gggaagtgag  10620
tcctattttt ttttttttgcc gctcagatgc atcccgtgct gcgacagatg cgcccccaac  10680
aacagccccc ctcgcagcag cagcagcagc aatcacaaaa ggctgtccct gcaactactg  10740
caactgccgc cgtgagcggt gcgggacagc ccgcctatga tctggacttg aagagggcg   10800
aaggactggc acgtctaggt gcgccttcac ccgagcggca tccgcgagtt caactgaaaa  10860
aagattctcg cgaggcgtat gtgccccaac agaacctatt tagagacaga agcggcgagg  10920
agccggagga gatgcgagct tcccgcttta acgcgggtcg tgagctgcgt cacggtttgg  10980
accgaagacg agtgttgcgg gacgaggatt tcgaagttga tgaaatgaca gggatcagtc  11040
ctgccagggc acacgtgtct gcagccaacc ttgtatcggc ttacgagcag acagtaaagg  11100
aagagcgtaa cttccaaaag tctttttaata atcatgtgcg aaccctgatt gcccgcgaag  11160
aagttaccct tggtttgatg catttgtggg atttgatgga agctatcatt cagaacccta  11220
ctagcaaacc tctgaccgcc cagctgtttc tggtggtgca acacagcaga gacaatgagg  11280
cttcagaga ggcgctgctg aacatcaccg aacccgaggg gagatggttg tatgatctta  11340
```

```
tcaacattct acagagtatc atagtgcagg agcggagcct gggcctggcc gagaaggtgg    11400
ctgccatcaa ttactcggtt ttgagcttgg gaaaatatta cgctcgcaaa atctacaaga    11460
ctccatacgt tcccatagac aaggaggtga agatagatgg gttctacatg cgcatgacgc    11520
tcaaggtctt gaccctgagc gatgatcttg gggtgtatcg caatgacaga atgcatcgcg    11580
cggttagcgc cagcaggagg cgcgagttaa gcgacaggga actgatgcac agtttgcaaa    11640
gagctctgac tggagctgga accgagggtg agaattactt cgacatggga gctgacttgc    11700
agtggcagcc tagtcgcagg gctctgagcg ccgcgacggc aggatgtgag cttccttaca    11760
tagaagaggc ggatgaaggc gaggaggaag agggcgagta cttggaagac tgatggcaca    11820
acccgtgttt tttgctagat ggaacagcaa gcaccggatc ccgcaatgcg ggcggcgctg    11880
cagagccagc cgtccggcat taactcctcg gacgattgga cccaggccat gcaacgtatc    11940
atggcgttga cgactcgcaa ccccgaagcc tttagacagc aaccccaggc caaccgtcta    12000
tcggccatca tggaagctgt agtgccttcc cgctctaatc ccactcatga gaaggtcctg    12060
gccatcgtga acgcgttggt ggagaacaaa gctattcgtc cagatgaggc cggactggta    12120
tacaacgctc tcttagaacg cgtggctcgc tacaacagta gcaatgtgca aaccaatttg    12180
gaccgtatga taacagatgt acgcgaagcc gtgtctcagc gcgaaaggtt ccagcgtgat    12240
gccaacctgg gttcgctggt ggcgttaaat gctttcttga gtactcagcc tgctaatgtg    12300
ccgcgtggtc aacaggatta tactaacttt ttaagtgctt tgagactgat ggtatcagaa    12360
gtacctcaga gcgaagtgta tcagtccggt cctgattact tctttcagac tagcagacag    12420
ggcttgcaga cggtaaatct gagccaagct tttaaaaacc ttaaaggttt gtggggagtg    12480
catgccccgg taggagaaag agcaaccgtg tctagcttgt taactccgaa ctcccgccta    12540
ttattactgt tggtagctcc tttcaccgac agcggtagca tcgaccgtaa ttcctatttg    12600
ggttacctac taaacctgta tcgcgaagcc atagggcaaa gtcaggtgga cgagcagacc    12660
tatcaagaaa ttacccaagt cagtcgcgct ttgggacagg aagacactgg cagtttggaa    12720
gccactctga acttcttgct taccaatcgg tctcaaaaga tccctcctca atatgctctt    12780
actgcggagg aggagaggat ccttagatat gtgcagcaga gcgtgggatt gtttctgatg    12840
caagaggggg caactccgac tgcagcactg gacatgacag cgcgaaatat ggagcccagc    12900
atgtatgcca gtaaccgacc tttcattaac aaactgctgg actacttgca cagagctgcc    12960
gctatgaact ctgattattt caccaatgcc atcttaaacc cgcactggct gcccccacct    13020
ggtttctaca cgggcgaata tgacatgccc gaccctaatg acggatttct gtgggacgac    13080
gtggacagcg atgttttttc acctctttct gatcatcgca cgtggaaaaa ggaaggcggc    13140
gatagaatgc attcttctgc atcgctgtcc ggggtcatgg gtgctaccgc ggctgagccc    13200
gagtctgcaa gtccttttcc tagtctaccc ttttctctac acagtgtacg tagcagcgaa    13260
gtgggtagaa taagtcgccc gagtttaatg ggcgaagagg agtatctaaa cgattccttg    13320
ctcagaccgg caagagaaaa aaatttccca aacaatggaa tagaaagttt ggtggataaa    13380
atgagtagat ggaagactta tgctcaggat cacagagacg agcctgggat catgggggatt    13440 acaagtagag cgagccgtag acgccagcgc catgacagac agaggggtct tgtgtgggac    13500
gatgaggatt cggccgatga tagcagcgtg ctggacttgg gtgggagagg aaggggcaac    13560
ccgtttgctc atttgcgccc tcgcttgggt ggtatgttgt aaaaaaaaat aaaaaaaaaa    13620
ctcaccaagg ccatgcgcac gagcgtacgt tcgttcttct ttattatctg tgtctagtat    13680
aatgaggcga gtcgtgctag gcggagcggt ggtgtatccg gagggtcctc ctccttcgta    13740
```

```
cgagagcgtg atgcagcagc agcaggcgac ggcggtgatg caatcccccac tggaggctcc   13800 cttttgtgcct ccgcgatacc tggcacctac ggagggcaga aacagcattc gttattcgga   13860
actggcacct cagtacgata ccaccaggtt gtatctggtg acaacaagt cggcggacat    13920 tgcttctctg aactatcaga atgaccacag caacttcttg accacggtgg tgcaaaacaa   13980
tgactttacc cctacggaag ccagcaccca gaccattaac tttgatgaac gatcgcggtg   14040
gggcggtcag ctaaagacca tcatgcatac taacatgcca aacgtgaacg agtatatgtt   14100
tagtaacaag ttcaaagcgc gtgtgatggt gtccagaaaa cctcccgacg tgctgcagt    14160 tggggatact tatgatcaca agcaggatat tttgaaatat gagtggttcg agtttacttt   14220
gccagaaggc aacttttcag ttactatgac tattgatttg atgaacaatg ccatcataga   14280
taattacttg aaagtgggta gacagaatgg agtgcttgaa agtgacattg gtgttaagtt   14340
cgacaccagg aacttcaagc tgggatggga tcccgaaacc aagttgatca tgcctggagt   14400
gtatacgtat gaagccttcc atcctgacat tgtcttactg cctggctgcg gagtggattt   14460
taccgagagt cgtttgagca accttcttgg tatcagaaaa aaacagccat ttcaagaggg   14520
ttttaagatt ttgtatgaag attttagaagg tggtaatatt ccggccctct tggatgtaga   14580
tgcctatgag aacagtaaga aagaacaaaa agccaaaata gaagctgcta cagctgctgc   14640
agaagctaag gcaaacatag ttgccagcga ctctacaagg gttgctaacg ctggagaggt   14700
cagaggagac aattttgcgc caacacctgt tccgactgca gaatcattat tggccgatgt   14760
gtctgaagga acggacgtga aactcactat tcaacctgta gaaaaagata gtaagaatag   14820
aagctataat gtgttggaag acaaaatcaa cacagcctat cgcagttggt atctttcgta   14880
caattatggc gatcccgaaa aaggagtgcg ttcctggaca ttgctcacca cctcagatgt   14940
cacctgcgga gcagagcagg tctactggtc gcttccagac atgatgaagg atcctgtcac   15000 ttttccgctcc actagacaag tcagtaacta ccctgtggtg ggtgcagagc ttatgcccgt   15060
cttctcaaag agcttctaca cgaacaagc tgtgtactcc cagcagctcc gccagtccac   15120
ctcgcttacg cacgtcttca accgctttcc tgagaaccag atttttaatcc gtccgccggc   15180 gcccaccatt accaccgtca gtgaaaacgt tcctgctctc acagatcacg ggaccctgcc   15240
gttgcgcagc agtatccggg gagtccaacg tgtgaccgtt actgacgcca gacgccgcac   15300
ctgtccctac gtgtacaagg cactgggcat agtcgcaccg cgcgtccttt caagccgcac   15360
tttctaaaaa aaaaaaaaat gtccattctt atctcgccca gtaataacac cggttgggt    15420 ctgcgcgctc caagcaagat gtacggaggc gcacgcaaac gttctaccca acatcctgtc   15480
cgtgttcgcg gacatttttcg cgctccatgg ggcgccctca agggccgcac tcgcgttcga   15540
accaccgtcg atgatgtaat cgatcaggtg gttgccgacg cccgtaatta tactcctact   15600
gcgcctacat ctactgtgga tgcagttatt gacagtgtag tggctgacgc tcgcaactat   15660
gctcgacgta agagccggcg aaggcgcatt gccagacgcc accgagctac cactgccatg   15720
cgagccgcaa gagctctgct acgaagagct agacgcgtgg ggcgaagagc catgcttagg   15780
gcggccagac gtgcagcttc gggcgccagc gccggcaggt cccgcaggca agcagccgct   15840
gtcgcagcgg cgactattgc cgacatggcc caatcgcgaa gaggcaatgt atactgggtg   15900
cgtgacgctg ccaccggtca acgtgtaccc gtgcgcaccc gtccccctcg cacttagaag   15960
atactgagca gtctccgatg ttgtgtccca gcggcgagga tgtccaagcg caaatacaag   16020
gaagaaatgc tgcaggttat cgcacctgaa gtctacggcc aaccgttgaa ggatgaaaaa   16080
```

```
aaaccccgca aaatcaagcg ggttaaaaag gacaaaaaag aagaggaaga tggcgatgat   16140
gggctggcgg agtttgtgcg cgagtttgcc ccacggcgac gcgtgcaatg gcgtgggcgc   16200
aaagttcgac atgtgttgag acctggaact tcggtggtct ttacacccgg cgagcgttca   16260
agcgctactt ttaagcgttc ctatgatgag gtgtacgggg atgatgatat tcttgagcag   16320
gcggctgacc gattaggcga gtttgcttat ggcaagcgta gtagaataac ttccaaggat   16380
gagacagtgt cgatacccct tggatcatgga aatcccaccc ctagtcttaa accggtcact   16440
ttgcagcaag tgttacccgt aactccgcga acaggtgtta aacgcgaagg tgaagatttg   16500
tatcccacta tgcaactgat ggtacccaaa cgccagaagt tggaggacgt tttggagaaa   16560
gtaaaagtgg atccagatat tcaacctgag gttaaagtga gacccattaa gcaggtagcg   16620
cctggtctgg gggtacaaac tgtagacatt aagattccca ctgaaagtat ggaagtgcaa   16680
actgaacccg caaagcctac tgccacctcc actgaagtgc aaacggatcc atggatgccc   16740
atgcctatta caactgacgc cgccggtccc actcgaagat cccgacgaaa gtacggtcca   16800
gcaagtctgt tgatgcccaa ttatgttgta cacccatcta ttattcctac tcctggttac   16860
cgaggcactc gctactatcg cagccgaaac agtacctccc gccgtcgccg caagacacct   16920
gcaaatcgca gtcgtcgccg tagacgcaca agcaaaccga ctcccggcgc cctggtgcgg   16980
caagtgtacc gcaatggtag tgcggaacct ttgacactgc cgcgtgcgcg ttaccatccg   17040
agtatcatca cttaatcaat gttgccgctg cctccttgca gatatggccc tcacttgtcg   17100
ccttcgcgtt cccatcactg gttaccgagg aagaaactcg cgccgtagaa gagggatgtt   17160
gggacgcgga atgcgacgct acaggcgacg gcgtgctatc cgcaagcaat tgcggggtgg   17220
tttttttacca gccttaattc caattatcgc tgctgcaatt ggcgcgatac caggcatagc   17280
ttccgtggcg gttcaggcct cgcaacgaca ttgacattgg aaaaaaacgt ataaataaaa   17340
aaaaaaaaat acaatggact ctgacactcc tggtcctgtg actatgtttt cttagagatg   17400
gaagacatca atttttcatc cttggctccg cgacacggca cgaagccgta catgggcacc   17460
tggagcgaca tcggcacgag ccaactgaac ggggcgcct tcaattggag cagtatctgg    17520
agcgggctta aaaattttgg ctcaaccata aaaacatacg ggaacaaagc ttggaacagc   17580
agtacaggac aggcgcttag aaataaactt aaagaccaga acttccaaca aaagtagtc   17640
gatgggatag cttccggcat caatggagtg gtagatttgg ctaaccaggc tgtgcagaaa   17700
aagataaaca gtcgtttgga cccgccgcca gcaaccccag gtgaaatgca agtggaggaa   17760
gaaattcctc cgccagaaaa acgaggcgac aagcgtccgc gtcccgattt ggaagagacg   17820
ctggtgacgc gcgtagatga accgccttct tatgaggaag caacgaagct tggaatgccc   17880
accactagac cgatagcccc aatggccacc ggggtgatga aaccttctca gttgcatcga   17940
cccgtcacct tggatttgcc ccctccccct gctgctactg ctgtacccgc ttctaagcct   18000
gtcgctgccc cgaaaccagt cgccgtagcc aggtcacgtc ccggggcgc cctcgtcca    18060
aatgcgcact ggcaaaatac tctgaacagc atcgtgggtc taggcgtgca aagtgtaaaa   18120
cgccgtcgct gcttttaatt aaatatggag tagcgcttaa cttgcctatc tgtgtatatg   18180
tgtcattaca cgccgtcaca gcagcagagg aaaaaaggaa gaggtcgtgc gtcgacgctg   18240
agttactttc aagatggcca ccccatcgat gctgccccaa tgggcataca tgcacatcgc   18300
cggacaggat gcttcggagt acctgagtcc gggtctggtg cagttcgccc gcgccacaga   18360
cacctacttc aatctgggaa ataagtttag aaatcccacc gtagcgccga cccacgatgt   18420
gaccaccgac cgtagccagc ggctcatgtt gcgcttcgtg cccgttgacc gggaggacaa   18480
```

```
tacatactct tacaaagtgc ggtacaccct ggccgtgggc gacaacagag tgctggatat    18540
ggccagcacg ttctttgaca ttaggggtgt gttggacaga ggtcccagtt tcaaaccta    18600 ttctggtacg gcttacaact ccctggctcc taaaggcgct ccaaatacat ctcagtggat    18660
tgcagaaggt gtaaaaaata caactggtga ggaacacgta acagaagagg aaaccaatac    18720
tactacttac acttttggca atgctcctgt aaaagctgaa gctgaaatta caaagaagg    18780 actcccagta ggtttggaag tttcagatga agaaagtaaa ccgatttatg ctgataaaac    18840
atatcagcca gaacctcagc tgggagatga aacttggact gaccttgatg gaaaaaccga    18900
aaagtatgga ggcagggctc tcaaacccga tactaagatg aaaccatgct acgggtcctt    18960
tgccaaacct actaatgtga aaggcggtca ggcaaaacaa aaaacaacgg agcagccaaa    19020
tcagaaagtc gaatatgata tcgacatgga gttttttgat gcggcatcgc agaaaacaaa    19080
cttaagtcct aaaattgtca tgtatgcaga aaatgtaaat ttggaaactc agacactca    19140 tgtagtgtac aaacctggaa cagaagacac aagttccgaa gctaatttgg acaacaatc    19200 tatgcccaac agacccaact acattggctt cagagataac tttattggac ttatgtacta    19260
taacagtact ggtaacatgg gggtgctggc tggtcaagcg tctcagttaa atgcagtggt    19320
tgacttgcag gacagaaaca cagaactttc ttaccaactc ttgcttgact ctctgggcga    19380
cagaaccaga tactttagca tgtggaatca ggctgtggac agttatgatc ctgatgtacg    19440
tgttattgaa aatcatggtg tggaagatga acttcccaac tactgttttc cactggacgg    19500
cataggtgtt ccaacaacca gttacaaatc aatagttcca aatggagaca atgcgcctaa    19560
ttggaaggaa cctgaagtaa atggaacaag tgagatcgga cagggtaatt tgtttgccat    19620
ggaaattaac cttcaagcca atctatggcg aagtttcctt tattccaatg tggctctata    19680
tctcccagac tcgtacaaat acacccccgtc caatgtcact cttccagaaa acaaaaacac    19740
ctacgactac atgaacgggc gggtggtgcc gccatctcta gtagacacct atgtgaacat    19800
tggtgccagg tggtctctgg atgccatgga caatgtcaac ccattcaacc accacgtaa    19860 cgctggcttg cgttaccgat ccatgcttct gggtaacgga cgttatgtgc ctttccacat    19920
acaagtgcct caaaaattct tcgctgttaa aaacctgctg cttctcccag ctcctacac    19980 ttatgagtgg aactttagga aggatgtgaa catggttcta cagagttccc tcggtaacga    20040
cctgcgggta gatggcgcca gcatcagttt cacgagcatc aacctctatg ctactttttt    20100
ccccatggct cacaacaccg cttccaccct tgaagccatg ctgcggaatg acaccaatga    20160
tcagtcattc aacgactacc tatctgcagc taacatgctc taccccattc ctgccaatgc    20220
aaccaatatt cccatttcca ttccttctcg caactgggcg ctttcagag gctggtcatt    20280 taccagactg aaaaccaaag aaactccctc tttggggtct ggatttgacc cctactttgt    20340
ctattctggt tctattccct acctggatgg taccttctac ctgaaccaca cttttaagaa    20400
ggtttccatc atgtttgact cttcagtgag ctggcctgga aatgacaggt tactatctcc    20460
taacgaattt gaaataaagc gcactgtgga tggcgaaggc tacaacgtag cccaatgcaa    20520
catgaccaaa gactggttct tggtacagat gctcgccaac tacaacatcg gctatcaggg    20580
cttctacatt ccagaaggat acaaagatcg catgtattca ttttcagaa acttccagcc    20640 catgagcagg caggtggttg atgaggtcaa ttacaaagac ttcaaggccg tcgccatacc    20700
ctaccaacac aacaactctg gctttgtggg ttacatggct ccgaccatgc gccaaggtca    20760 acccatccc gctaactatc cctatccact cattggaaca actgccgtaa atagtgttac    20820
```

```
gcagaaaaag ttcttgtgtg acagaaccat gtggcgcata ccgttctcga gcaacttcat   20880
gtctatgggg gcccttacag acttgggaca gaatatgctc tatgccaact cagctcatgc   20940
tctggacatg acctttgagg tggatcccat ggatgagccc accctgcttt atcttctctt   21000
cgaagttttc gacgtggtca gagtgcatca gccacaccgc ggcatcatcg aggcagtcta   21060
cctgcgtaca ccgttctcgg ccggtaacgc taccacgtaa gaagcttctt gcttcttgca   21120
aatagcagct gcaaccatgg cctgcggatc ccaaaacggc tccagcgagc aagagctcag   21180
agccattgtc caagacctgg gttgcggacc ctattttttg ggaacctacg ataagcgctt   21240
cccgggggttc atggccccccg ataagctcgc ctgtgccatt gtaaatacgg ccggacgtga   21300
gacgggggga gagcactggt tggctttcgg ttggaaccca cgttctaaca cctgctacct   21360
ttttgatcct tttggattct cggatgatcg tctcaaacag atttaccagt ttgaatatga   21420
gggtctcctg cgccgcagcg ctcttgctac caaggaccgc tgtattacgc tggaaaaatc   21480
tacccagacc gtgcagggtc cccgttctgc cgcctgcgga cttttctgct gcatgttcct   21540
tcacgccttt gtgcactggc ctgaccgtcc catggacgga aaccccacca tgaaattgct   21600
aactggagtg ccaaacaaca tgcttcattc tcctaaagtc cagcccaccc tgtgtgacaa   21660
tcaaaaagca ctctaccatt ttcttaatac ccattcgcct tattttcgct cccatcgtac   21720
acacatcgaa agggccactg cgttcgaccg tatggatgtt caataatgac tcatgtaaac   21780
aacgtgttca ataaacatca ctttatttttt ttacatgtat caaggctctg cattacttat   21840
ttatttacaa gtcgaatggg ttctgacgag aatcagaatg acccgcaggc agtgatacgt   21900
tgcggaactg atacttgggt tgccacttga attcgggaat caccaacttg ggaaccggta   21960
tatcgggcag gatgtcactc cacagctttc tggtcagctg caaagctcca agcaggtcag   22020
gagccgaaat cttgaaatca caattaggac cagtgctttg agcgcgagag ttgcggtaca   22080
ccggattgca gcactgaaac accatcagcg acggatgtct cacgcttgcc agcacggtgg   22140
gatctgcaat catgcccaca tccagatctt cagcattggc aatgctgaac ggggtcatct   22200
tgcaggtctg cctacccatg gcgggcaccc aattaggctt gtggttgcaa tcgcagtgca   22260
gggggatcag tatcatcttg gcctgatcct gtctgattcc tggatacacg gctctcatga   22320
aagcatcata ttgcttgaaa gcctgctggg ctttactacc ctcggtataa aacatcccgc   22380
aggacctgct cgaaaactgg ttagctgcac agccggcatc attcacacag cagcgggcgt   22440
cattgttagc tatttgcacc acacttctgc cccagcggtt ttgggtgatt ttggttcgct   22500
cgggattctc ctttaaggct cgttgtccgt tctcgctggc cacatccatc tcgataatct   22560
gctccttctg aatcataata ttgccatgca ggcacttcag cttgccctca taatcattgc   22620
agccatgagg ccacaacgca cagcctgtac attcccaatt atggtgggcg atctgagaaa   22680
aagaatgtat cattccctgc agaaatcttc ccatcatcgt gctcagtgtc ttgtgactag   22740
tgaaagttaa ctgatgcct cggtgctcct cgtttacgta ctggtgacag atgcgcttgt   22800
attgttcgtg ttgctcaggc attagtttaa aagaggttct aagttcgtta ccagcctgt   22860
acttctccat cagcagacac atcacttcca tgcctttctc ccaagcagac caggggca   22920
agctaatcgg attcttaaca gtgcaggcag cagctccttt agccagaggg tcatctttag   22980
cgatcttctc aatgcttctt ttgccatcct tctcaacgat gcgcacgggc gggtagctga   23040
aacccactgc tacaagttgc gcctcttctc tttcttcttc gctgtcttga ctgatgtctt   23100
gcatggggat atgtttggtc ttccttggct tcttttggg gggtatcgga ggaggaggac   23160
tgtcgctccg ttccggagac agggaggatt gtgacgtttc gctcaccatt accaactgac   23220
```

```
tgtcggtaga agaacctgac cccacacggc gacaggtgtt tctcttcggg ggcagaggtg    23280
gaggcgattg cgaagggctg cggtccgacc tggaaggcgg atgactggca gaacccttc     23340 cgcgttcggg ggtgtgctcc ctgtggcggt cgcttaactg atttccttcg cggctggcca    23400
ttgtgttctc ctaggcagag aaacaacaga catggaaact cagccattgc tgtcaacatc    23460
gccacgagtg ccatcacatc tcgtcctcag cgacgaggaa aaggagcaga gcttaagcat    23520
tccaccgccc agtcctgcca ccacctctac cctagaagat aaggaggtcg acgcatctca    23580
tgacatgcag aataaaaaag cgaaagagtc tgagacagac atcgagcaag cccgggcta    23640 tgtgacaccg gtggaacacg aggaagagtt gaaacgcttt ctagagagag aggatgaaaa    23700
ctgcccaaaa caacgagcag ataactatca ccaagatgct ggaaataggg atcagaacac    23760
cgactacctc ataggggcttg acggggaaga cgcgctcctt aaacatctag caagacagtc    23820
gctcatagtc aaggatgcat tattggacag aactgaagtg cccatcagtg tggaagagct    23880
cagccgcgcc tacgagctta acctcttttc acctcgtact cccccaaac gtcagccaaa     23940 cggcacctgc gagccaaatc ctcgcttaaa cttttatcca gcttttgctg tgccagaagt    24000
actggctacc tatcacatct tttttaaaaa tcaaaaaatt ccagtctcct gccgcgctaa    24060
tcgcacccgc gccgatgccc tactcaatct gggacctggt tcacgcttac ctgatatagc    24120
ttccttggaa gaggttccaa agatcttcga gggtctgggc aataatgaga ctcgggccgc    24180
aaatgctctg caaaagggag aaaatggcat ggatgagcat cacagcgttc tggtggaatt    24240
ggaaggcgat aatgccagac tcgcagtact caagcgaagc atcgaggtca cacacttcgc    24300
atatcccgct gtcaacctgc cccctaaagt catgacggcg tcatggacc agttactcat      24360 taagcgcgca agtccccttt cagaagacat gcatgaccca gatgcctgtg atgagggtaa    24420
accagtggtc agtgatgagc agctaacccg atggctgggc accgactctc ccagggattt    24480
ggaagagcgt cgcaagctta tgatggccgt ggtgctggtt accgtagaac tagagtgtct    24540
ccgacgtttc tttaccgatt cagaaacctt gcgcaaactc aagagaatc tgcactacac     24600 ttttagacac ggctttgtgc ggcaggcatg caagatatct aacgtggaac tcaccaacct    24660
ggtttcctac atgggtattc tgcatgagaa tcgcctagga caaagcgtgc tgcacagcac    24720
cctgaagggg gaagcccgcc gtgattacat ccgcgattgt gtctatctgt acctgtgcca    24780
cacgtggcaa accggcatgg gtgtatggca gcaatgttta gaagaacaga acttgaaaga    24840
gcttgacaag ctcttacaga aatctcttaa ggttctgtgg acagggttcg acgagcgcac    24900
cgtcgcttcc gacctggcag acctcatctt cccagagcgt ctcagggtta ctttgcgaaa    24960
cggattgcct gactttatga gccagagcat gcttaacaat tttcgctctt tcatcctgga    25020
acgctccggt atcctgcccg ccacctgctg cgcactgccc tccgactttg tgcctctcac    25080
ctaccgcgag tgcccccgc cgctatggag tcactgctac ctgttccgtc tggccaacta    25140
tctctcctac cactcggatg tgatcgagga tgtgagcgga gacggcttgc tggagtgtca    25200
ctgccgctgc aatctgtgca cgcccaccg gtccctagct tgcaacccc agttgatgag     25260 cgaaacccag ataataggca cctttgaatt gcaaggcccc agcagccaag gcgatgggtc    25320
ttctcctggg caaagtttaa aactgacccc gggactgtgg acctccgcct acttgcgcaa    25380
gtttgctccg gaagattacc acccctatga aatcaagttc tatgaggacc aatcacagcc    25440
tccaaaggcc gaactttcgg cctgcgtcat cacccagggg gcaattctgg cccaattgca    25500
agccatccaa aaatcccgcc aagaatttct actgaaaaag ggtaaggggg tctaccttga    25560
```

```
cccccagacc ggcgaggaac tcaacacaag gttccctcag gatgtcccaa cgacgagaaa   25620
acaagaagtt gaaggtgcag ccgccgcccc cagaagatat ggaggaagat tgggacagtc   25680
aggcagagga ggcggaggag gacagtctgg aggacagtct ggaggaagac agtttggagg   25740
aggaaaacga ggaggcagag gaggtggaag aagtaaccgc cgacaaacag ttatcctcgg   25800
ctgcggagac aagcaacagc gctaccatct ccgctccgag tcgaggaacc cggcggcgtc   25860
ccagcagtag atgggacgag accggacgct tcccgaaccc aaccagcgct tccaagaccg   25920
gtaagaagga tcggcaggga tacaagtcct ggcgggggca taagaatgcc atcatctcct   25980
gcttgcatga gtgcggggc aacatatcct tcacgcggcg ctacttgcta ttccaccatg   26040
gggtgaactt tccgcgcaat gttttgcatt actaccgtca cctccacagc ccctactata   26100
gccagcaaat cccggcagtc tcgacagata agacagcgg cggcgacctc caacagaaaa   26160
ccagcagcgg cagttagaaa atacacaaca agtgcagcaa caggaggatt aaagattaca   26220
gccaacgagc cagcgcaaac ccgagagtta agaaatcgga tctttccaac cctgtatgcc   26280
atcttccagc agagtcgggg tcaagagcag gaactgaaaa taaaaaaccg atctctgcgt   26340
tcgctcacca gaagttgttt gtatcacaag agcgaagatc aacttcagcg cactctcgag   26400
gacgccgagg ctctcttcaa caagtactgc gcgctgactc ttaaagagta ggcagcgacc   26460
gcgcttattc aaaaaaggcg ggaattacat catcctcgac atgagtaaag aaattcccac   26520
gccttacatg tggagttatc aaccccaaat gggattggcg gcaggcgcct cccaggacta   26580
ctccacccgc atgaattggc tcagcgccgg gccttctatg atttctcgag ttaatgatat   26640
acgcgcctac cgaaaccaaa tacttttgga acagtcagct cttaccacca cgccccgcca   26700
acaccttaat cccagaaatt ggcccgccgc cctagtgtac caggaaagtc ccgctcccac   26760
cactgtatta cttcctcgag acgcccaggc cgaagtccaa atgactaatg caggtgcgca   26820
gttagctggc ggctccaccc tatgtcgtca caggcctcgg cataatataa aacgcctgat   26880
gatcagaggc cgaggtatcc agctcaacga cgagtcggtg agctctccgc ttggtctacg   26940
accagacgga atctttcaga ttgccggctg cgggagatct tccttcaccc ctcgtcaggc   27000
tgttctgact ttggaaagtt cgtcttcgca accccgctcg ggcggaatcg ggaccgttca   27060
atttgtggag gagtttactc cctctgtcta cttcaacccc ttctccggat ctcctgggca   27120
ttacccggac gagttcatac cgaacttcga cgcgattagc gagtcagtgg acggctacga   27180
ttgatgtctg gtgacgcggc tgagctatct cggctgcgac atctagacca ctgccgccgc   27240
tttcgctgct ttgcccggga actcattgag ttcatctact tcgaactccc caaggatcac   27300
cctcaaggtc cggcccacgg agtgcggatt tctatcgaag gcaaaataga ctctcgcctg   27360
caacgaattt tctcccagcg gcccgtgctg atcgagcgag accagggaaa caccacggtt   27420
tccatctact gcatttgtaa tcaccccgga ttgcatgaaa gcctttgctg tcttatgtgt   27480
actgagttta ataaaaactg aattaagact ctcctacgga ctgccgcttc ttcaacccgg   27540
attttacaac cagaagaacg aaacttttcc tgtcgtccag gactctgtta acttcacctt   27600
tcctactcac aaaactagaag ctcaacgact acaccgcttt tccagaagca ttttccctac   27660
taatactact ttcaaaaccg gaggtgagct ccaaggtctt cctacagaaa acccttgggt   27720
ggaagcgggc cttgtagtgc taggaattct tgcgggtggg cttgtgatta ttcttttgcta   27780
cctatacaca ccttgcttca ctttcttagt ggtgttgtgg tattggttta aaaaatgggg   27840
cccatactag tcttgcttgt tttactttcg cttttggaac cgggtctgc caattacgat   27900
ccatgtctag acttcgaccc agaaaactgc acacttactt ttgcacccga cacaagccgc   27960
```

```
atctgtggag ttcttattaa gtgcggatgg gaatgcaggt ccgttgaaat tacacacaat    28020
aacaaaacct ggaacaatac cttatccacc acatgggagc caggagttcc cgagtggtac    28080
actgtctctg tccgaggtcc tgacggttcc atccgcatta gtaacaacac tttcatttttt   28140 tctgaaatgt gcgatctggc catgttcatg agcaaacagt attctctatg gcctcctagc    28200
aaggacaaca tcgtaacgtt ctccattgct tattgcttgt gcgcttgcct tcttactgct    28260
ttactgtgcg tatgcataca cctgcttgta accactcgca tcaaaaacgc caataacaaa    28320
gaaaaaatgc cttaacctct ttctgtttac agacatggct tctcttacat ctctcatatt    28380
tgtcagcatt gtcactgccg ctcatggaca aacagtcgtc tctatccctc taggacataa    28440
ttacactctc ataggacccc caatcacttc agaggtcatc tggaccaaac tgggaagcgt    28500
tgattacttt gatataatct gcaacaaaac aaaaccaata atagtaactt gcaacataca    28560
aaatcttaca ttgattaatg ttagcaaagt ttacagcggt tactattatg gttatgacag    28620
atacagtagt caatatagaa attacttggt tcgtgttacc cagttgaaaa ccacgaaaat    28680
gccaaatatg gcaaagattc gatccgatga caattctcta gaacttttta catctcccac    28740
cacacccgac gaaaaaaaca tcccagattc aatgattgca attgttgcag cggtggcagt    28800
ggtgatggca ctaataataa tatgcatgct tttatatgct tgtcgctaca aaaagtttca    28860
tcctaaaaaa caagatctcc tactaaggct taacatttaa tttcttttta tacagccatg    28920
gtttccacta ccacattcct tatgcttact agtctcgcaa ctctgacttc tgctcgctca    28980
cacctcactg taactatagg ctcaaactgc acactaaaag gacctcaagg tggtcatgtc    29040
ttttggtgga gaatatatga caatggatgg tttacaaaac catgtgacca acctggtaga    29100
tttttctgca acggcagaga cctaaccatt atcaacgtga cagcaaatga caaaggcttc    29160
tattatggaa ccgactataa aagtagttta gattataaca ttattgtact gccatctacc    29220
actccagcac cccgcacaac tactttctct agcagcagtg tcgctaacaa tacaatttcc    29280
aatccaacct tgccgcgcgt tttaaaacgc actgtgaata attctacaac ttcacataca    29340
acaatttcca cttcaacaat cagcattatc gctgcagtga caattggaat atctattctt    29400
gtttttacca taacctacta cgcctgctgc tatagaaaag acaaacataa aggtgatcca    29460
ttacttagat ttgatattta atttgttctt ttttttttta tttacagtat ggtgaacacc    29520
aatcatggta cctagaaatt tcttcttcac catactcatt tgtgcattta atgtttgcgc    29580
tactttcaca gcagtagcca cagcaacccc agactgtata ggagcatttg cttcctatgc    29640 acttttttgct tttgttactt gcatctgcgt atgtagcata gtctgcctgg ttattaatttt   29700 tttccaactt atagactgga tccttgtgcg aattgcctac ctgcgccacc atcccgaata    29760
ccgcaaccaa aatatcgcgg cacttcttag actcatctaa aaccatgcag gctatactac    29820
caatattttt gcttctattg cttccctacg ctgtctcaac cccagctgcc tatagtactc    29880
caccagaaca ccttagaaaa tgcaaattcc aacaaccgtg gtcatttctt gcttgctatc    29940
gagaaaaatc agaatttccc ccaaatttaa taatgattgc tggaataatt aatataatct    30000
gttgcaccat aatttcattt ttgatatacc ccctatttga ttttggctgg aatgctccca    30060
atgcacatga tcatccacaa gacccagagg aacacattcc cctacaaaac atgcaacatc    30120
caatagcgct aatagattac gaaagtgaac cacaaccccc actactccct gctattagtt    30180
acttcaacct aaccggcgga gatgactgaa acactcacca cctccaattc cgccgaggat    30240
ctgctcgata tggacggccg cgtctcagaa cagcgactcg cccaactacg catccgccag    30300
```

```
cagcaggaac gcgcggccaa agagctcaga gatgtcatcc aaattcacca atgcaaaaaa    30360
ggcatattct gtttggtaaa acaagccaag atatcctacg agatcaccgc tactgaccat    30420
cgcctctctt acgaacttgg cccccaacga caaaaattta cctgcatggt gggaatcaac    30480
cccatagtta tcacccagca aagtggagat actaagggtt gcattcactg ctcctgcgat    30540
tccatcgagt gcacctacac cctgctgaag accctatgcg gcctaagaga cctgctacca    30600
atgaattaaa aaatgattaa taaaaaatca cttacttgaa atcagcaata aggtctctgt    30660
tgaaattttc tcccagcagc acctcacttc cctcttccca actctggtat tctaaaccccc   30720 gttcagcggc atactttctc catactttaa aggggatgtc aaattttagc tcctctcctg    30780
tacccacaat cttcatgtct ttcttcccag atgaccaaga gagtccggct cagtgactcc    30840
ttcaaccctg tctacccccta tgaagatgaa agcacctccc aacacccctt tataaaccca   30900
gggtttattt ccccaaatgg cttcacacaa agcccaaacg gagttcttac tttaaaatgt    30960
ttaaccccac taacaaccac aggcggatct ctacagctaa aagtgggagg gggacttaca    31020
gtggatgaca ccaacggttt tttgaaagaa aacataagtg ccaccacacc actcgttaag    31080
actggtcact ctataggttt accactagga gccggattgg gaacgaatga aaataaactt    31140
tgtatcaaat taggacaagg acttacattc aattcaaaca acatttgcat tgatgacaat    31200
attaacacct tatggacagg agtcaacccc accgaagcca actgtcaaat catgaactcc    31260
agtgaatcta atgattgcaa attaattcta acactagtta aaactggagc actagtcact    31320
gcatttgttt atgttatagg agtatctaac aatttttaata tgctaactac acacagaaat    31380
ataaatttta ctgcagagct gttttttcgat tctactggta atttactaac tagactctca    31440
tccctcaaaa ctccacttaa tcataaatca ggacaaaaca tggctactgg tgccattact    31500
aatgctaaag gtttcatgcc cagcacgact gcctatcctt tcaatgataa ttctagagaa    31560
aaagaaaact acatttacgg aacttgttac tacacagcta gtgatcgcac tgcttttccc    31620
attgacatat ctgtcatgct taaccgaaga gcaataaatg acgagacatc atattgtatt    31680
cgtataactt ggtcctggaa cacaggagat gccccagagg tgcaaacctc tgctacaacc    31740
ctagtcacct ccccatttac cttttactac atcagagaag acgactgaca aataaagttt    31800
aacttgttta tttgaaaatc aattcacaaa atccgagtag ttattttgcc tcccccttcc    31860
catttaacag aatacaccaa tctctcccca cgcacagctt taaacatttg gataccatta    31920
gatatagaca tggttttaga ttccacattc caaacagttt cagagcgagc caatctgggg    31980
tcagtgatag ataaaaatcc atcgggatag tcttttaaag cgctttcaca gtccaactgc    32040
tgcggatgcg actccggagt ctggatcacg gtcatctgga agaagaacga tgggaatcat    32100
aatccgaaaa cggtatcgga cgattgtgtc tcatcaaacc cacaagcagc cgctgtctgc    32160
gtcgctccgt gcgactgctg tttatgggat cagggtccac agtgtcctga agcatgattt    32220 taatagcccct aacatcaac tttctggtgc gatgcgcgca gcaacgcatt ctgatttcac    32280
tcaaatcttt gcagtaggta caacacatta ttacaatatt gtttaataaa ccataattaa    32340
aagcgctcca gccaaaactc atatctgata taatcgcccc tgcatgacca tcataccaaa    32400
gtttaatata aattaaatga cgttccctca aaaacacact acccacatac atgatctctt    32460
ttggcatgtg catattaaca atctgtctgt accatgacca acgttggtta atcatgcaac    32520
ccaatataac cttccggaac cacactgcca acaccgctcc cccagccatg cattgaagtg    32580 aacccctgctg attacaatga caatgaagaa cccaattctc tcgaccgtga atcacttgag    32640
aatgaaaaat atctatagtg gcacaacata gacataaatg catgcatctt ctcataattt    32700
```

```
ttaactcctc aggatttaga acatatccc agggaatagg aagctcttgc agaacagtaa    32760
agctggcaga acaaggaaga ccacgaacac aacttacact atgcatagtc atagtatcac    32820
aatctggcaa cagcgggtgg tcttcagtca tagaagctcg ggtttcattt tcctcacaac    32880
gtggtaactg ggctctggtg taagggtgat gtctggcgca tgatgtcgag cgtgcgcgca    32940
accttgtcat aatggagttg cttcctgaca ttctcgtatt ttgtatagca aaacgcggcc    33000
ctggcagaac acactcttct tcgccttcta tcctgccgct tagcgtgttc cgtgtgatag    33060
ttcaagtaca accacactct taagttggtc aaaagaatgc tggcttcagt tgtaatcaaa    33120
actccatcgc atctaatcgt tctgaggaaa tcatccacgg tagcatatgc aaatcccaac    33180
caagcaatgc aactggattg tgtttcaagc aggagaggag agggaagaga cggaagaacc    33240
atgttaattt ttattccaaa cgatctcgca gtacttcaaa ttgtagatcg cgcagatggc    33300
atctctcgcc cccactgtgt tggtgaaaaa gcacagctag atcaaaagaa atgcgatttt    33360
caaggtgctc aacggtggct tccagcaaag cctccacgcg cacatccaag aacaaaagaa    33420
taccaaaaga aggagcattt tctaactcct caatcatcat attacattcc tgcaccattc    33480
ccagataatt ttcagctttc cagccttgaa ttattcgtgt cagttcttgt ggtaaatcca    33540
atccacacat tacaaacagg tcccggaggg cgccctccac caccattctt aaacacaccc    33600
tcataatgac aaaatatctt gctcctgtgt cacctgtagc gaattgagaa tggcaacatc    33660
aattgacatg cccttggctc taagttcttc tttaagttct agttgtaaaa actctctcat    33720
attatcacca aactgcttag ccagaagccc cccgggaaca agagcagggg acgctacagt    33780
gcagtacaag cgcagacctc cccaattggc tccagcaaaa acaagattgg aataagcata    33840
ttgggaaccg ccagtaatat catcgaagtt gctggaaata taatcaggca gagtttcttg    33900
taaaaattga ataaaagaaa aatttgccaa aaaacattc aaaacctctg ggatgcaaat    33960
gcaataggtt accgcgctgc gctccaacat tgttagtttt gaattagtct gcaaaaataa    34020
aaaaaaaaac aagcgtcata tcatagtagc ctgacgaaca gatggataaa tcagtctttc    34080
catcacaaga caagccacag ggtctccagc tcgaccctcg taaaacctgt catcatgatt    34140
aaacaacagc accgaaagtt cctcgcggtg accagcatga ataattcttg atgaagcata    34200
caatccagac atgttagcat cagttaacga gaaaaaacag ccaacatagc ctttgggtat    34260
aattatgctt aatcgtaagt atagcaaagc caccccctcgc ggatacaaag taaaaggcac    34320
aggagaataa aaaatataat tatttctctg ctgctgttca ggcaacgtcg cccccggtcc    34380
ctctaaatac acatacaaag cctcatcagc catggcttac cagacaaagt acagcgggca    34440
cacaaagcac aagctctaaa gtgactctcc aacctctcca caatatatat atacacaagc    34500
cctaaactga cgtaatggga gtaaagtgta aaaaatcccg ccaaacccaa cacacacccc    34560
gaaactgcgt caccagggaa aagtacagtt tcacttccgc aatcccaaca ggcgtaactt    34620
cctctttctc acggtacgtg atatcccact aacttgcaac gtcatttttcc cacggtcgca    34680 ccgccccttt tagccgttaa ccccacagcc aatcaccaca cgatccacac ttttttaaaat    34740 cacctcattt acatattggc accattccat ctataaggta tattatatag atag    34794
```

<210> SEQ ID NO 3
<211> LENGTH: 5287
<212> TYPE: DNA
<213> ORGANISM: Adenovirus

<400> SEQUENCE: 3

```
ctatggcatc tcgatccagc agacctcctc gtttcgcggg tttggacggc tcctggaata    60
gggtatgaga cgatgggcgt ccagcgctgc cagggttcgg tccttccagg gtctcagtgt   120
tcgagtcagg gttgtttccg tcacagtgaa ggggtgtgcg cctgcttggg cgcttgccag   180
ggtgcgcttc agactcatcc tgctggtcga aaacttctgt cgcttggcgc cctgtatgtc   240
ggccaagtag cagtttacca tgagttcgta gttgagcgcc tcggctgcgt ggcctttggc   300
gcggagctta cctttggaag ttttcttgca taccgggcag tataggcatt tcagcgcata   360
caacttgggc gcaaggaaaa cggattctgg ggagtatgca tctgcgccgc aggaggcgca   420
aacagtttca cattccacca gccaggttaa atccggttca ttggggtcaa aaacaagttt   480
tccgccatat tttttgatgc gtttcttacc tttggtctcc atgagttcgt gtcctcgttg   540
agtgacaaac aggctgtccg tgtccccgta gactgatttt acaggcctct tctccagtgg   600
agtgcctcgg tcttcttcgt acaggaactc tgaccactct gatacaaagg cgcgcgtcca   660
ggccagcaca aaggaggcta tgtgggaggg gtagcgatcg ttgtcaacca gggggtccac   720
cttttccaaa gtatgcaaac acatgtcacc ctcttcaaca tccaggaatg tgattggctt   780
gtaggtgtat ttcacgtgac ctggggtccc cgctgggggg gtataaaagg gggcggttct   840
ttgctcttcc tcactgtctt ccggatcgct gtccaggaac gtcagctgtt ggggtaggta   900
ttccctctcg aaggcgggca tgacctctgc actcaggttg tcagtttcta agaacgagga   960
ggatttgata ttgacagtgc cggttgagat gcctttcatg aggttttcgt ccatctggtc  1020
agaaaacaca atttttttat tgtcaagttt ggtggcaaat gatccataca gggcgttgga  1080
taaaagtttg gcaatggatc gcatggtttg gttcttttcc ttgtccgcgc gctctttggc  1140
ggcgatgttg agttggacat actcgcgtgc caggcacttc cattcgggga agatagttgt  1200
taattcatct ggcacgattc tcacttgcca ccctcgatta tgcaaggtaa ttaaatccac  1260
actggtggcc acctcgcctc gaaggggttc attggtccaa cagagcctac ctcctttcct  1320
agaacagaaa gggggaagtg gtctagcat aagttcatcg ggagggtctg catccatggt  1380
aaagattccc ggaagtaaat ccttatcaaa atagctgatg ggagtggggt catctaaggc  1440
catttgccat tctcgagctg ccagtgcgcg ctcatatggg ttaaggggac tgccccatgg  1500
catgggatgg gtgagtgcag aggcatacat gccacagatg tcatagacgt agatgggatc  1560
ctcaaagatg cctatgtagg ttggatagca tcgcccccct ctgatacttg ctcgcacata  1620
gtcatatagt tcatgtgatg gcgctagcag ccccggaccc aagttggtgc gattgggttt  1680
ttctgttctg tagacgatct ggcgaaagat ggcgtgagaa ttggaagaga tggtgggtct  1740
ttgaaaaatg ttgaaatggg catgaggtag acctacagag tctctgacaa agtgggcata  1800
agattcttga agcttggtta ccagttcggc ggtgacaagt acgtctaggg cgcagtagtc  1860
aagtgtttct tgaatgatgt cataacctgg ttggtttttc ttttcccaca gttcgcggtt  1920
gagaaggtat tcttcgcgat ccttccagta ctcttctagc ggaaacccgt cttttgtctgc  1980 acggtaagat cctagcatgt agaactgatt aactgccttg taagggcagc agcccttctc  2040
tacgggtaga gagtatgctt gagcagcttt tcgtagcgaa gcgtgagtaa gggcaaaggt  2100
gtctctgacc atgactttga ggaattggta tttgaagtcg atgtcgtcac aggctccctg  2160
ttcccagagt tggaagtcta cccgtttctt gtaggcgggg ttgggcaaag cgaaagtaac  2220
atcattgaag agaatcttgc cggccctggg catgaaattg cgagtgatgc gaaaaggctg  2280
tggtacttcc gctcggttat tgataaacctg ggcagctagg acgatctcgt cgaaaccgtt  2340
gatgttgtgt cctacgatgt ataattctat gaaacgcggc gtgcctctga cgtgaggtag  2400
```

```
cttactgagc tcatcaaagg ttaggtctgt ggggtcagat aaggcgtagt gttcgagagc    2460
ccattcgtgc aggtgaggat tcgctttaag gaaggaggac cagaggtcca ctgccagtgc    2520
tgtttgtaac tggtcccggt actgacgaaa atgccgtccg actgccattt tttctggggt    2580
gacgcaatag aaggtttggg ggtcctgccg ccagcgatcc cacttgagtt ttatggcgag    2640
gtcataggcg atgttgacga gccgctggtc tccagagagt ttcatgacca gcatgaaggg    2700
gattagctgc ttgccaaagg accccatcca ggtgtaggtt tccacatcgt aggtgagaaa    2760
gagcctttct gtgcgaggat gagagccaat cgggaagaac tggatctcct gccaccagtt    2820
ggaggaatgg ctgttgatgt gatggaagta gaactccctg cgacgcgccg agcattcatg    2880
cttgtgcttg tacagacggc cgcagtagtc gcagcgttgc acgggttgta tctcgtgaat    2940
gagttgtacc tggcttccct tgacgagaaa tttcagtggg aagccgaggc ctggcgattg    3000
tatctcgtgc tttactatgt tgtctgcatc ggcctgttca tcttctgtct cgatggtggt    3060
catgctgacg agccctcgcg ggaggcaagt ccagacctcg gcgcggcagg ggcggagctc    3120
gaggacgaga gcgcgcaggc tggagctgtc cagggtcctg agacgctgcg gactcaggtt    3180
agtaggcagt gtcaggagat taacttgcat gatcttttgg agggcgtgcg ggaggttcag    3240
atagtacttg atctcaacgg gtccgttggt ggagatgtcg atggcttgca gggttccgtg    3300
tcccttgggc gctaccaccg tgcccttgtt tttcattttg gacggcggtg gctctgttgc    3360
ttcttgcatg tttagaagcg gtgtcgaggg cgcgcaccgg gcggcagggg cggctcggga    3420
cccggcggca tggctggcag tggtacgtcg gcgccgcgcg cgggtaggtt ctggtactgc    3480
gccctgagaa gactcgcatg cgcgacgacg cggcggttga catcctggat ctgacgcctc    3540
tgggtgaaag ctaccggccc cgtgagcttg aacctgaaag agagttcaac agaatcaatc    3600
tcggtatcgt tgacggcggc ttgcctaagg atttcttgca cgtcaccaga gttgtcctgg    3660
taggcgatct ccgccatgaa ctgctcgatc tcttcctctt gaagatctcc gcggcccgct    3720
ctctcgacgg tggccgcgag gtcgttggag atgcgcccaa tgagttgaga gaatgcattc    3780
atgcccgcct cgttccagac gcggctgtag accacggccc ccacgggatc tctcgcgcgc    3840
atgaccacct gggcgaggtt gagctccacg tggcgggtga agaccgcata gttgcatagg    3900
cgctggaaaa ggtagttgag tgtggtggcg atgtgctcgg tgacgaagaa atacatgatc    3960
catcgtctca gcggcatctc gctgacatcg cccagagctt ccaagcgctc catggcctcg    4020
tagaagtcca cggcaaaatt aaaaaactgg gagtttcgcg cggacacggt caactcctct    4080
tccagaagac ggataagttc ggcgatggtg gtgcgcacct cgcgctcgaa agcccctggg    4140
atttcttcct caatctcttc ttcttccact aacatctctt cctcttcagg tggggctgca    4200
ggaggagggg gaacgcggcg acgccggcgg cgcacgggca gacggtcgat gaatctttca    4260
atgacctctc cgcggcggcg gcgcatggtt tcagtgacgg cgcggccgtt ctcgcgcggt    4320
cgcagagtaa aaacaccgcc gcgcatctcc ttaaagtggt gactgggagg ttctccgttt    4380
gggagggaga gggcgctgat tatacatttt attaattggc ccgtagggac tgcacgcaga    4440
gatctgatcg tgtcaagatc cacgggatct gaaaaccttt cgacgaaagc gtctaaccag    4500
tcacagtcac aaggtaggct gagtacggct tcttgtgggc gggggtggtt atgtgttcgg    4560
tctgggtctt ctgtttcttc ttcatctcgg gaaggtgaga cgatgctgct ggtgatgaaa    4620
ttaaagtagg cagttctaag acggcggatg gtggcgagga gcaccaggtc tttgggtccg    4680
gcttgctgga tacgcaggcg attggccatt ccccaagcat tatcctgaca tctagcaaga    4740
```

```
tctttgtagt agtcttgcat gagccgttct acgggcactt cttcctcacc cgttctgcca    4800
tgcatacgtg tgagtccaaa tccgcgcatt ggttgtacca gtgccaagtc agctacgact    4860
ctttcggcga ggatggcttg ctgtacttgg gtaagggtgg cttgaaagtc atcaaaatcc    4920
acaaagcggt ggtaagctcc tgtattaatg gtgtaagcac agttggccat gactgaccag    4980
ttaactgtct ggtgaccagg gcgcacgagc tcggtgtatt taaggcgcga ataggcgcgg    5040
gtgtcaaaga tgtaatcgtt gcaggtgcgc accagatact ggtacccrat aagaaaatgc    5100
ggcggtggtt ggcggtagag aggccatcgt tctgtagctg gagcgccagg ggcgaggtct    5160
tccaacataa ggcggtgata gccgtagatg tacctggaca tccaggtgat tcctgcggcg    5220
gtagtagaag cccgaggaaa ctcgcgtacg cggttccaaa tgttgcgtag cggcatgaag    5280
tagttca                                                               5287
```

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4
gggagtttcg cgcggacacg g                                               21

<210> SEQ ID NO 5
<211> LENGTH: 21
<212> TYPE: DNA
<213> ORGANISM: artificial sequence
<220> FEATURE:
<223> OTHER INFORMATION: primer

<400> SEQUENCE: 5
gcgccgccgc cgcggagagg t                                               21

<210> SEQ ID NO 6
<211> LENGTH: 24
<212> TYPE: DNA
<213> ORGANISM: artificial sequence
<220> FEATURE:
<223> OTHER INFORMATION: primer

<400> SEQUENCE: 6
cgagagccca ttcgtgcagg tgag                                            24

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
gctgcgacta ctgcggccgt ctgt                                            24

<210> SEQ ID NO 8
<211> LENGTH: 4195
<212> TYPE: DNA
<213> ORGANISM: Adenovirus

<400> SEQUENCE: 8
tcataagact ctcgtccatc tggtcagaaa acacaatctt cttgttgtcc agcttggtgg    60
caaatgatcc atagagggca ttggatagaa gcttggcgat ggagcgcatg gtttggttct    120

```
tttccttgtc cgcgcgctcc ttggcggtga tgttaagctg gacgtactcg cgcgccacac    180
atttccattc aggaaagatg gttgtcagtt catccggaac tattctgatt cgccatcccc    240
tattgtgcag ggttatcaga tccacactgg tggccacctc gcctcggagg ggctcattgg    300
tccagcagag tcgacctcct tttcttgaac agaaaggggg gaggggtct agcatgaact     360 catcaggggt gtccgcatct atggtaaata ttcccggtag caaatctttg tcaaaatagc    420
tgatggtggc gggatcatcc aaggtcatct gccattctcg aactgccagc gcgcgctcat    480
aggggttaag aggggtgccc cagggcatgg ggtgggtgag cgcggaggca tacatgccac    540
agatatcgta gacatagagg ggctcttcga ggatgccgat gtaagtggga taacatcgcc    600
cccctctgat gcttgctcgc acatagtcat agagttcatg tgaggggca agaagacccg     660 ggcccagatt ggtgcggttg ggttttttccg ccctgtaaac gatctggcga aagatggcat   720
gggaattgga agagatagta ggtctctgga atatgttaaa atgggcatga ggtaagccta    780
cagagtccct tatgaagtgg gcatatgact cttgcagctt ggctaccagc tcggcggtga    840
tgagtacatc cagggcacag tagtcgagag tttcctggat gatgtcataa cgcggttggc    900 ttttctttc ccacagctcg cggttgagaa ggtattcttc gtgatccttc cagtactctt      960
cgaggggaaa cccgtctttt tctgcacggt aagagcccaa catgtagaac tgattgactg   1020
ccttgtaggg acagcatccc ttctccactg ggagagagta tgcttgggct gcattgcgca    1080
gcgaggtatg agtgagggca aaagtgtccc tgaccatgac tttgaggaat tgatacttga    1140
agtcgatgtc atcacaggcc ccctgttccc agagttggaa gtccacccgc ttcttgtagg    1200
cggggttggg caaagcgaaa gtaacatcat tgaagaggat cttgccggcc ctgggcatga    1260
aatttcgggt gattttgaaa ggctgaggaa cctctgctcg gttattgata acctgagcgg    1320
ccaagacgat ctcatcaaag ccattgatgt tgtgccccac tatgtacagt tctaagaatc    1380
gaggggtgcc cctgacatga ggcagcttct tgagttcttc aaaagtgaga tctgtagggt    1440
cagtgagagc atagtgttcg agggcccatt cgtgcacgtg agggttcgct ttaaggaagg    1500
aggaccagag gtccactgcc agtgctgttt gtaactggtc ccggtactga cgaaaatgct    1560
gtccgactgc catcttttct ggggtgacgc aatagaaggt ttgggggtcc tgccgccagc    1620
gatcccactt gagtttttatg gcgaggtcat aggcgatgtt gacgagccgc tggtctccag    1680
agagtttcat gaccagcatg aagggggatta gctgcttgcc aaaggacccc atccaggtgt   1740
aggtttccac atcgtaggtg agaaagagcc tttctgtgcg aggatgagag ccaatcggga    1800
agaactggat ctcctgccac cagttggagg aatggctgtt gatgtgatgg aagtagaact    1860
ccctgcgacg cgccgagcat tcatgcttgt gcttgtacag acggccgcag tactcgcagc    1920
gattcacggg atgcaccta tgaatgagtt gtacctgact tcctttgacg agaaatttca    1980
gtggaaaatt gaggcctggc gcttgtacct cgcgctttac tatgttgtct gcatcggcat    2040
gaccatcttc tgtctcgatg gtggtcatgc tgacgagccc tcgcgggagg caagtccaga    2100
cctcggcgcg gcaggggcgg agctcgagga cgagagcgcg caggccggag ctgtccaggg    2160
tcctgagacg ctgcggagtc aggttagtag gcagtgtcag gagattaact tgcatgatct    2220
tttggagggc gtgagggagg ttcagatagt acttgatctc aacgggtccg ttggtggaga    2280
tgtcgatggc ttgcagggtt ccgtgtccct tgggcgctac caccgtgccc ttgttttttca   2340 ttttggacgg cggtggctct gttgcttctt gcatgtttag aagcggtgtc gagggcgcgc    2400
accgggcggc aggggcggct cgggacccgg cggcatggct ggcagtggta cgtcggcgcc    2460
```

```
gcgcgcgggt aggttctggt actgcgccct gagaagactc gcatgcgcga cgacgcggcg    2520
gttgacatcc tggatctgac gcctctgggt gaaagctacc ggccccgtga gcttgaacct    2580
gaaagagagt tcaacagaat caatctcggt atcgttgacg gcggcttgcc taaggatttc    2640
ttgcacgtcg ccagagttgt cctggtaggc gatctcggcc atgaactgct cgatctcttc    2700
ctcttgaaga tctccgcggc ccgctctctc gacggtggcc gcgaggtcgt tggagatgcg    2760
cccaatgagt tgagagaatg cattcatgcc cgcctcgttc cagacgcggc tgtagaccac    2820
agcccccacg ggatctctcg cgcgcatgac cacctgggcg aggttgagct ccacgtggcg    2880
ggtgaagacc gcatagttgc ataggcgctg gaaaaggtag ttgagtgtgg tggcgatgtg    2940
ctcggtgacg aagaaataca tgatccatcg tctcagcggc atctcgctga catcgcccag    3000
cgcttccaag cgctccatgg cctcgtagaa gtccacggca aagttaaaaa actgggagtt    3060
acgcgcggac acggtcaact cctcttccag aagacggata agttcggcga tggtggtgcg    3120
cacctcgcgc tcgaaagccc ctgggatttc ttcctcaatc tcttcttctt ccactaacat    3180
ctcttcctct tcaggtgggg ctgcaggagg aggggaacg cggcgacgcc ggcggcgcac    3240
gggcagacgg tcgatgaatc tttcaatgac ctctccgcgg cggcggcgca tggtctcggt    3300
gacggcacga ccgttctccc tgggtctcag agtgaagacg cctccgcgca tctccctgaa    3360
gtggtgactg ggaggctctc cgttgggcag ggacaccgcg ctgattatgc attttatcaa    3420
ttgccccgta ggtactccgc gcaaggacct gatcgtctca agatccacgg gatctgaaaa    3480
cctttcgacg aaagcgtcta accagtcgca atcgcaaggt aggctgagca ctgtttcttg    3540
cgggcggggg cggctagacg ctcggtcggg gttctctctt tcttctcctt cctcctcttg    3600
ggagggtgag acgatgctgc tggtgatgaa attaaaatag gcagttttga gacggcggat    3660
ggtggcgagg agcaccaggt ctttgggtcc ggcttgttgg atacgcaggc gatgagccat    3720
tccccaagca ttatcctgac atctggccag atctttatag tagtcttgca tgagtcgttc    3780
cacgggcact tcttcttcgc ccgctctgcc atgcatgcga gtgatcccga acccgcgcat    3840
gggctggaca agtgccaggt ccgctacaac cctttcggcg aggatggctt gctgcacctg    3900
ggtgagggtg gcttggaagt cgtcaaagtc cacgaagcgg tggtaggccc cggtgttgat    3960
tgtgtaggag cagttggcca tgactgacca gttgactgtc tggtgcccag ggcgcacgag    4020
ctcggtgtac ttgaggcgcg agtatgcgcg ggtgtcaaag atgtaatcgt tgcaggtgcg    4080
caccaggtac tggtagccaa tgagaaagtg tggcggtggc tggcggtaca ggggccatcg    4140
ctctgtagcc ggggctccgg gggcgaggtc ttccagcatg aggcggtggt agccg         4195
```

CHIMERIC ADENOVIRUSES FOR USE IN CANCER TREATMENT

This application claims the benefit of U.S. Provisional Application Ser. No. 60/574,851, filed on May 26, 2004, which is incorporated herein by reference.

FIELD OF THE INVENTION

The invention described herein relates generally to the field of molecular biology, and more specifically to oncolytic adenoviruses having therapeutic applications.

BACKGROUND OF THE INVENTION

Cancer is a leading cause of death in the United States and elsewhere. Depending on the type of cancer, it is typically treated with surgery, chemotherapy, and/or radiation. These treatments often fail, and it is clear that new therapies are necessary, to be used alone or in combination with classical techniques.

One approach has been the use of adenoviruses, either alone or as vectors able to deliver anti-cancer therapeutic proteins to tumor cells. Adenoviruses are non-enveloped icosohedral double-stranded DNA viruses with a linear genome of approximately 36 kilobase pairs. Each end of the viral genome has a short sequence known as the inverted terminal repeat (or ITR), which is required for viral replication. All human adenovirus genomes examined to date have the same general organization; that is, the genes encoding specific functions are located at the same position on the viral genome. The viral genome contains five early transcription units (E1A, E1B, E2, E3, and E4), two delayed early units (IX and Iva2), and one late unit (major late) that is processed to generate five families of late mRNAs (L1-L5). Proteins encoded by the early genes are involved in replication, whereas the late genes encode viral structural proteins. Portions of the viral genome can be readily substituted with DNA of foreign origin and recombinant adenoviruses are structurally stable, properties that make these viruses potentially useful for gene therapy (see Jolly, D. (1994) *Cancer Gene Therapy* 1:51-64).

Currently, the research efforts to produce clinically useful adenoviral therapy have focused on the adenoviral serotype, Ad5. The genetics of this human adenovirus are well-characterized and systems are well described for its molecular manipulation. High capacity production methods have been developed to support clinical applications, and some clinical experience with the agent is available. See, Jolly, D. (1994) *Cancer Gene Therapy*, 1:51-64. Research related to the use of human adenoviruses (Ad) in cancer treatment has focused on the development of Ad5-based adenoviruses that have a higher potency in, or are preferentially targeted to, specific tumor cell types and there exists a need for generation of more potent oncolytic viruses if adenoviral therapy is to find practical application in a clinical setting.

Ad5 is only one of 51 currently known adenoviral serotypes, which are classified into subgroups A-F, based on various attributes including their hemagglutination properties ((see, Shenk, "Adenoviridae: The Viruses and Their Replication," in Fields Virology, Vol. 2, Fourth Edition, Knipe, ea., Lippincott, Williams & Wilkins, pp. 2265-2267 (2001)). These serotypes differ at a variety of levels, e.g. pathology in humans and rodents, cell receptors used for attachment, but these differences have been largely ignored as potential means to develop more potent oncolytic adenoviruses (with the exception of fiber alterations, see Stevenson et al. (1997) *J. Virol.* 71:4782-4790; Krasnykh et al. (1996) *J. Virol.* 70:6839-6846; Wickham et al. (1997) *J. Virol.* 71:8221-8229; Legrand et al. (2002) Curr. Gene Ther. 2:323-329; Barnett et al. (2002) Biochim. Biophys. Acta 1-3:1-14; U.S. patent application Ser. No. 2003/0017138).

Exploitation of differences among adenoviral serotypes may provide a source of more effective adenoviral-based therapeutics, using novel adenoviruses with increased selectivity and potency. There is a need for such improved adenoviral-based therapies.

SUMMARY OF THE INVENTION

The present invention provides novel chimeric adenoviruses, or variants or derivatives thereof, useful for viral-based therapy. In particular, the invention provides for chimeric adenoviruses, or variants or derivatives thereof, having a genome comprising an E2B region wherein said E2B region comprises a nucleic acid sequence derived from a first adenoviral serotype and a nucleic acid sequence derived from a second adenoviral serotype;

wherein said first and second adenoviral serotypes are each selected from the adenoviral subgroups B, C, D, E, or F and are distinct from each other; and wherein said chimeric adenovirus is oncolytic and demonstrates an enhanced therapeutic index for a tumor cell.

In one embodiment, the chimeric adenovirus further comprises regions encoding fiber, hexon, and penton proteins, wherein the nucleic acids encoding said proteins are all from the same adenoviral serotype. In another embodiment, the chimeric adenovirus of the invention comprises a modified E3 or E4 region.

In another embodiment, the chimeric adenovirus demonstrates an enhanced therapeutic index in a colon, breast, pancreas, lung, prostate, ovarian or hemopoietic tumor cell. In a particularly preferred embodiment, the chimeric adenovirus displays an enhanced therapeutic index in colon tumor cells.

In a preferred embodiment, the E2B region of the chimeric adenovirus comprises SEQ ID NO: 3. In a particularly preferred embodiment, the chimeric adenovirus comprises SEQ ID NO: 1.

The present invention provides for a recombinant chimeric adenovirus, or a variant or derivative thereof, having a genome comprising an E2B region wherein said E2B region comprises a nucleic acid sequences derived from a first adenoviral serotype and a nucleic acid second derived from a second adenoviral serotype;

wherein said first and second adenoviral serotypes are each selected from the adenoviral subgroups B, C, D, E, or F and are distinct from each other;

wherein said chimeric adenovirus is oncolytic and demonstrates an enhanced therapeutic index for a tumor cell; and wherein said chimeric adenovirus has been rendered replication deficient through deletion of one or more adenoviral regions encoding proteins involved in adenoviral replication selected from the group consisting of E1, E2, E3 or E4.

In one embodiment, the chimeric adenovirus of the invention further comprises a heterologous gene that encodes a therapeutic protein, wherein said heterologous gene is expressed within a cell infected with said adenovirus. In a preferred embodiment, the therapeutic protein is selected from the group consisting of cytokines and chemokines, antibodies, pro-drug converting enzymes, and immunoregulatory proteins.

The present invention provides methods for using the chimeric adenoviruses of the invention for therapeutic purposes. In one embodiment, the chimeric adenoviruses can be used to inhibit the growth of cancer cells. In a particular embodiment, a chimeric adenovirus comprising SEQ ID NO: 1 is useful for inhibiting the growth of colon cancer cells.

In another embodiment, the adenoviruses of the invention are useful as vectors to deliver therapeutic proteins to cells.

The present invention provides a method for production of the chimeric adenoviruses of the invention, wherein the method comprises a) pooling of adenoviral serotypes representing adenoviral subgroups B-F, thereby creating an adenoviral mixture;
b) passaging the pooled adenoviral mixture from step (a) on an actively growing culture of tumor cells at a particle per cell ratio high enough to encourage recombination between serotypes, but not so high as to produce premature cell death;
c) harvesting the supernatant from step (b);
d) infecting a quiescent culture of tumor cells with the supernatant harvested in step (c);
e) harvesting the cell culture supernatant from step (d) prior to any sign of CPE;
f) infecting a quiescent culture of tumor cells with the supernatant harvested in step (e); and
g) isolating the chimeric adenovirus from the supernatant harvested in step (f) by plaque purification.

DETAILED DESCRIPTION OF THE INVENTION

Figure 1B:
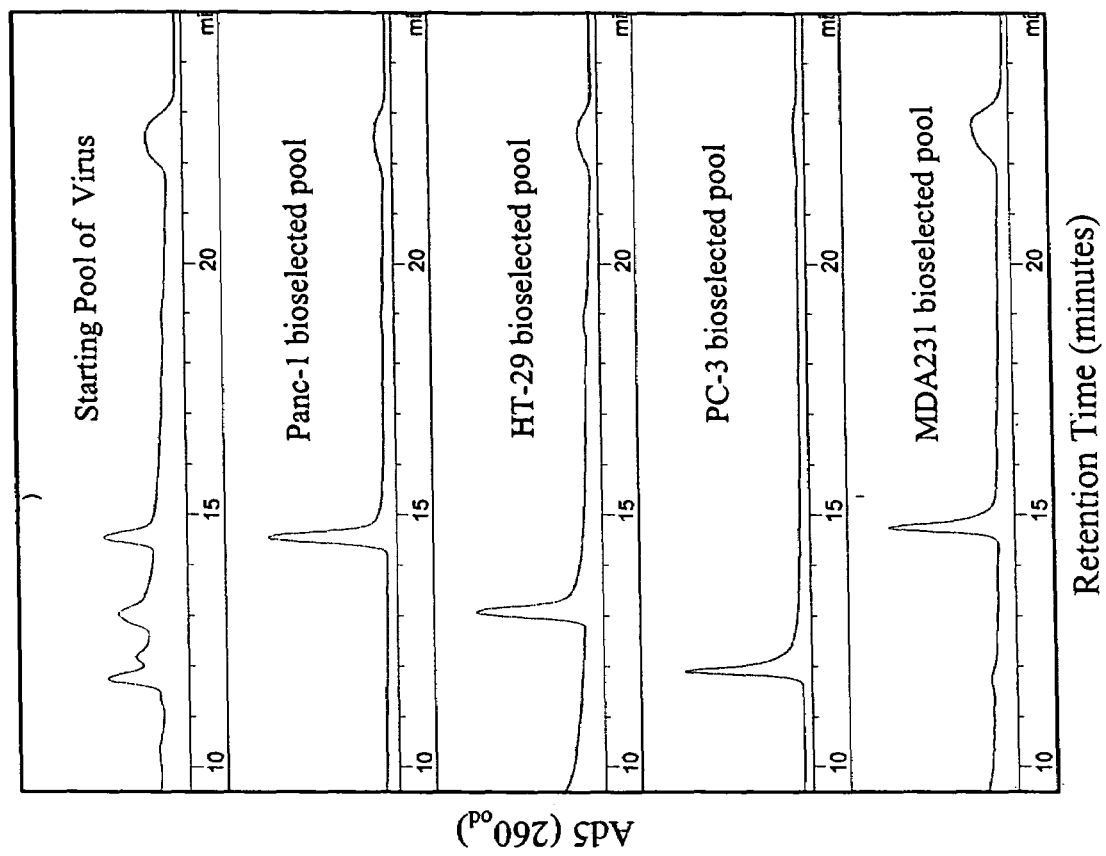
FIG. 1. Ad retention time profiles on a TMAE HPLC column. A) Retention profiles for the individual Ad serotypes that were used to generate the original starting viral pool. B) Retention profiles of the passage 20 pools derived from HT-29, Panc-1, MDA-231, and PC-3 cell lines, respectively.

All publications, including patents and patent applications, mentioned in this specification are herein incorporated by reference to the same extent as if each individual publication was specifically and individually indicated to be incorporated by reference in its entirety.

DEFINITIONS

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

As used herein, the term "adenovirus", "serotype" or "adenoviral serotype" refers to any of the 51 human adenoviral serotypes currently known, or isolated in the future. See, for example, Strauss, "Adenovirus infections in humans," in The Adenoviruses, Ginsberg, ea., Plenum Press, New York, N.Y., pp. 451-596 (1984). These serotypes are classified in the subgroups A-F (see, Shenk, "Adenoviridae: The Viruses and Their Replication," in Fields Virology, Vol. 2, Fourth Edition, Knipe, ea., Lippincott Williams & Wilkins, pp. 2265-2267 (2001), as shown in Table 1.

TABLE 1

| SubGroup | Adenoviral Serotype |
| --- | --- |
| A | 12, 18, 31 |
| B | 3, 7, 11, 14, 16, 21, 34, 35, 51 |
| C | 1, 2, 5, 6 |
| D | 8-10, 13, 15, 17, 19, 20, 22-30, 32, 33, 36-39, 42-49, 50 |
| E | 4 |
| F | 40, 41 |

As used herein, "chimeric adenovirus" refers to an adenovirus whose nucleic acid sequence is comprised of the nucleic acid sequences of at least two of the adenoviral serotypes described above.

As used herein, "parent adenoviral serotype" refers to the adenoviral serotype which represents the serotype from which the majority of the genome of the chimeric adenovirus is derived.

As used herein, the term "homologous recombination" refers to two nucleic acid molecules, each having homologous sequences, where the two nucleic acid molecules cross over or undergo recombination in the region of homology.

As used herein, the term "potency" refers to the lytic potential of a virus and represents its ability to replicate, lyse, and spread. For the purposes of the instant invention, potency is a value which compares the cytolytic activity of a given adenovirus of the invention to that of Ad5 in the same cell line, i.e. potency=$IC_{50}$ of AdX/$IC_{50}$ of Ad5, where X is the particular adenoviral serotype being examined and wherein the potency of Ad5 is given a value of 1.

As used herein, the term "oncolytic virus" refers to a virus that preferentially kills cancer cells as compared with normal cells.

As used herein, the term "therapeutic index" or "therapeutic window" refers to a number indicating the oncolytic potential of a given adenovirus and is determined by dividing the potency of the adenovirus in a cancer cell line by the potency of the same adenovirus in a normal (i.e. non-cancerous) cell line.

As used herein, the term "modified" refers to a molecule with a nucleotide or amino acid sequence differing from a naturally-occurring, e.g. a wild-type nucleotide or amino acid sequence. A modified molecule can retain the function or activity of a wild-type molecule, i.e. a modified adenovirus may retain its oncolytic activity. Modifications include mutations to nucleic acids as described below.

As used herein, "mutation" with reference to a polynucleotide or polypeptide, refers to a naturally-occurring, synthetic, recombinant, or chemical change or difference to the primary, secondary, or tertiary structure of a polynucleotide or polypeptide, as compared to a reference polynucleotide or polypeptide, respectively (e.g., as compared to a wild-type polynucleotide or polypeptide). Mutations include such changes as, for example, deletions, insertions, or substitutions. Polynucleotides and polypeptides having such mutations can be isolated or generated using methods well known in the art.

As used herein, "deletion" is defined as a change in either polynucleotide or amino acid sequences in which one or more polynucleotides or amino acid residues, respectively, are absent.

As used herein, "insertion" or "addition" is that change in a polynucleotide or amino acid sequence which has resulted in the addition of one or more polynucleotides or amino acid residues, respectively, as compared to the naturally occurring polynucleotide or amino acid sequence.

As used herein, "substitution" results from the replacement of one or more polynucleotides or amino acids by different polynucleotides or amino acids, respectively.

As used herein, the term "adenoviral derivative" refers to an adenovirus of the invention that has been modified such that an addition, deletion or substitution has been made to or in the viral genome, such that the resulting adenoviral derivative exhibits a potency and/or therapeutic index greater than that of the parent adenovirus, or in some other way is more therapeutically useful (i.e., less immunogenic, improved clearance profile). For example, a derivative of an adenovirus of the invention may have a deletion in one of the early genes of the viral genome, including, but not limited to, the E1A or E2B region of the viral genome.

As used herein, "variant" with reference to a polynucleotide or polypeptide, refers to a polynucleotide or polypeptide that may vary in primary, secondary, or tertiary structure, as compared to a reference polynucleotide or polypeptide, respectively (e.g., as compared to a wild-type polynucleotide or polypeptide). For example, the amino acid or nucleic acid sequence may contain a mutation or modification that differs from a reference amino acid or nucleic acid sequence. In some embodiments, an adenoviral variant may be a different isoform or polymorphism. Variants can be naturally-occurring, synthetic, recombinant, or chemically modified polynucleotides or polypeptides isolated or generated using methods well known in the art. Changes in the polynucleotide sequence of the variant may be silent. That is, they may not alter the amino acids encoded by the polynucleotide. Where alterations are limited to silent changes of this type, a variant will encode a polypeptide with the same amino acid sequence as the reference. Alternatively, such changes in the polynucleotide sequence of the variant may alter the amino acid sequence of a polypeptide encoded by the reference polynucleotide, resulting in conservative or non-conservative amino acid changes, as described below. Such polynucleotide changes may result in amino acid substitutions, additions, deletions, fusions and truncations in the polypeptide encoded by the reference sequence. Various codon substitutions, such as the silent changes that produce various restriction sites, may be introduced to optimize cloning into a plasmid or viral vector or expression in a particular prokaryotic or eukaryotic system.

As used herein, an "adenoviral variant" refers to an adenovirus whose polynucleotide sequence differs from a reference polynucleotide, e.g. a wild-type adenovirus, as described above. The differences are limited so that the polynucleotide sequences of the parent and the variant are similar overall and, in most regions, identical. As used herein, a first nucleotide or amino acid sequence is said to be "similar" to a second sequence when a comparison of the two sequences shows that they have few sequence differences (i.e., the first and second sequences are nearly identical). As used herein, the polynucleotide sequence differences present between the adenoviral variant and the reference adenovirus do not result in a difference in the potency and/or therapeutic index.

As used herein, the term "conservative" refers to substitution of an amino acid residue for a different amino acid residue that has similar chemical properties. Conservative amino acid substitutions include replacement of a leucine with an isoleucine or valine, an aspartate with a glutamate, or a threonine with a serine. Insertions or deletions are typically in the range of about 1 to 5 amino acids.

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

The single-letter codes for amino acid residues include the following: A=alanine, R=arginine, N=asparagine, D=aspartic acid, C=cysteine, Q=Glutamine, E=Glutamic acid, G=glycine, H=histidine, I=isoleucine, L=leucine, K=lysine, M=methionine, F=phenylalanine, P=proline, S=serine, T=threonine, W=tryptophan, Y=tyrosine, V=valine.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, *Proteins-Structure and Molecular Properties,* 2nd Ed., W.H. Freeman and Company, New York, 1993. Many detailed reviews are available on this subject, such as, for example, those provided by Wold, F., in *Posttranslational Covalent Modification of Proteins,* B. C. Johnson, Ed., Academic Press, New York, pp 1-12, 1983; Seifter et al., *Meth. Enzymol.* 182: 626-646, 1990 and Rattan et al., *Protein Synthesis: Posttranslational Modifications and Aging,* Ann. N.Y. Acad. Sci. 663: 48-62, 1992.

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translational natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

As used herein, the following terms are used to describe the sequence relationships between two or more polynucleotide or amino acid sequences: "reference sequence", "comparison window", "sequence identity", "percentage of sequence identity", "substantial identity", "similarity", and "homologous". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted, for example, by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), VectorNTI from Informatix, Geneworks, or MacVector software packages), or by inspection, and the best alignment (i. e., resulting in the highest percentage of homology over the comparison window) generated by the various methods is selected.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence. The term "similarity", when used to describe a polypeptide, is determined by comparing the amino acid sequence and the conserved amino acid substitutes of one polypeptide to the sequence of a second polypeptide. The term "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

As used herein, "homologous",when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

As used herein, "polymerase chain reaction" or "PCR" refers to a procedure wherein specific pieces of DNA are amplified as described in U.S. Pat. No. 4,683,195. Generally, sequence information from the ends of the polypeptide fragment of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, plasmid sequences, etc. (See generally Mullis et al., *Cold Spring Harbor Symp. Quant. Biol.,* 51: 263, 1987; Erlich, ed., *PCR Technology,* Stockton Press, NY, 1989).

As used herein, "stringency" typically occurs in a range from about $T_m$ (melting temperature)–5° C. (5° below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. As herein used, the term "stringent conditions" means hybridization will occur only if there is at least 95% and preferably at least 97% identity between the sequences.

As used herein, "hybridization" as used herein, shall include "any process by which a polynucleotide strand joins with a complementary strand through base pairing" (Coombs, J., *Dictionary of Biotechnology,* Stockton Press, New York, N.Y., 1994).

As used herein, the term "therapeutically effective dose" or "effective amount" refers to that amount of adenovirus which ameliorates the symptoms or conditions of a disease. A dose is considered a therapeutically effective dose in the treatment of cancer or its metastasis when tumor or metastatic growth is slowed or stopped, or the tumor or metastasis is found to shrink in size, so as to lead to an extension in life-span for the subject.

Adenoviruses of the Invention

The present invention provides chimeric adenoviruses, or variants or derivatives thereof, having a genome in which the nucleotide sequence of the E2B region of the chimeric adenovirus comprises nucleic acid sequences derived from at least two adenoviral serotypes, which serotypes are each selected from the adenoviral subgroups B, C, D, E and F and are distinct from each other. A chimeric adenovirus of the invention is oncolytic and demonstrates an enhanced therapeutic index for a tumor cell.

Isolation of Chimeric Adenoviruses

The chimeric adenoviruses of the invention, or variants or derivatives thereof, can be produced using modification of a technique referred to as "bioselection", in which an adenovirus with desired properties, such as enhanced oncogenicity or cell type specificity, is generated through the use of genetic selection under controlled conditions (Yan et al. (2003) *J. Virol.* 77:2640-2650).

In the present invention, a mixture of adenoviruses of differing serotypes is pooled and is passaged, preferably at least twice, on a subconfluent culture of tumor cells at a particle per cell ratio high enough to encourage recombination between serotypes, but not so high as to produce premature cell death. A preferred particle per cell ratio is approximately 500 particles per cell, and is easily determined by one skilled in the art. As used herein, a "subconfluent culture" of cells refers to a monolayer or suspension culture in which the cells are actively growing. For cells grown as a monolayer, an example would be a culture where approximately 50% to 80% of the area available for cell growth is covered with cells. Preferred is a culture where approximately 75% of the growth area is covered with cells.

In a preferred embodiment, the adenoviral mixture is one that includes adenoviral serotypes representative of the adenoviral subgroups B, C, D, E and F. Group A adenoviruses are not included in the mixture as they are associated with tumor formation in rodents. Preferred tumor cell lines useful in the bioselection process include, but are not limited to, those derived from breast, colon, pancreas, lung and prostate. Some examples of solid tumor cell lines useful for the "bioselective" passaging of the adenoviral mixture include, but are not limited to, MDA231, HT29, PAN-1 and PC-3 cells. Hemopoietic cell lines include, but are not limited to, the Raji and Daudi B-lymphoid cells, K562 erythroblastoid cells, U937 myeloid cells, and HSB2 T-lymphoid cells.

Adenoviruses produced during these initial passages are used to infect quiescent tumor cells at a particle to cell ratio low enough to permit the infection of a cell by no more than one adenovirus. After up to 20 passages under these conditions, the supernatant from the last passage is harvested prior to visible cytopathic effect (CPE, see Fields Virology, Vol. 2, Fourth Edition, Knipe, ea., Lippincott Williams & Wilkins, pp. 135-136) to increase selection of highly potent viruses. The harvested supernatant can be concentrated by techniques well known to those skilled in the art. A preferred method for attaining quiescent cells, i.e. ones in which active cell growth has stopped, in a monolayer culture is to allow the culture to grow for 3 days following confluence, where confluence means that the entire area available for cell growth is occupied (covered with cells). Similarly, suspension cultures can be grown to densities characterized by the absence of active cell growth.

The serotype profile of the concentrated supernatant, which contains the bioselected adenoviral pool, can be examined by measuring the retention times of the harvested viral pool on an anion exchange column, where different adenoviral serotypes are known to have characteristic retention times (Blanche et al. (2000) *Gene Therapy* 7:1055-1062); see Example 3, FIGS. 1A and B. Adenoviruses of the invention can be isolated from the concentrated supernatant by dilution and plaque purification, or other techniques well know in the art, and grown for further characterization. Techniques well known in the art are used to determine the sequence of the isolated chimeric adenoviruses (see Example 5).

Figure 7:
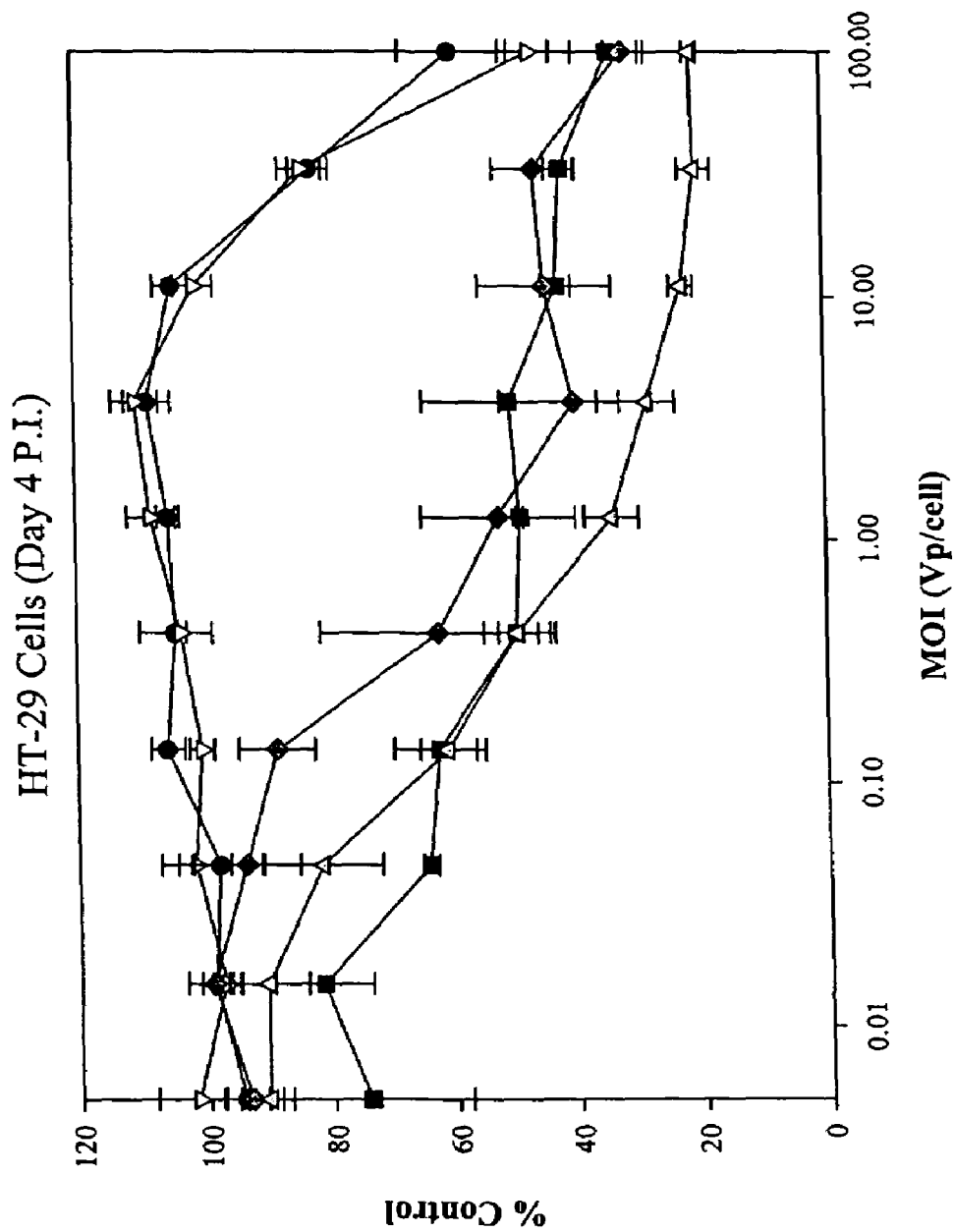
FIG. 7. Cytolytic activity of Recombinant Viruses. Recombinant viruses representing four viral populations (Adp11, ColoAd1, left end Ad11p/right end ColoAd1(ColoAd1.1) and left end ColoAd1/right end Ad11p (ColoAd1.2)) were constructed as described in Example 6. Cytolytic activity of each population in HT29 cells was determined as previously described. (Figure Legend: -●- Ad5; -□- AAd11p; -■- ColoAd1; -υ- ColoAd1.1;-▲- ColoAd1.2).

An example of a chimeric adenovirus of the invention is the chimeric adenovirus ColoAd1, which was isolated using HT29 colon cells in the bioselection process. ColoAd1 has the nucleic acid sequence of SEQ ID NO: 1. The majority of the nucleotide sequence of ColoAd1 is identical to the nucleotide sequence of the Ad11 serotype (SEQ ID NO: 2) (Stone et al. (2003) *Virology* 309:152-165; Mei et al. (2003) *J. Gen. Virology* 84:2061-2071). There are two deletions in the ColoAd1 nucleotide sequence as compared with Ad11, one 2444 base pairs in length within the E3 transcription unit region of the genome (base pairs 27979 to 30423 of SEQ ID NO: 2) and a second, smaller deletion, 25 base pairs in length (base pairs 33164 to 33189 of SEQ ID NO: 2), within the E4orf4 gene. The E2B transcription unit region (SEQ ID NO: 3) of ColoAd1, which encodes the adenoviral proteins DNA polymerase and terminal protein, is located between base pairs 5067 and 10354 of SEQ ID NO: 1, and is an area of homologous recombination between the Ad11 and Ad3 serotypes. Within this region of ColoAd1, there are 198 base pair changes, as compared with the sequence of Ad11 (SEQ ID NO: 1). The changes result in stretches of nucleotides within the E2B region of ColoAd1 which are homologous to the sequence within a portion of the E2B region of Ad3 (SEQ ID NO: 8), with the longest stretch of homology between ColoAd1 and Ad3 being 414 bp in length. The E2B region of ColoAd1 (SEQ ID NO: 3) confers enhanced potency to the ColoAd1 adenovirus as compared to unmodified Ad11 adenovirus (see Example 6; FIG. 7). In other embodiments, a chimeric adenovirus of the invention can comprise nucleic acid sequences from more than two adenoviral serotypes.

Figure 3A:
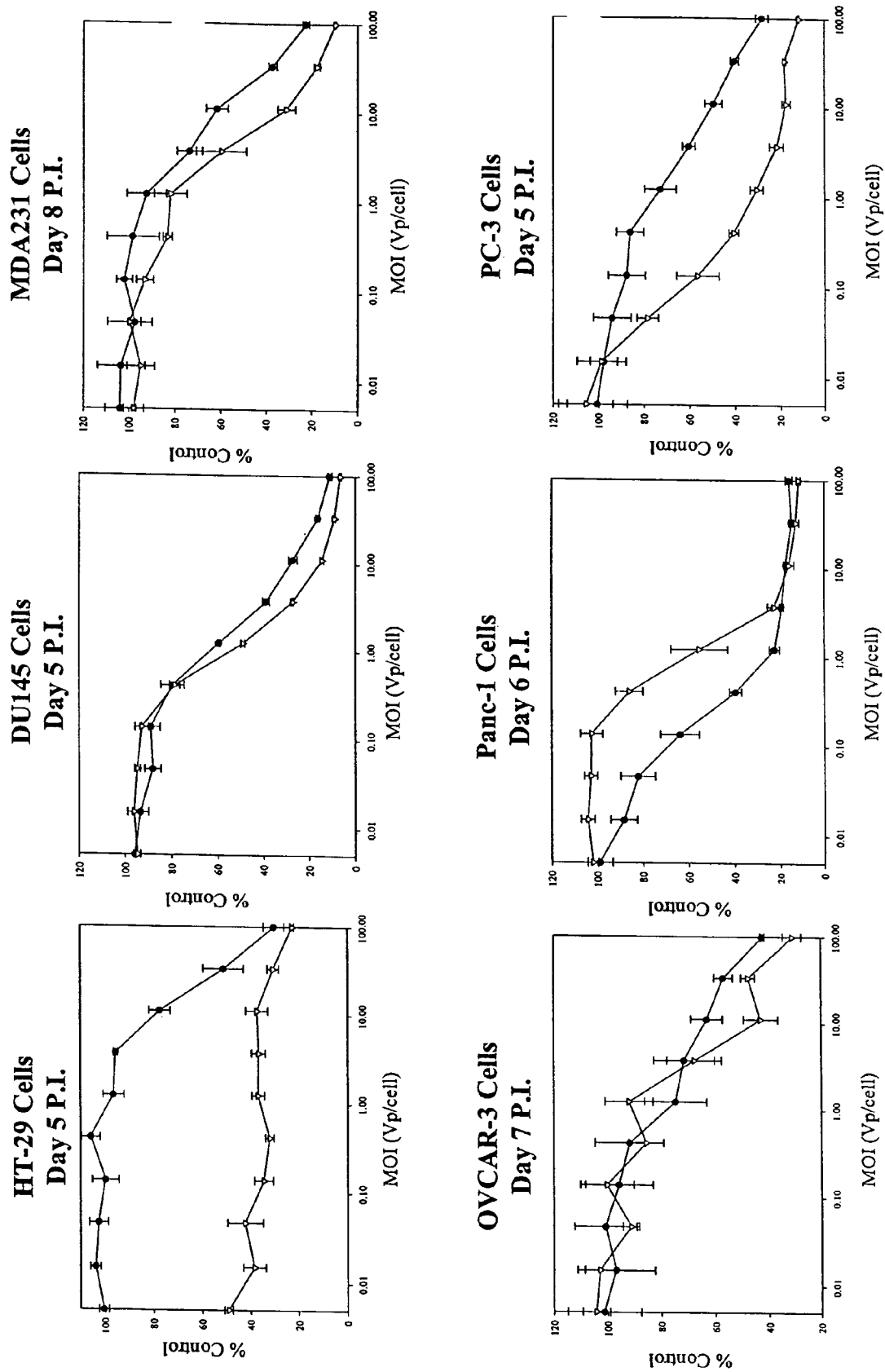
FIG. 3. Cytolytic activity of ColoAd1 and Ad5 on human tumor cell lines. An MTS assay was performed on A) a broad panel of human tumor cell lines and B) on a panel of human colon cancer cell lines to determine its potential potency specificity. The MTS assay was performed on differing days dependent upon the cell line. Each panel is a representative experiment that has been repeated at least three times. Each data point in the panel represents an assay done in quadruplicate and the results are expressed as the means ±SD (Figure Legend: -●- Ad5; -□- ColoAd1).
Figure 3B:
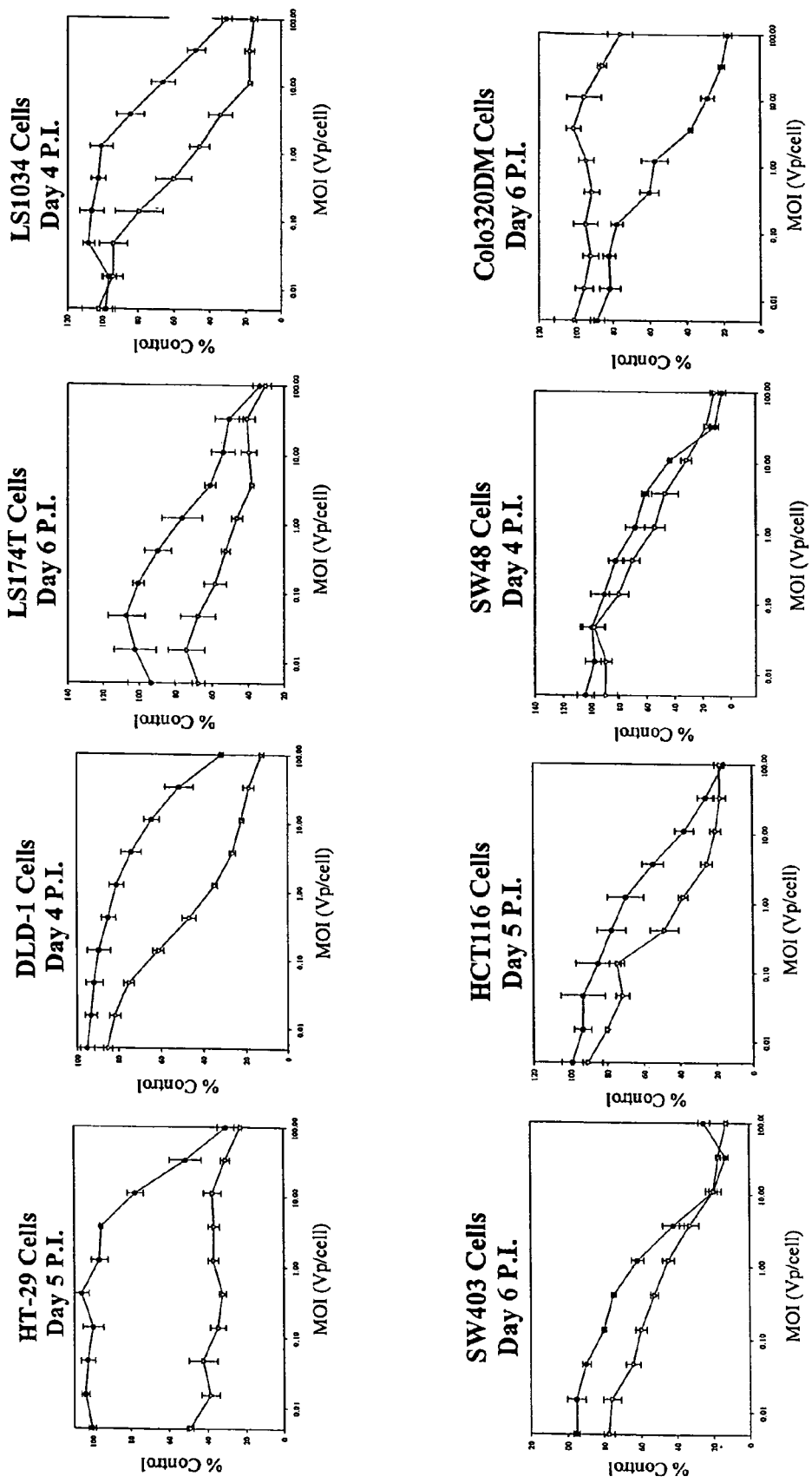

A chimeric adenovirus of the invention, or a variant or derivative thereof, can be evaluated for its selectivity in a specific tumor type by examination of its lytic potential in a panel of tumor cells derived from the same tissue upon which the adenoviral pool was initially passaged. For example, the chimeric adenovirus ColoAd1 (SEQ ID NO: 1), which was initially derived from an adenoviral pool passaged on HT-29 colon tumor cell lines, was re-examined both in HT-29 cells and in a panel of other colon-derived tumor cells lines, including DLD-1, LS174T, LS1034, SW403, HCl116, SW48, and Colo320DM (see FIG. 3B). Any available colon tumor cell lines would be equally useful for such an evaluation. Isolated adenoviral clones from adenoviral pools selected on other tumor cell types can be similarly tested in a suitable tumor cell panel, including, but not limited to, prostate cell lines (e.g. DU145 and PC-3 cell lines); pancreatic cell lines (e.g. the Panc-1 cell line); breast tumor cell lines (e.g. the MDA231 cell line) and ovarian cell lines (e.g. the OVCAR-3 cell line). Other available tumor cell lines are equally useful in isolating and identifying adenoviruses of the invention.

Figure 6:
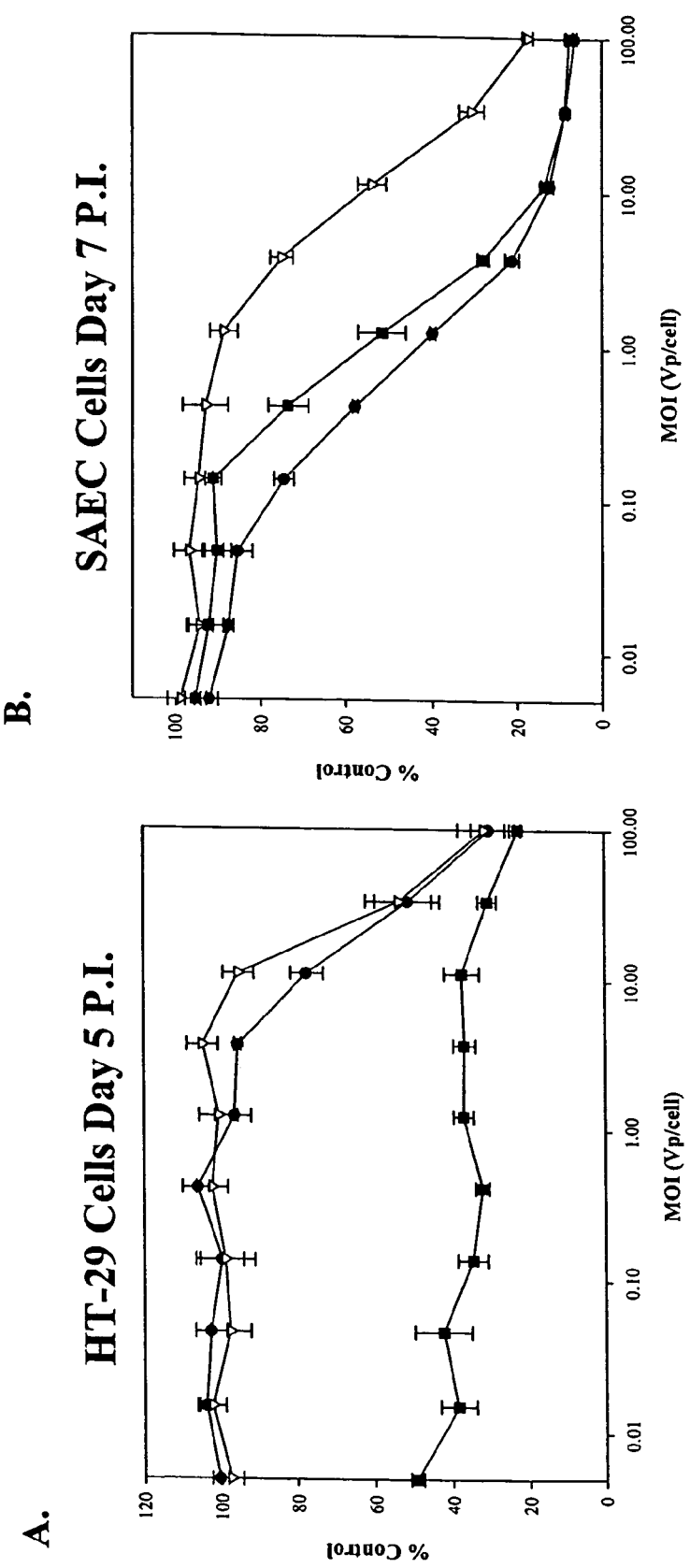
FIG. 6. Cytolytic activity of ColoAd1, Ad11p and Ad5 on a normal epithelial cell line (SAEC) and a human colon cancer cell line (HT-29). Each panel is a representative experiment that has been repeated at least three times. Each data point in the panel represents an assay done in quadruplicate and the results are expressed as the means ±SD (Figure Legend: -●- Ad5; -□- Ad11p; -■- ColoAd1).

The chimeric adenoviruses of the invention have an enhanced therapeutic index as compared with the adenoviral serotypes from which it is derived. (see FIG. 6, which compares the cytolytic activity of the chimeric adenovirus ColoAd1 with Ad11p).

The invention also encompasses chimeric adenoviruses that are constructed using recombinant techniques well-known to those skilled in the art. Such chimeric adenoviruses comprise a region of nucleotide sequence derived from one adenoviral serotype which is incorporated by recombinant techniques into the genome of a second adenoviral serotype. The incorporated sequence confers a property, e.g. tumor specificity or enhanced potency, to the parental adenoviral serotype. For example, the E2B region of ColoAd1 (SEQ ID NO: 3) can be incorporated into the genome of Ad35 or Ad9.

Adenoviral Derivatives

The invention also encompasses a chimeric adenovirus of the invention that is modified to provide other therapeutically useful chimeric adenoviruses. Modifications include, but are not limited to, those described below.

One modification is production of derivatives of the chimeric adenovirus of the invention substantially lacking the ability to bind p53, as a result of a mutation in the adenoviral gene that encodes the E1B-55K protein. Such viruses generally have some, or all, of the E1B-55K region deleted. (see U.S. Pat. No. 5,677,178). U.S. Pat. No. 6,080,578 describes, among other things, Ad5 mutants that have deletions in the region of the E1B-55K protein that is responsible for binding p53. Another preferred modification to the chimeric adenoviruses of the instant invention are mutations in the E1A region, as described in U.S. Pat. Nos. 5,801,029 and 5,972,706. These types of modifications provide derivatives of the chimeric adenoviruses of the invention with greater selectivity for tumor cells.

Another example of a modification encompassed by the invention is a chimeric adenovirus which exhibits an enhanced degree of tissue specificity due to placement of viral replication under the control of a tissue specific promoter as described in U.S. Pat. No. 5,998,205. Replication of a chimeric adenovirus of the invention can also be put under the control of an E2F responsive element as described in U.S. patent application Ser. No. 09/714,409. This modification affords a viral replication control mechanism based on the presence of E2F, resulting in enhanced tumor tissue specificity, and is distinct from the control realized by a tissue specific promoter. In both of these embodiments, the tissue specific promoter and the E2F responsive element are operably linked to an adenoviral gene that is essential for the replication of the adenovirus.

Another modification encompassed by the invention is use of a chimeric adenovirus of the invention, e.g. ColoAd1, as the backbone for production of novel replication-deficient adenoviral vectors. As described in Lai et al. ((2002) *DNA Cell Bio*. 21:895-913), adenoviral vectors which are replication deficient can be used to deliver and express therapeutic genes. Both first generation (in which the E1 and E3-regions are deleted) and second generation (in which the E4 region is additionally deleted) adenoviral vectors derived from the chimerc adenoviruses of the invention are provided herein. Such vectors are easily produced using techniques well known to those skilled in the art (see Imperiale and Kochanek (2004) *Curr. Top. Microbiol. Immunol*. 273:335-357; Vogels et al. (2003) *J. Virol*. 77:8263-8271).

A further modification encompassed by the invention is the insertion of a heterologous gene, useful as a marker or reporter for tracking the efficiency of viral infection. One embodiment of this type of modification is insertion of the thymidine kinase (TK) gene. The expression of TK within infected cells can be used to track the level of virus remaining in cells following viral infection, using radiolabeled subtrates of the TK reaction (Sangro et al. (2002) *Mol. Imaging Biol.* 4:27-33).

Methods for the construction of the modified chimeric adenoviruses are generally known in the art. See, Mittal, S. K. (1993) *Virus Res.* 28:67-90 and Hermiston, T. et al. (1999) Methods in Molecular Medicine: Adenovirus Methods and Protocols, W. S. M. Wold, ed, Humana Press. Standard techniques are used for recombinant nucleic acid methods, polynucleotide synthesis, and microbial culture and transformation (e.g., electroporation, lipofection). Generally, enzymatic reactions and purification steps are performed according to the manufacturers specifications. The techniques and procedures are generally performed according to conventional methods in the art and various general references (see generally, Sambrook et al., Molecular Cloning: A Laboratory Manual, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art.

Determination of Therapeutic Potential

Chimeric adenoviruses of the invention, or variants or derivatives thereof, can be evaluated for their therapeutic utility by examination of their lytic potential in tumor cells derived from tissues of interest as therapeutic targets. Tumor cell lines useful for testing such adenoviruses include, but are not limited to, colon cell lines, including but not limited to, DLD-1, HCT116, HT29, LS1034 and SW48 cell lines; prostate cell lines, including but not limited to, DU145 and PC-3 cell lines; pancreatic cell lines, including but not limited to, the Panc-1 cell line; breast tumor cell lines, including but not limited to, the MDA231 cell line and ovarian cell lines, including but not limited to, the OVCAR-3 cell line. Hemopoietic cell lines include, but are not limited to, the Raji and Daudi B-lymphold cells, K562 erythroblastoid cells, U937 myeloid cells, and HSB2 T-lymphoid cells. Any other tumor cell lines that are available can be used in evaluating and identifying adenoviruses of the invention for use in the treatment of neoplasia.

Figure 2:
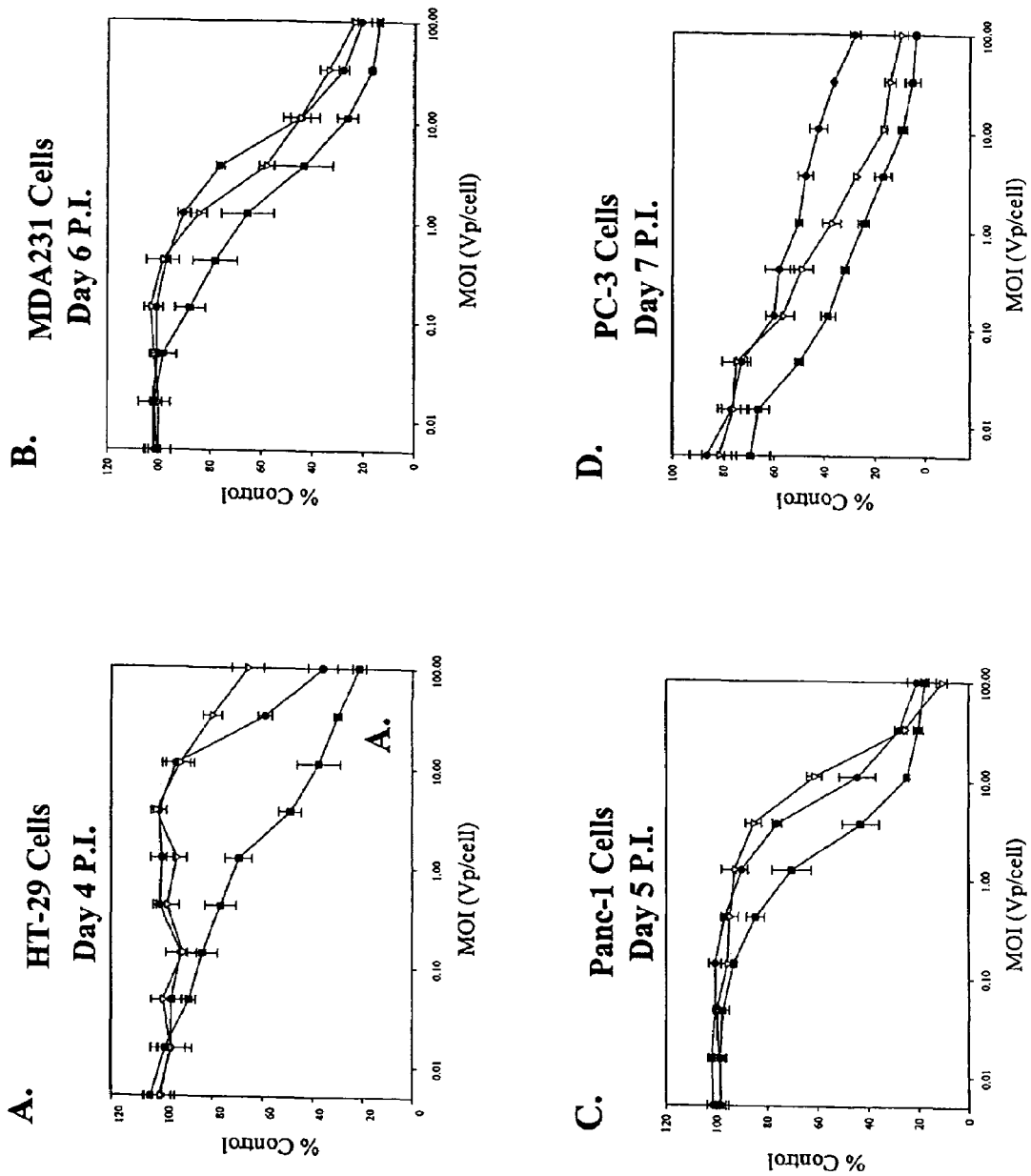
FIG. 2. Cytolytic activity of the individual virus pools. A) HT-29, B) MDA-231, C) Panc-1 and D) PC-3 cells were infected with their respective viral pools at VP per cell ratios from 100 to 0.01. MTS assays were performed on differing days post infection (as indicated) dependent upon the cell line. Each data point in the panel represents an assay done in quadruplicate and the results are expressed as the means ±SD. The panel depicts one representative experiment and all viral pools were assayed at least three independent times on the target tumor cell line (Figure Legend: -●-Ad5; -□- initial viral pool; -■- specific cell derived pool, passage 20).

The cytolytic activity of adenoviruses of the invention can be determined in representative tumor cell lines and the data converted to a measurement of potency, with an adenovirus belonging to subgroup C, preferably Ad5, being used as a standard (i.e. given a potency of 1). A preferred method for determining cytolytic activity is an MTS assay (see Example 4, FIG. 2).

Figure 4:
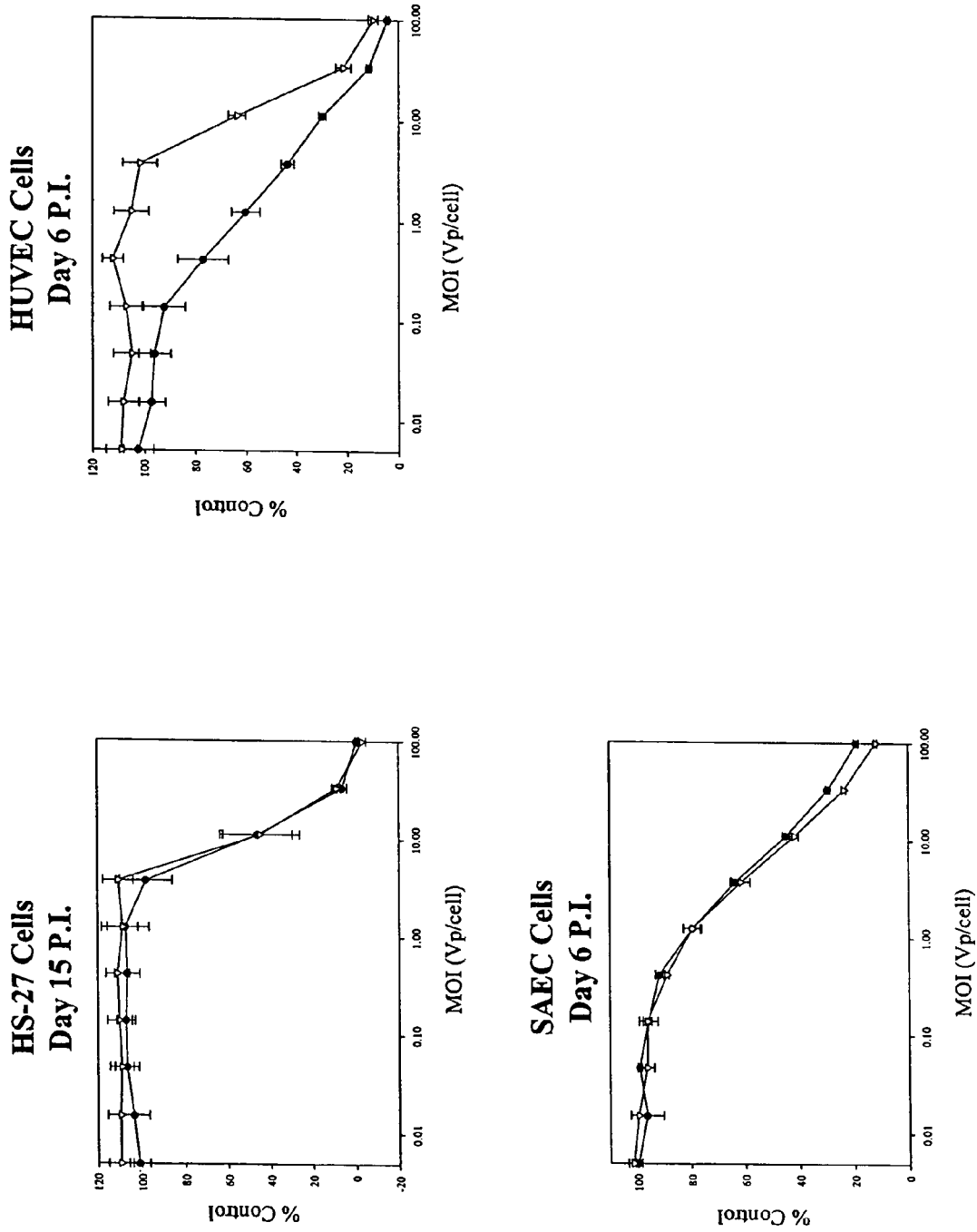
FIG. 4. Cytolytic activity of ColoAd1 and Ad5 on a panel of normal cells. HS-27, HUVEC and SAEC cells (primary fibroblast, endothelial, and epithelial cells, respectively) were infected with ColoAd1 and Ad5 at VP per cell ratios from 100 to 0.01. MTS assay was performed on differing days post infection dependent upon the cell and each panel is a representative experiment that has been repeated at least three times. Each data point in the panel represents an assay done in quadruplicate and the results are expressed as the means ±SD (Figure Legend: -●- Ad5; -□- ColoAd1).
Figure 5:
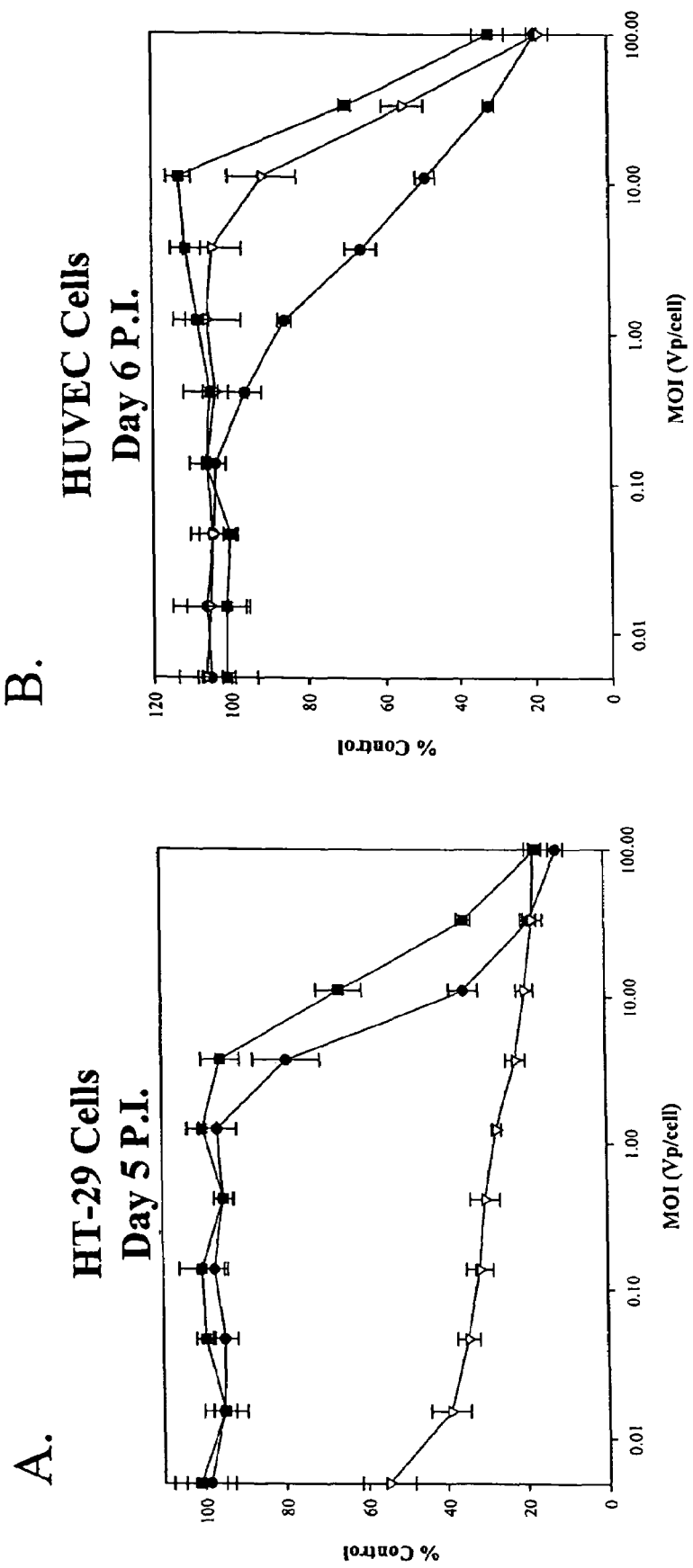
FIG. 5. Cytolytic activity of ColoAd1, Ad5 and ONYX-015 on primary normal endothelial cells (HUVEC) and a colon tumor cell line (HT-29). Each panel is a representative experiment that has been repeated at least three times. Each data point in the panel represents an assay done in quadruplicate and the results are expressed as the means ±SD (Figure Legend: -●- Ad5; -□- ColoAd1; -■- Onyx-015).

The therapeutic index of an adenovirus of the invention in a particular tumor cell line can be calculated by comparison of the potency of the given adenovirus in a tumor cell line with the potency of that same adenovirus in a noncancerous cell line. Preferred non-cancerous cell lines are SAEC cells, which are epithelial in origin, and HUVEC cells which are endothelial in origin (see FIG. 4). These two cell types represent normal cells from which organs and vasculature, respectively, are derived, and are representative of likely sites of toxicity during adenoviral therapy, depending on the mode of delivery of the adenovirus. However, practice of the invention is not limited to the use of these cells, and other non-cancerous cell lines (e.g. B cells, T cells, macrophages, monocytes, fibroblasts) may also be used.

The chimeric adenoviruses of the invention can be further evaluated for their ability to target neoplastic cell growth (i.e. cancer) by their capacity to reduce tumorigenesis or neoplastic cell burden in nude mice harboring a transplant of neoplastic cells, as compared to untreated mice harboring an equivalent neoplastic cell burden (see Example 7).

Evaluation of the adenoviruses of the invention can also be performed using primary human tumor explants (Lam et al. (2003) *Cancer Gene Therapy*; Grill et al. (2003) *Mol. Therapy* 6:609-614), which provide test conditions present in tumors that cannot normally be produced using the tumor xenograft studies.

Therapeutic Utility

The present invention provides for the use of chimeric adenoviruses of the invention for the inhibition of tumor cell growth, as well as for the use of adenoviral vectors derived from these chimeric adenoviruses to deliver therapeutic proteins useful in the treatment of neoplasia and other disease states.

Pharmaceutical Compositions and Administration

The present invention also relates to pharmaceutical compositions which comprise the chimeric adenoviruses of the invention, including variants and derivatives thereof, formulated for therapeutic administration to a patient. For therapeutic use, a sterile composition containing a pharmacologically effective dosage of adenovirus is administered to a human patient or veterinary non-human patient for treatment, for example, of a neoplastic condition. Generally, the composition will comprise about $10^{11}$ or more adenovirus particles in an aqueous suspension. A pharmaceutically acceptable carrier or excipient is often employed in such sterile compositions. A variety of aqueous solutions can be used, e.g. water, buffered water, 0.4% saline, 0.3%-glycine and the like. These solutions are sterile and generally free of particulate matter other than the desired adenoviral vector. The compositions may contain pharmaceutically acceptable auxiliary substances as required to approximate physiological conditions such as pH adjusting and buffering agents, toxicity adjusting agents and the like, e.g. sodium acetate, sodium chloride, potassium chloride, calcium chloride, sodium lactate, etc. Excipients which enhance infection of cells by adenovirus may be included. (see U.S. Pat. No. 6,392,069) Adenoviruses of the invention may also be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of adenovirus virions can be encapsulated in micelles to form immunoliposomes by conventional methods (U.S. Pat. No. 5,043,164, U.S. Pat. No. 4,957,735, U.S. Pat. No. 4,925,661; Connor and Huang, (1985) *J. Cell Biol*. 101: 581; Lasic D. D. (1992) *Nature* 355: 279; Novel Drug Delivery (eds. Prescott and Nimmo, Wiley, N.Y., 1989); Reddy et al. (1992) *J. Immunol*. 148:1585). Immunoliposomes comprising an antibody that binds specifically to a cancer cell antigen (e.g., CALLA, CEA) present on the cancer cells of the individual may be used to target virions to those cells (Fisher (2001) *Gene Therapy* 8:341-348).

To further increase the efficacy of the adenoviruses of the invention, they may be modified to exhibit enhanced tropism for particular tumor cell types. For example, as shown in PCT/US98/04964, a protein on the exterior coat of an adenovirus may be modified to display a chemical agent, preferably a polypeptide, that binds to a receptor present on tumor cells to a greater degree than normal cells. (See also, U.S. Pat. Nos. 5,770,442 and 5,712,136). The polypeptide can be an antibody, and preferably is a single chain antibody.

Adenoviral Therapy

The adenoviruses of the invention, or pharmaceutical compositions thereof, can be administered for therapeutic treatment of neoplastic disease or cancer. In therapeutic applications, compositions are administered to a patient already affected by the particular neoplastic disease, in an amount sufficient to cure or at least partially arrest the condition and its complications. An amount adequate to accomplish this is defined as a "therapeutically effective dose" or "efficacious dose". Amounts effective for this use will depend upon the severity of the condition, the general state of the patient, and the route of administration.

For example, but not by way of limitation, a human patient or non-human mammal having a solid or haemotologic neoplastic disease, (e.g. pancreatic, colon, ovarian, lung, or breast carcinoma, leukemia or multiple myeloma) may be treated by administering a therapeutically effective dosage of an appropriate adenovirus of the invention, i.e. one which has been shown to have an improved therapeutic index for that tissue type. For example, a preferred chimeric adenovirus for the treatment of colon cancer would be the adenovirus ColoAd1 (SEQ ID NO: 1). Suspensions of infectious adenovirus particles may be delivered to neoplastic tissue by various routes, including intravenous, intraperitoneal, intramuscular, subdermal, and topical. An adenovirus suspension containing about $10^3$ to $10^{12}$ or more virion particles per ml may be administered by infusion (e.g., into the peritoneal cavity for treating ovarian cancer, into the portal vein for treating hepatocarcinoma or liver metastases from other non-hepatic primary tumors) or other suitable route, including direct injection into a tumor mass (e.g. a breast tumor), enema (e.g., colon cancer), or catheter (e.g., bladder cancer). Other routes of administration may be suitable for carcinomas of other origins, i.e. inhalation as a mist (e.g., for pulmonary delivery to treat bronchogenic carcinoma, small-cell lung carcinoma non-small cell lung carcinoma, lung adenocarcinoma or laryngeal cancer) or direct application to a tumor site (e.g., bronchogenic carcinoma, nasopharyngeal carcinoma, laryngeal carcinoma, cervical carcinoma).

Adenoviral therapy using the adenoviruses of the instant invention may be combined with other antineoplastic protocols, such as conventional chemotherapy or x-ray therapy to treat a particular cancer. Treatment can be concurrent or sequential. A preferred chemotherapeutic agent is cisplatin, and the preferred dose may be chosen by the practitioner based on the nature of the cancer to be treated, and other factors routinely considered in administering cisplatin. Preferably, cisplatin will be administered intravenously at a dose of 50-120 mg/m² over 3-6 hours. More preferably it is administered intravenously at a dose of 80 mg/m² over 4 hours. A second preferred chemotherapeutic agent is 5-fluorouracil, which is often administered in combination with cisplatin. The preferred dose of 5-fluorouracil is 800-1200 mg/m² per day for 5 consecutive days.

Adenoviral therapy using the adenoviruses of the instant invention as adenoviral vectors may also be combined with other genes known to be useful in viral based therapy. See U.S. Pat. No. 5,648,478. In such cases, the chimeric adenovirus further comprises a heterologous gene that encodes a therapeutic protein, incorporated within the viral genome, such that the heterologous gene is expressed within an infected cell. A therapeutic protein, as used herein, refers to a protein that would be expected to provide some therapeutic benefit when expressed in a given cell.

In one embodiment, the heterologous gene is a pro-drug activator gene, such as cytosine deaminase (CD) (See, U.S. Pat. Nos. 5,631,236; 5,358,866; and 5,677,178). In other embodiments, the heterologous gene is a known inducer of cell-death, e.g apoptin or adenoviral death protein (ADP), or a fusion protein, e.g. fusogenic membrane glycoprotein (Danen-Van Oorschot et al. (1997) *Proc. Nat. Acad. Sci.* 94:5843-5847; Tollefson et al.(1996) *J. Virol.* 70:2296-2306; Fu et al. (2003) *Mol. Therapy* 7: 48-754, 2003; Ahmed et al. (2003) *Gene Therapy* 10:1663-1671, Galanis et al. (2001) *Human Gene Therapy* 12(7): 811-821).

Further examples of heterologous genies, of fragments thereof, include those that encode immunomodulatory proteins, such as cytokines or chemokines. Examples include interleukin 2, U.S. Pat. Nos. 4,738,927 or 5,641,665; interleukin 7, U.S. Pat. Nos. 4,965,195 or 5,328,988; and interleukin 12, U.S. Pat. No. 5,457,038; tumor necrosis factor alpha, U.S. Pat. Nos. 4,677,063 or 5,773,582; interferon gamma, U.S. Pat. Nos. 4,727,138 or 4,762,791; or GM CSF, U.S. Pat. Nos. 5,393,870 or 5,391,485, Mackensen et al. (1997) *Cytokine Growth Factor Rev.* 8:119-128). Additional immunomodulatory proteins further include macrophage inflammatory proteins, including MIP-3. Monocyte chemotatic protein (MCP-3 alpha) may also be used; a preferred embodiment of a heterologous gene is a chimeric gene consisting of a gene that encodes a protein that traverses cell membranes, for example, VP22 or TAT, fused to a gene that encodes a protein that is preferably toxic to cancer but not normal cells.

The chimeric adenoviruses of the invention can also be used as vectors to deliver genes encoding therapeutically useful RNA molecules, i.e. siRNA (Dorsett and Tuschl (2004) *Nature Rev Drug Disc* 3:318-329).

In some cases, genes can be incorporated into a chimeric adenovirus of the invention to further enhance the ability of the oncolytic virus to eradicate the tumor, although not having any direct impact on the tumor itself—these include genes encoding proteins that compromise MHC class I presentation (Hewitt et al. (2003) *Immunology* 110: 163-169), block complement, inhibit IFNs and IFN-induced mechanisms, chemokines and cytokines, NK cell based killing (Orange et al., (2002) *Nature Immunol.* 3: 1006-1012; Mireille et al. (2002) *Immunogenetics* 54: 527-542; Alcami (2003) *Nature Rev. Immunol.* 3: 36-50; down regulate the immune response (e.g. IL-10, TGF-Beta, Khong and Restifo (2002) *Nature Immunol.* 3: 999-1005; 2002) and metalloproteases which can breakdown the extracelluar matrix and enhance spread of the virus within the tumor (Bosman and Stamenkovic (2003) *J. Pathol.* 2000: 423-428; Visse and Nagase (2003) *Circulation Res.* 92: 827-839).

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

The present invention is further described by the following examples, which are illustrative of specific embodiments of the invention, and various uses thereof. These exemplifications, which illustrating certain specific aspects of the invention, do not portray the limitations or circumscribe the scope of the disclosed invention.

Unless otherwise Indicated, the practice of the present Invention employs conventional techniques of cell culture, molecular biology, microbiology, recombinant DNA manipulation, immunology science, which are within the skill of the art. Such techniques are explained fully in the literature. See, e.g. Cell Biology: a Laboratory Handbook: J. Celis (Ed).Academic Press. N.Y. (1996); Graham, F. L. and Prevec, L. Adenovirus-based expression vectors and recombinant vaccines. In: Vaccines: New Approaches to Immunological Problems. R. W. Ellis (ed) Butterworth. Pp 363-390; Grahan and Prevec Manipulation of adenovirus vectors. In: Methods in Molecular Biology, Vol. 7: Gene Transfer and Expression Techniques. E. J. Murray and J. M. Walker (eds) Humana Press Inc., Clifton, N. J. pp 109-128, 1991; Sambrook et al. (1989), Molecular Cloning, A Laboratory Manual, 2nd ed., Cold Spring Harbor Laboratory Press; Sambrook et al. (1989), and Ausubel et al. (1995), Short Protocols in Molecular Biology, John Wiley and Sons.

EXAMPLES

Methods

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., Molecular Cloning: A Laboratory Manual, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation and delivery, and treatment of patients. Methods for the construction of adenoviral mutants are generally known in the art. See, Mittal, S. K., Virus Res.,1993, vol: 28, pages 67-90; and Hermiston, T. et al., Methods in Molecular Medicine: Adenovirus Methods and Protocols, W. S. M. Wold, ed, Humana Press, 1999. Further, the adenovirus 5 genome is registered as Genbank 10 accession #M73260, and the virus is available from the American Type Culture Collection, Rockville, Md., U. S. A., under accession number VR-5.

Viruses and Cell Lines

The Ad serotypes Ad3 (GB strain), Ad4 (RI-67 strain), Ad5 (Adenoid 75 strain), Ad9 (Hicks strain), Ad11p (Slobitski strain), Ad16 (Ch. 79 strain) and all the cell lines, with the exception of the following were all purchased from the ATCC: MDA231-mt1 (a derivative isolated by Dr. Deb Zajchowski from a rapidly growing subcutaneous implanted xenograft of MDA231 cells) and Panc1-sct (derived by Dr. Sandra Biroc from a rapidly growing subcutaneous implanted xenograft of Panc1 cells), HUVEC (Vec Technologies, Rensselaer, N.Y.), and SAEC (Clonetics, Walkersville, Md.). Ad40 was a kind gift from Dr. William S. M. Wold at St. Louis University.

Example 1

Viral Purification and Quantitation

Viral stocks were propagated on 293 cells and purified on CsCl gradients (Hawkins et al., 2001). The method used to quantitate viral particles is based on that of Shabram et al. (1997) *Human Gene Therapy* 8:453-465, with the exception that the anion-exchanger TMAE Fractogel was used instead of Resource Q. In brief, a 1.25 ml column was packed with Fractogel EMD TMAE-650 (S) (catalog # 116887-7 EM Science, Gibbstown, N.J. 08027). HPLC separation was performed on an Agilent HP 1100 HPLC using the following conditions: Buffer A=50 mM HEPES, pH 7.5; Buffer B=1.0 M NaCl in Buffer A; flow rate of 1 ml per minute. After column equilibration for not less than 30 minutes in Buffer A, approximately $10^9$-$10^{11}$ viral particles of sample were loaded onto the column in 10-100 ul volume, followed by 4 column volumes of Buffer A. A linear gradient extending over 16 column volumes and ending in 100% Buffer B was applied.

The column effluent was monitored at A260 and A280 nm, peak areas calculated, and the 260 to 280 nm ratio determined. Viral peaks were identified as those peaks having a A260/A280 ratio close to 1.33. A virus standard was included with each sample series. The number of viral particles per ml of the standard had been determined using the method of Lehmberg et al. (1999) *J. Chrom. B,* 732:411-423}. In the viral concentration range used, the A260 nm peak area of each sample is directly proportional to the number of viral particles in the sample. The number of viral particles per ml in each test sample was calculated by multiplying the known number of viral particles per ml in the standard by the ratio of the A260 nm viral peak area of the sample to the A260 nm viral peak area of the standard.

The column was regenerated after each sample gradient by washing with two column volumes of 0.5 N NaOH followed by two column volumes of 100% Buffer A, 3 column volumes of 100% Buffer B, and then 4 column volumes of 100% Buffer A.

Example 2

Bioselection

Viral serotypes representing subgroups Ads B-F were pooled and passaged on sub-confluent cultures of the target tumor cell lines at a high particle-per-cell ratio for two rounds to invite recombination to occur between serotypes. Supernatant (1.0, 0.1 0.01, 0.001 ml) from the second round of the high viral particle-per-cell infection, subconfluent cultures, was then used to infect a series of over-confluent T-75 tissue culture flasks of target tumor cell lines PC-3, HT-29, Panc-1 and MDA-231. To achieve over-confluency, each cell line was seeded at split ratios that allowed that cell line to reach confluency between 24 and 40 hours post seeding, and the cells were allowed to grow a total of 72 hours post seeding prior to infection. This was done to maximize the confluency of the cells to mimic growth conditions in human solid tumors.

Cell culture supernatant was harvested from the first flask in the 10-fold dilution series that did not show any sign of CPE at day 3 or 4 post-infection (in the case of HT-29 and PC-3, this was modified for passages 10-20 to harvest of the second flask, i.e. harvest 100-fold below the dilution in which CPE were detectable by day 3 post-infection). Each harvest served as the starting material for the successive passage of the virus. This process was repeated until the viral pool achieved 20 bioselective passages.

Individual viruses from each bioselected pool were isolated by two rounds of plaque purification on A549 cells using standard methods (Tollefson, A., Hermiston, T. W., and Wold, W. S. M.; "Preparation and Titration of CsCl-banded Adenovirus Stock" in *Adenovirus Methods and Protocols*, Humana Press, 1999, pp 1-10, W. S. M. Wold, Ed). In brief, dilutions of the supernatant harvested from the 20th passage on each target tumor line were used to infect A549 cells in a standard plaque assay. Well-individuated plaques were harvested, and the same plaque assay method was used to generate a second round of individual plaques from these harvests. Well isolated plaques from the second round of plaque purification were deemed pure, infected cultures were prepared using these purified plaques, and the oncolytic potency of these culture supernatants determined by MTS assay as described.

Example 3

Serotype Characterization

The parental adenoviral serotypes comprising the viral pools or the isolated ColoAd1 adenovirus were identified using anion-exchange chromatography similar to that described in Shabram et al. (1997) *Human Gene Therapy* 8:453:465, with the exception that the anion-exchanger TMAE Fractogel media (EM Industries, Gibbstown, N.J.) was used instead of Resource Q. as described in Example 1 (see FIG. 1).

Adenovirus type 5 eluted at approximately 60% Buffer B during the gradient. The other serotypes (3, 4, 9, 11 p, 16, 35, and 40) each eluted at a characteristic retention time consistent with the retention times on Q Sepharose XL published by Blanche et al. (2000) *Gene Therapy* 7:1055-1062.

Example 4

Cytolytic Assay

The viral lytic capacity was measured by using a modification of the MTT assay (Shen et al., 2001). Briefly, the MTS assay (Promega, CellTiter 96(R) Aqueous Non-Radioactive Cell Proliferation Assay) was used in place of the MTT assay since conversion of MTS by cells Into aqueous, soluble formazan reduces time and eliminates the use of a volatile organic solvent associated with the MTT assay.

To perform the assay, cells were seeded at a defined density for each tumor cell line that generated a confluent monolayer within 24 hr. These densely seeded cells were allowed to grow for 2 additional days prior to exposure to the test virus(es). Infections of both tumor and primary normal cells were carried out in quadruplicate with serial three fold dilutions of the viruses starting at a particle per cell ratio of 100 and ending at a particle per cell ratio of 0.005. Infected cells were incubated at 37° C. and the MTS assay was performed at the time points indicated for the individual primary cells or tumor cell lines. Mock-infected cells served as negative controls and established the 100% survival point for the given assay.

Example 5

DNA Sequencing

DNA sequencing of the Ad11p (SEQ ID NO: 2) and ColoAd1 (SEQ ID NO: 1) genomic DNAs was performed as follows. Briefly, purified adenovirus DNA from ColoAd1 and Ad11p was partially digested with the restriction endonuclease Sau3A1 and shotgun cloned into the plasmid vector pBluescript II (Stratagene, La Jolla, Calif.). Positive clones were propagated and sequenced using the primers M13R and KS (Stratagene, La Jolla, Calif.). Individual sequence reactions were trimmed, edited and assembled using Sequencher$^{tm}$ (Gene Codes Corp., Ann Arbor, Mich.). Gaps in coverage were amplified with custom oligonucleotide primers and sequenced. The ends of the viral genomes were sequenced directly off the adenoviral DNA. In all, each genome was sequenced at 3×+ coverage and 431 bases at 2× coverage.

To determine the origin of the ColoAd1 E2B region, two primer sets were generated, one to the E2B pTP gene (bp9115, 5'GGGAGTTTCGCGCGGACACGG3' (SEQ ID NO: 4) and bp 9350, 5'GCGCCGCCGCCGCGGAGAGGT3' (SEQ ID NO: 5)) and one to the DNA polymerase gene (bp 7520 5'CGAGAGCCCATTCGTGCAGGTGAG3' (SEQ ID NO: 6) and bp 7982, 5'GCTGCGACTACTGCGGC-CGTCTGT3' (SEQ ID NO: 7) and used to PCR isolate DNA fragments from the various serotypes (Ad3,4,5,9,11 p,16 and 40) using reagents from the Advantage 2 PCR kit (Clonetics, Walkersville, Md.; Cat #K1910-Y) and run on a PTC-200 thermocycler from MJ Research (Watertown, Mass.). These fragments were subsequently sequenced along with the DNA sequence of Ad3 using dye terminator sequencing on as ABI 3100 genetic analyzer.

The E2B region of Ad3 was sequenced using isolated Ad3 DNA and overlapping primers.

Sequence information was analyzed using the Vector NTI program (Informatix).

Example 6

Construction of Recombinant Viruses

Genomic DNAs of Ad11p (SEQ ID NO: 2) and ColoAd1 (SEQ ID NO: 1) were purified from CsCl gradient-banded virus particles. The genomic DNAs were digested with Pacl which cuts each only once within the viral genome. The Pac1 cut occurs at base 18141 on ColoAd1 nucleotide sequence (SEQ ID NO: 1) and at base 18140 on the Ad11 nucleotide sequence (SEQ ID NO: 2). Digested DNAs were mixed in equal amounts and ligated in the presence of T4 DNA ligase at 16° C. overnight. This ligation mixture was transfected into A549 cells using the CaPO$_4$ transfection kit from Invitrogen, Carlsbad, Calif. (Cat #K2780-01). Isolated plaques were picked and screened by restriction enzyme digestion and PCR analysis to distinguish the four viral populations (Ad11p, ColoAd1, left end Ad11p/right end ColoAd1 (ColoAd1.1) and left end ColoAd1/right end Ad11p(ColoAd1.2)).

The viral lytic capacity of each population was determined in several cell lines, including HT29 and HUVEC cell lines, as described in Example 3. The results demonstrated the order of potency, from least potent to most potent, as Ad11p, ColoAd1.2, ColoAd1.1, ColoAd1 (see FIG. 7 for the results in HT29 cells).

Also constructed were chimeric adenoviruses pCJ144 and pCJ146, which contain the full-length ColoAd1 genome in which the wild-type Ad11p E3 and E4 region, respectively, has been restored. These modifications were introduced by homologous recombination into BJ5183 *E. Coli* (Chartier et al. (1996) *J. Virol.* 70:4805-4810). Both of these chimeric adenoviruses demonstrated reduced lytic capacity in HT29 and HUVEC cells compared to ColoAd1 or ColoAd1.2.

Example 7

In Vivo Efficacy of Adenovirus

In a typical human tumor xenograft nude mouse experiment, animals are injected with $5 \times 10^6$ cells subcutaneously into the hind flank of the mouse. When the tumors reach 100-200 ul in size, they are injected with vehicle (PBS) or with virus at $2 \times 10^{10}$ particles for five consecutive days ($1 \times 10^{11}$ particles total). A reduction in the size of the tumor would be noted relative to the PBS control and additional control viruses (Ad5, ONYX-015).

Example 8

ColoAd1 Selectivity on Primary Human Tissue Explants

Tissue specimens from colorectal tumors and adjacent normal tissues removed during surgery were placed in culture media and infected with equal numbers of either ColoAd1 or Ad5 viruses. Culture supernatants were collected at 24 hours post infection and the number of virus particles produced was determined. ColoAd1 produced more virus particles per input particle than Ad5 on tumor tissue, while it produced fewer particles per input particle than Ad5 on normal tissue.

We claim:

1. A recombinant chimeric adenovirus, or a variant or derivative thereof, having a genome comprising an E2B region
   wherein said E2B region comprises a nucleic acid sequence derived from a first adenoviral serotype and a nucleic acid sequence derived from a second adenoviral serotype, wherein the nucleotide sequence of the E2B region of said adenovirus comprises SEQ ID NO:3;
   wherein said first and second serotypes are each selected from the adenoviral subgroups B, C, D, E, or F and are distinct from each other; and
   wherein said chimeric adenovirus is oncolytic.

2. The adenovirus of claim 1 further comprising regions encoding fiber, hexon, and penton proteins, wherein the nucleic acid encoding the fiber, hexon, and penton proteins of said adenovirus are from the same adenoviral serotype.

3. The adenovirus of claim 1 further comprising a modified E4 region.

4. The adenovirus of claim 1, wherein said tumor cell is a colon, breast, pancreas, lung, prostate, ovarian, or hemopoietic tumor cell.

5. The adenovirus of claim 4, wherein said tumor cell is a colon tumor cell.

6. The adenovirus of claim 1, wherein the nucleotide sequence of said adenovirus comprises SEQ ID NO: 1.

* * * * *